United States Patent
Okubara et al.

(12) 
(10) Patent No.: US 6,521,435 B1
(45) Date of Patent: Feb. 18, 2003

(54) NUCLEIC ACID SEQUENCES ENCODING CELL WALL-DEGRADING ENZYMES AND USE TO ENGINEER RESISTANCE TO FUSARIUM AND OTHER PATHOGENS

(75) Inventors: Patricia A. Okubara, Richmond, CA (US); Ann E. Blechl, Albany, CA (US); Thomas M. Hohn, Chapel Hill, NC (US); Randy M. Berka, Davis, CA (US)

(73) Assignees: The United States of America as represented by the Secretary of Agriculture, Washington, DC (US); Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/649,747

(22) Filed: Aug. 28, 2000

Related U.S. Application Data

(60) Provisional application No. 60/224,946, filed on Aug. 11, 2000, and provisional application No. 60/151,582, filed on Aug. 30, 1999.

(51) Int. Cl.$^7$ ............. C12N 9/00; C12N 5/04; C12P 21/06; C07H 21/04; A01H 5/00

(52) U.S. Cl. ............. 435/206; 435/183; 435/200; 435/252.3; 435/320.1; 435/419; 435/468; 435/69.1; 536/23.2; 800/295; 800/298; 800/320.3

(58) Field of Search ............. 435/69.1, 183, 435/200, 206, 210, 209, 252.3, 320.1, 419, 468; 800/295, 298, 320.3; 536/23.2

(56) References Cited

U.S. PATENT DOCUMENTS

| | | |
|---|---|---|
| 5,290,687 A | 3/1994 | Suslow et al. |
| 5,374,540 A | 12/1994 | Suslow et al. |
| 5,378,821 A | 1/1995 | Harman et al. |
| 5,446,138 A | 8/1995 | Blaiseu et al. |
| 5,554,521 A | 9/1996 | Suslow et al. |
| 5,633,450 A | 5/1997 | Suslow et al. |
| 5,670,706 A | 9/1997 | Cornelissen et al. |
| 5,804,184 A | 9/1998 | Logemann et al. |
| 5,919,688 A | 7/1999 | Ferrer et al. |

OTHER PUBLICATIONS

Edington et al. Plant Mol. Biol., 1991, vol. 16(1):81–94.*
Ortega et al. Plant Physiol., 1997, vol. 113(4):1453–60.*
R. Beffa and F. Meins, Jr, "Pathogenesis–related functions of plant β–1, 3–glucanases investigated by antisense transformation—a review," (1996) *Gene* 179:97–103.
P.–L. Blaiseau and J.–F. Lafay, "Primary structure of a chitinase–encoding gene (chi1) from the filamentous fungus *Aphanocladium album*: similarity to bacterial chitinases," (1992) *Gene* 120:243–248.
M. Bliffeld et al., "Genetic engineering of wheat for increased resistance to powdery mildew disease," (1999) *Theor Appl Genet* 98:1079–1086.
J.P. Bolar et al., "Expression of Endochitinase from *Trichoderma harzianum* in Transgenic Apple Increases Resistance to Apple Scab and Reduces Vigor," (2000) *Phytopathology* 90(1):72–77.
R. Boyapati, A.L. Moyne, T.E. Cleveland and S. Tuzun, "Cloning of Putative Chitinase Genes From Bacillus to Control Toxin Producing Fungi," (1994) *Phytopathology* 84(10):1081.
M. Chérif and N. Benhamou, "Cytochemical Aspects of Chitin Breakdown During the Parasitic Action of a Trichoderma sp. on *Fusarium oxysporum* f. sp. *radicis–lycopersici*," (1990) *Phytopathology* 80(12):1406–1414.
A.H. Christensen and P.H. Quail, "Ubiquitin promoter–based vectors for high–level expression of selectable and/or screenable marker genes in monocotyledonous plants," (1996) *Transgenic Research* 5:213–218.
D.B. Collinge et al., "Plant chitinases," (1993) *The Plant Journal* 3(1):31–40.
M. De Block et al., "Engineering herbicide resistance in plants by expression of a detoxifying enzyme," (1987) *The EMBO Journal* 6(9):2513–2518.
J. De La Cruz et al., "Isolation and characterization of three chitinases from *Trichoderma harzianum*," (1992) *Eur. J. Biochem.* 206:859–867.
H. Draborg, S. Kauppinen, H. Dalbøge, and S. Christgau, "Molecular Cloning and Expression in *S. Cerevisiae* of Two Exochitinases from *Trichoderma harzianum*," (1995) *Biochemistry and Molecular Biology International* 36(4):781–791.
A. Blechl, "U.S. Wheat and Barley Scab Initiative Grant," (Jan. 2000) pp. I–iv and 1–12.
J.D. Faris, W.L. Li, D.J. Liu, P.D. Chen and B.S. Gill, "Candidate gene analysis of quantitative disease resistance in wheat," (1999) *Theor Appl Genet* 98:219–225.
J. Flach, P.–E. Pilet and P. Jollès, "What's new in chitinase research?," (1992) *Experientia* 48:701–716.
T. Fontaine et al., "Differential Patterns of Activity Displayed by Two Exo–β–1,3–Glucanases Associated with the *Aspergillus fumigatus* Cell Wall," (1997) *Journal of Bacteriology* 179(10):3154–3163.

(List continued on next page.)

*Primary Examiner*—Rebecca E. Prouty
*Assistant Examiner*—Manjunath N. Rao
(74) *Attorney, Agent, or Firm*—Margaret A. Conner; M. Howard Silverstein; John D. Fado

(57) ABSTRACT

The invention is directed to nucleic acid sequences derived from Fusarium fungal genes which encode the cell wall-degrading enzymes glucanase, endochitinase, and exochitinase; isolated polypeptides having glucanase, endochitinase or exochitinase activity; recombinant nucleic acid molecules, vectors, and host cells comprising the nucleic acid sequences as well as methods for producing and using the polypeptides, including expression in plant cells to confer or enhance a plant's resistance to Fusarium and other pathogens.

11 Claims, 20 Drawing Sheets

OTHER PUBLICATIONS

G.E. Harman et al., "Chitinolytic Enzymes of *Trichoderma harzianum*: Purification of Chitobiosidase and Endochitinase," (1993) *Phytopathology* 83(3):313–318.

C.K. Hayes et al., "Isolation and sequence of an endochitinase–encoding gene from a cDNA library of *Trichoderma harzianum,*" *Gene* (1994) 138:143–146.

F. Klebl and W. Tanner, "Molecular Cloning of a Cell Wall Exp–$\beta$–1,3–Glucanase from *Saccharomyces cerevisiae*," (1989) *Journal of Bacteriology* 171(11):6259–6264.

K. Koga et al., "Purification and Characterization of $\beta$–N–Acetylhexosaminidase from *Trichoderma harzianum,*" (1991) *Agric. Biol. Chem.* 55(11):2817–2823.

G. Leckband and H. Lorz, "Transformation and expression of a stilbene synthase gene of *Vitis vinifera* L. in barley and wheat for increased fungal resistance," (1998) *Theor Appl Genet* 96:1004–1012.

M. Lorito et al., "Chitinolytic Enzymes Produced by *Trichoderma harzianum*: Antifungal Activity of Purified Endochitinase and Chitobiosidase," (1993) *Phytopathology* 83(3):302–307.

M. Lorito et al., "Genes from mycoparasitic fungi as a source for improving plant resistance to fungal pathogens," (1998) *Proc. Natl. Acad. Sci.* 95:7860–7865.

N.S. Nehra et al., "Self–fertile transgenic wheat plants regenerated from isolated scutellar tissues following microprojectile bombardment with two distinct gene constructs," (1994) *The Plant Journal* 5(2):285–297.

O. M. Nuero, "Production of Chitinase by Fusarium Species," (1995) *Current Microbiology* 30:287–289.

C.K. Peterbauer et al., "Molecular cloning and expression of the nag1 gene (N–acetyl–$\beta$–D–glucosaminidase–encoding gene) from *Trichoderma harzianum* P1," (1996) *Curr Genet* 30:325–331.

E.J. Pishko, T.N. Kirkland, and G. T. Cole, "Isolation and characterization of two chitinase–encoding genes (cts1, cts2) from the fungus *Coccidioides immitis*," (1995) *Gene* 167:173–177.

C. Pritsch et al., "Fungal Development and Induction of Defense Response Genes During Early Infection of Wheat Spikes by *Fusarium graminearum*," (2000) *Molecular Plant–Microbe Interactions* 13(2):159–169.

A. Sivan and I. Chet, "Degradation of Fungal Cell Walls by Lytic Enzymes of *Trichoderma harzianum*," (1989) *Journal of General Microbiology* 135:675–682.

R.W. Skadsen et al., "Targeting of Antifungal Genes to Inhibit Growth of *Fusarium Graminearum* in Barley," (Dec. 5–7, 1999) National Fusarium Head Blight Forum, Sioux Falls, South Dakota, pp. 35–39.

B.G. Spratt et al., "Kanamycin–resistant vectors that are analogues of plasmids pUC8, pUC9, pEMBL8 and pEMBL9," (1986) *Gene* 41:337–342.

T. Terakawa et al., "A fungal chitinase gene from *Rhizopus oligosporus* confers antifungal activity to transgenic tobacco." (1997) *Plant Cell Reports* 16:439–443.

V. Vasil et al., "Rapid Production of Transgenic Wheat Plants by Direct Bombardment of Cultured Immature Embryos," (1993) *Bio/Technology* 11:1553–1558.

J.T. Weeks, O.D. Anderson and A.E. Blechl, "Rapid Production of Multiple Independent Lines of Fertile Transgenic Wheat (*Triticum aestivum*)," (1993) *Plant Physiol.* 102:1077–1084.

C. Yang, Y. Zhu, D.M. Magee and R.A. Cox, "Molecular Cloning and Characterization of the *Coccidioides immitis* Complement Fixation/Chitinase Antigen," (1996) *Infection and Immunity* 64(6):1992–1997.

C.R. Zimmermann et al., "Cloning and Expression of the Complement Fixation Antigen–Chitinase of *Coccidioides immitis*," (1996) *Infection and Immunity* 64(12):4967–4978.

P. Okubara, C. Beamish, J. Lin, C. Montejo, O. Anderson, and A. Blechl, "#373 Transgenic Lines of Wheat (*Triticum Aestivum*) Carrying Genes for Candidate Anti–Fusarium Proteins," (Jun. 23–28, 1999) American Society Plant Physiologist Meeting (Poster Presentation). No. 373.

P. Okubara, T. Hohn, R. Berka, O. Anderson, and A. Blechl, "Expression of Candidate Anti–Fusarium Protein Genes in Hexaploid Wheat," (Aug. 12–16, 2000) American Phytopathology Society Meeting (Poster Presentation).

P. Okubara, T. Hohn, O. Anderson and A.E. Blechl, "Engineering Wheat for Resistance to Head Blight," (Aug. 30–Sep. 1, 1998) *Impact of Molecular Biology on Crop Production*, St. Paul MI (Poster Presentation).

P. Okubara, T. Hohn, O. Anderson, and A. Blechl, "Transformation of Wheat for Resistance to Fusarium Head Blight," (Oct. 26–27, 1998) National Fusarium Head Blight Forum (Poster Presentation).

P. Okubara, T. Hohn, O. Anderson, and A. Blechl, "Transformation of Wheat for Resistance to Fusarium Head Blight," (Oct. 26–27, 1998) National Fusarium Head Blight Forum (Abstract).

P. Okubara, C. Beamish, J. Lin, C. Montejo, O. Anderson, and A. Blechl, "Expression of Candidate Anti–Fusarium Protein Genes in Hexaploid Wheat," (Dec. 5–7, 1999) 1999 National Fusarium Head Blight Forum, Sioux Falls, South Dakota p. 30–33.

P. Okubara, C. Beamish, J. Lin, C. Montejo, O. Anderson, and A. Blechl, "Expression of Candidate Anti–Fusarium Protein Genes in Hexaploid Wheat," (Dec. 5–7, 1999) 1999 National Fusarium Head Blight Forum, Sioux Falls, South Dakota (Poster Presentation).

Christakopoulous, P. et al., "Purification and Characterization of a Less Randomly Acting Endo–1,4–$\beta$–D–glucanase from the Culture Filtrates of *Fusarium oxysporum,*" *Arch. Biochem. Biophys.* (1995) 316:428–433.

Mathivanan, N. et al., "Purification, Characterization, and Antifungal Activity of Chitinase From *Fusarium chlamydosporum*, a mycoparasite to groundnut rust, *Puccinia arachidis,*" *Can. J. Microbiol.* (1998) 44:464–651.

Christakopoulous, P. et al., "Multiple Forms of Endo–1,4–$\beta$–D–glucanase in the Extracellular Cellulas System of *Fusarium oxysporum*," *Biochem. Soc. Trans.* (1995) 23:586S.

\* cited by examiner

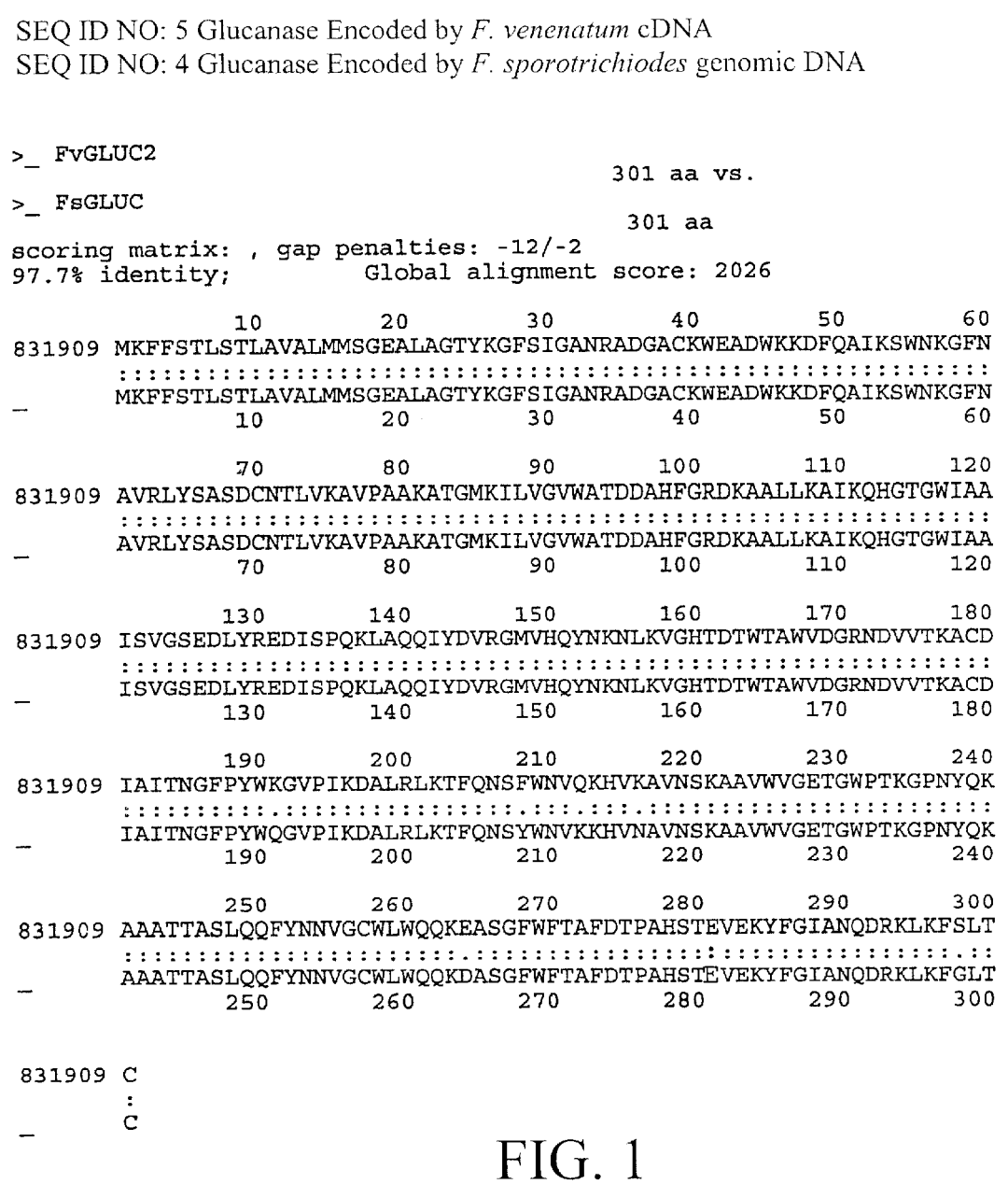

SEQ ID NO: 5 Glucanase Encoded by *F. venenatum* cDNA
SEQ ID NO: 4 Glucanase Encoded by *F. sporotrichiodes* genomic DNA

```
>_ FvGLUC2
                                             301 aa vs.
>_ FsGLUC
                                             301 aa
scoring matrix: , gap penalties: -12/-2
97.7% identity;         Global alignment score: 2026

10        20        30        40        50        60
831

SEQ ID NO: 6 *F. venenatum* Endochitinase 5' cDNA PCR Product
SEQ ID NO: 7 Deduced Polypeptide Sequence 5'
GATTCATTCCCCACCTAAAACCCCTCCAAGTGCCCTTCCATCATCACG
AATCTTCCACAGAGACAGCCAAGACTACGCCTTGGAAATCGTACCAGG
GCGAGCCTTTTACTTATAACCGCCGTTTTCGCTGCATTAGTTGCAGTA
TTCCTATCAAATACATCTTTATCTAGTCCCTTTACTTCAATCAAAATG
                                                                  M
GGTGGTGGACCCGAAGGTTTCCGCACCGTTGCGTATTTCGTCAACTGG
 G  G  G  P  E  G  F  R  T  V  A  Y  F  V  N  W
GCTATCTATGCACGAAAGCATCGTCCTCAGGATCTTCCCGTGGAGAAC
 A  I  Y  A  R  K  H  R  P  Q  D  L  P  V  E  N
CTGACACATATTCTTTACTCGTTCGCTAATATTCGTAGCGACTCTGGC
 L  T  H  I  L  Y  S  F  A  N  I  R  S  D  S  G
GAAGTCCATCTCACCGACTCATGGGCCGATACCGATATTCATTGGGAT
 E  V  H  L  T  D  S  W  A  D  T  D  I  H  W  D
GGAGATTCCTGGAATGATGTCGGTACCAACTTGTACGGTTGCATGAAG
 G  D  S  W  N  D  V  G  T  N  L  Y  G  C  M  K
CAGCTTAACCTGTTGAAAAGACGTAACCGAAACCTCAAG
 Q  L  N  L  L  K  R  R  N  R  N  L  K

FIG. 2

SEQ ID NO: 8 *F. sporotrichioides* Exochitinase 5' Genomic PCR Product
SEQ ID NO: 9 Deduced Polypeptide Sequence 5'
GATTCCCAAGGGGGCGGAACTGGAAGATCATCGCCGGTCTTATTAAACGGGN
ACTGGTACTTTGGACACTTTTGTCTCTTCCTTAAAGATTAGCCTCCCTCGCT
CAGCTTCTATCTACCATTGTTAGCAATTATCTCACTCACCTCACCTCTAGGC
GTAATGTGGTCCAAGGCTCTTCTGGCCGTTGCCGCCTTTGCCTTCACACCCG
     M  W  S  K  A  L  L  A  V  A  A  F  A  F  T  P CCAATGCTATATGGCCAGTGCCAAAGAAGATCTCTACTGGAGACAAGGCCCT
 A  N  A  I  W  P  V  P  K  K  I  S  T  G  D  K  A  L CTTCATCGATCAAACGATTGACNTCACCTACAATGGAGACTTTGTACGGGAC
  F  I  D  Q  T  I  D  ?  T  Y  N  G  D  F TCTCCCCGGTTCTGATTCCGATTCTGGTGCTTGTAACCATACCGCGCAGCTC
AATACTGAAACTTTGCTTCACAAACAGATCCCCTACACTTACAATTACCAAC
                                  I  P  Y  T  Y  N  Y  Q CCGATGCTGGCTCCAAGTTCAGTAGCAAGCAAATCATCCAAGCCGGCGTCTC
 P  D  A  G  S  K  F  S  S  K  Q  I  I  Q  A  G  V  S TCGTGCCCTCCAAGGCGTCTTCCAGGACAACTTTGTCCCATGGATGCTCCGC
GAACGCGACTCCGATTTTGAGCCTGACCTGCAAAAGAAGCAGTGGGTGAAGT
CGCTAAAGATTATCCAGACCGAGGAGGATGACGAGAGCACCTTCAAGCCTCT
CAATGGTGAGGTTGACGAGTCGTACTCCCTCTCACTTTCTGAGAAGGGCGAG
GCTTCCATCAAGGCCAAGTCCTCTACAGGTGTCCTGCACGGACTTGAGACCT
TTGTCCAACTTTTCTTCAAGCACAGCTCTGGCACTTCCTGGTACACGCCGCA
CGCGCCTGTCTCGATCCAGGACGAGCCCGAGTACCCTCATCGAGGTATCCTT
CTCGATGTTGCCCGTAGCTTTTTTGAAGTCAAGCACATCAAGCGCACAATCG
ATGCCATGTCGTGGAGCAAGTTGAATCGCCTTCACCTCCACATCACTGACTC
GCAGTCCTGGCCTCTCGAGATCCCAGCCCTGCCCAAGCTGGCCGAAAAGGGC
GCGTACC Underline indicates an intron

FIG. 3

SEQ ID NO: 14 Exochitinase Encoded by *F. venenatum* cDNA
SEQ ID NO: 15 Exochitinase Encoded by *F. sporotrichiodes* genomic DNA

```
>_ FvEXO2
                                              249 aa vs.
>_ FsEXO
                                              249 aa
scoring matrix: , gap penalties: -12/-2
97.6% identity;          Global alignment score: 1644

10        20        30        40        50        60
693206  MWSKALLAVAAFAFTPANAIWPVPKKISTGDKAFFIDQTIDITYNGGFIPYTYNYQPDAG
        ::::::::::::::::::::::::::::::::::.:::::: ::::  ::::::::::::
   -    MWSKALLAVAAFAFTPANAIWPVPKKISTGDKALFIDQTIDXTYNGDFIPYTYNYQPDAG
            10        20        30        40        50        60

70        80        90       100       110       120
693206  SKFSSKQIVQAGVSRALQGIFQDNFVPWMLRERDSDFEPDLQKKQWVKSLKIVQTEEDDE
        :::::::::.::::::::::::.:::::::::::::::::::::::::::::::.:::::
   -    SKFSSKQIIQAGVSRALQGVFQDNFVPWMLRERDSDFEPDLQKKQWVKSLKIIQTEEDDE
            70        80        90       100       110       120

130       140       150       160       170       180
693206  STFKPLNGEVDESYSLSLSEKGEASIKAKSSTGVLHGLETFVQLFFKHSSGTSWYTPHAP
        ::::::::::::::::::::::::::::::::::::::::::::::::::::::::::::
   -    STFKPLNGEVDESYSLSLSEKGEASIKAKSSTGVLHGLETFVQLFFKHSSGTSWYTPHAP
           130       140       150       160       170       180

190       200       210       220       230       240
693206  VSIQDEPEYPHRGILLDVARSFFEVKHIKRTIDAMSWSKLNRLHLHITDSQSWPLEIPAL
        ::::::::::::::::::::::::::::::::::::::::::::::::::::::::::::
   -    VSIQDEPEYPHRGILLDVARSFFEVKHIKRTIDAMSWSKLNRLHLHITDSQSWPLEIPAL
           190       200       210       220       230       240

693206  PKLAEKGAY
        :::::::::
   -    PKLAEKGAY
```

FIG. 4

PCR Analyses of Transgenic Lines for Stably-Integrated Transgene DNA
A. Ubi::FvGlu
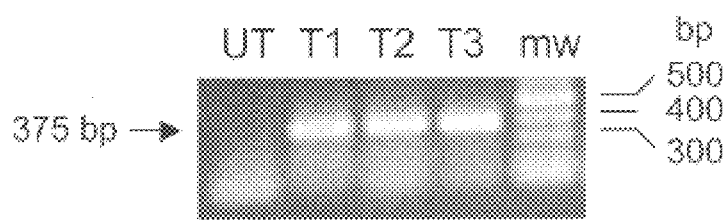
375 bp →
bp
500
400
300
B. Ubi::FvEndo
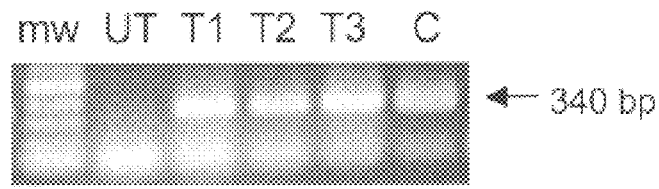
← 340 bp
C. Ubi::FvExo
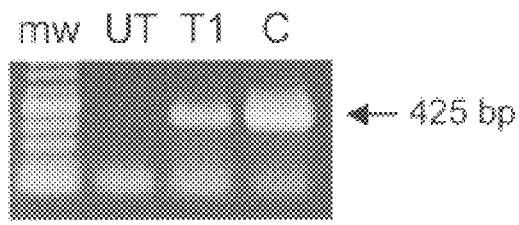
← 425 bp
Key
UT = untransformed plant
T1-T3 = transformed plants
C = plasmid (construct) control
mw = 100 bp ladder
FIG. 12

Northern Blot of FvEndo mRNA in Wheat Line AB8-108

Detection of Chitinase Transcripts Using RT-PCR
A. 5' END
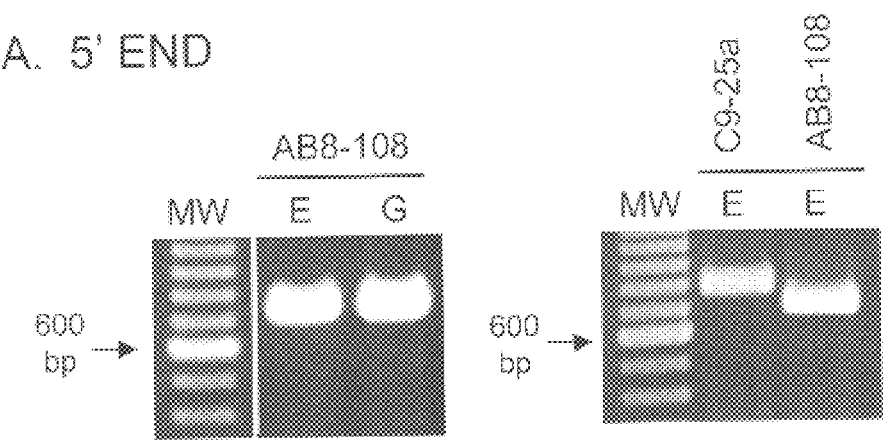
B. 3' END
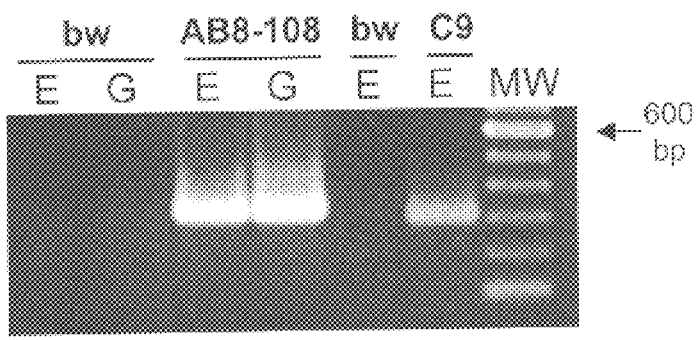
FIG. 15
Key
E = total RNA from endosperm
G = total RNA from glume
AB8-108 = endochitinase
C9-25a = exochitinase
bw = untransformed control

Authentication of Endochitinase 5' RT-PCR Product Using Restriction Endonucleases

| Endonuclease | Expected Size(s) | Size(s) Obtained |
|---|---|---|
| none | 685 bp | 660 bp |
| *SspI* | 440, 245 bp | 450, 260 bp |
| *ClaI* | 530, 155 bp | 540, 145 bp |

Authentication of Exochitinase 5' RT-PCR Product Using Restriction Endonucleases
A.
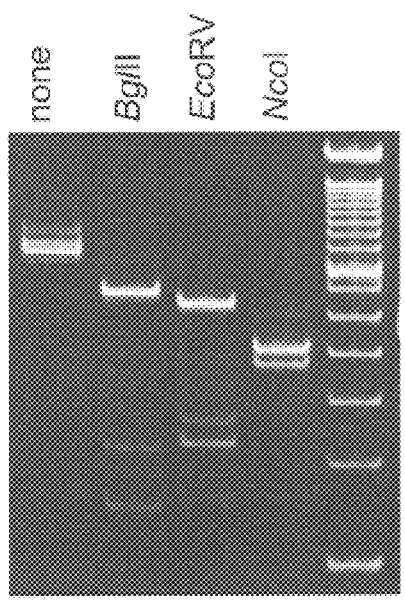
B.
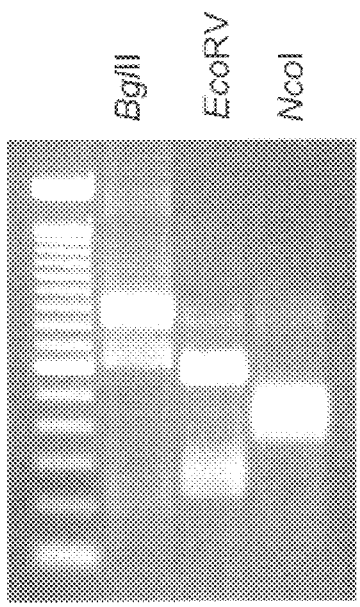
| Endonuclease | Fragment Sizes (bp) | | |
|---|---|---|---|
| | Expected | Obtained in A | Obtained in B |
| none | 795 | 700 | not tested |
| BglII | 610, 185 | 630, 225[a], 155 | 800[b], 620, 200 |
| EcoRV | 565, 230 | 560, 260[a], 225 | 580, 235 |
| NcoI | 425, 370 | 415, 370 | 430, 370 |
[a] Originating from minor PCR product in lane labeled "none"
[b] Uncleaved product resulting from incomplete digestion by BglII
FIG. 17

NUCLEIC ACID SEQUENCES ENCODING CELL WALL-DEGRADING ENZYMES AND USE TO ENGINEER RESISTANCE TO FUSARIUM AND OTHER PATHOGENS

CROSS-REFERENCE TO RELATED APPLICATIONS

This application claims the benefit of U.S. Provisional Applications Nos. 60/224,946, filed Aug. 11, 2000 and 60/151,582, filed Aug. 30, 1999. The disclosure of each of said provisional application is incorporated herein by reference in its entirety.

BACKGROUND OF THE INVENTION

1. Field of the Invention

The present invention relates to nucleic acid sequences derived from fungal genes which encode polypeptides having cell wall-degrading activity and isolated polypeptides having cell wall-degrading activity. The invention also relates to recombinant nucleic acid molecules, vectors, and host cells comprising the nucleic acid sequences as well as methods for producing and using the polypeptides, including expression in plant cells to confer or enhance a plant's resistance to Fusarium and other pathogens.

2. Description of the Art

Overview

Wheat is one of the most important food crops for both domestic and export markets. The United States produces about 2.4 billion bushels of wheat per year with a value of over 7 billion dollars. Fusarium head blight or scab is a ftngal disease of wheat, barley, oats, rye, and wheatgrasses that affects both grain yield and quality. It occurs worldwide, particularly when temperatures and humidity favor the proliferation of the causal agent, Fusarium graminearum, at the time of heading. Head blight has caused losses in the billions of dollars to United States and Canadian growers and processors within this decade. Yield and grain quality losses of wheat due to Fusarium head blight approached one billion dollars in Minnesota, North Dakota, and South Dakota in 1993 and 200–400 million dollars across the region in subsequent years. Losses were in excess of 300 million dollars in Ohio, Michigan, Indiana, and Illinois in 1995 and 1996. Quality of grain is also compromised since infected grain is usually contaminated with a mycotoxin, vomitoxin or DON, produced by the fungus that is detrimental to humans and livestock. In addition, the disease has threatened barley production in the upper Midwest because brewers have imposed zero tolerance limits for vomitoxin in grain.

The Head Blight Disease

Cereal crops, including wheat, maize, barley, oats, and rye, are susceptible to infection by many types of fungi and by many species of the pathogenic fungus Fusarium. *Fusarium graminearum* (Schwabe) and *Fusarium culmorum* are the primary causal agents of a disease known as Fusarium head blight, head blight, or scab, of wheat, barley, oats and rye (reviewed in Bai and Shaner 1994; Parry et al. 1995). The life cycle of the pathogen alternates between two hosts, wheat and maize. The teliomorph (sexual stage) of *F. graminearum*, called *Gibberella zeae*, causes stalk rot, ear rot and seedling blight of maize. Head blight is a problem of wheat and barley worldwide, and has occurred in epidemic proportions in the United States since 1991. Thus far, no effective resistance genes for Fusarium head blight have been identified in wheat, barley or their sexually-compatible relatives. Due to this deficiency, and as a consequence of no-till agriculture and unfavorable climate patterns, the wheat and barley industries in 12 states have sustained direct losses totaling 2.6 billion dollars. Increased accumulation of corn and wheat stubble has resulted from no-till agriculture and contributes to the propagation of spores and conidia in the field. Moreover, periods of rainfall and warm temperatures at the time of anthesis (pollen shed) favor germination and growth of the pathogen. *F. graminearum* causes death of the floral organs (florets) that harbor the developing grain, giving the head a bleached and "scabby" appearance, and resulting in moderate to severe reductions in grain yield. In addition, *F. graminearum* and other Fusarium species produce trichothecene mycotoxins, such as deoxynivalenol (DON), that exacerbate disease severity and pose a health threat to humans and livestock that ingest contaminated cereal products.

The marked susceptibility of the wheat head to Fusarium was noted as early as 1891 by Arthur (Parry et al. 1995). Pugh and coworkers (1933) reported that wheat heads inoculated with cultured conidia of *F. roseum* (*culmorum*) were most susceptible to infection during a 20-day window, from anthesis to the soft dough stage, depending upon the cultivar. Dehisced anthers and other degenerating tissue appeared to serve as foci for the proliferation of hyphae into the phloem and throughout the rest of the head. In histological studies, Pugh noted that hyphae usually invade intercellularly but can penetrate the thin walls of the inner parts of the floret. Although *F. graminearum* can become established on various parts of the flower, rapid spread of infection was correlated with the presence of extruded anthers both in laboratory and field studies (Andersen 1948, McKay and Loughnane 1945). Aqueous extracts of anthers were found to stimulate growth of hyphae in vitro (Strange and Smith 1971), whereas germination of macroconidia appeared to be unaffected (Strange and Smith 1978). Hyphal growth stimulation was almost entirely attributable to two quaternary ammonium compounds, glycinebetaine and its precursor choline (Strange et al. 1974). These compounds are present in other organs of the floret, but are most abundant in pollen (Pearce et al. 1976). Glycinebetaine, an osmoprotectant, accumulates over the normal course of pollen development during desiccation (reviewed in McCue and Hanson 1990). Along with choline, it is postulated to serve as a fortuitous source of carbon and nitrogen for *F. graminearum* and for other fungal pathogens. Whether fungal hyphae readily access these compounds at the pollen surface or must invade the pollen cytoplasm is not known at this time.

Identification of genes that confer resistance to Fusarium head blight is essential if wheat and barley are to remain in production in Minnesota, North Dakota, and other states. If Fusarium infection can be curtailed by even 10%, the economic impact is expected to be millions of dollars saved by producers, processors and, ultimately, consumers. Multigenic loci for resistance to scab have been identified in germplasms of wheat and other cereals, but at present, the degree of tolerance obtained in adapted cultivars through traditional breeding is inadequate for control of the pathogen. Since no-till agriculture offers clear benefits for soil and water conservation and since Fusarium is so abundant in wheat-growing regions, alternative sources for host resistance are needed.

There are no effective control measures for the disease. Resistance genes for Fusarium head blight have not been identified in wheat, barley or other sexually-compatible species, limiting the efforts of wheat breeders to develop resistant varieties. What are needed are ways to obtain crop varieties that are resistant to Fusarium head blight.

Roles of Fungal Glucanases and Chitinases

In many fungi, including species of Fusarium, glucan and chitin are principle components of the cell wall. The outer wall layer of Fusarium is comprised of polymers of glucose (1,3/1,6-β-D-glucan) with β-1,3 and β-1,6 linkages. The basal-most inner layer consists primarily of chitin microfibrils, linear polymers of β-1,4-N-acetylglucosamine that account for about one-third of the mass of the hyphal wall (Barbosa and Kemmelmeier 1993). Fusarium cell walls appear to be more refractory to the action of hydrolytic enzymes, possibly because of high levels of protein and chitin (Sivan and Chet 1989a), and clustering of acetylated glucosamine residues (Fukamizo et al. 1992).

Chitinases and glucanases are produced by naturally occurring bacteria, fungi and plants. In the fungi, these proteins have roles in the self-hydrolysis of cell wall chitin and glucan, respectively, and in the hydrolysis of cell wall components of other microorganisms (Srivastava et al. 1985; Sivan and Chet 1989b, Chérif and Benhamou 1990, Vázquez-Garciduenas et al. 1998). This latter feature has been applied to the discovery of anti-microbial biocontrol agents. Chitin is also found in the cuticles of insects and in nematode egg shells. For fungi that can utilize chitin as a carbon source, chitinase might have a role in fungal metabolism (Flach et al. 1992). Endochitinases cleave randomly between C1 and C4 linkages within the chitin polymer (Flach et al. 1992, Graham and Sticklen 1994), whereas exochitinases cleave sequentially between each linkage, releasing chitobiose from the terminus of the chitin polymer. N-acetylglucosaminidase also cleaves terminally, releasing N-acetylglucosamine (Flach et al. 1992). Likewise, endoglucanases randomly cleave β-linkages within the glucan polymer, generating short oligosaccharides, whereas the exoglucanases cleave single glucose residues from the non-reducing end of the polymer (Vázquez-Garciduenas et al. 1998). Hydrolysis of the glucan layer of fungal cell walls is attributed to the combined action of both endo- and exo-glucanases.

Glucanases and Chitinases as Antifungal Proteins

The distinctive glucan and chitin composition of the fungal cell wall has led to extensive engineering of chitinases and glucanases as antifungal proteins. Chitinases and glucanases produced by plants have been widely characterized as pathogenesis-related (Pr) proteins involved in defense against pathogens and insect pests. Pr protein genes in plants are induced upon exposure to microbial pathogens and insect pests. Cell wall-degrading proteins have been grouped into classes on the basis of their biochemical and structural properties. Both endo- and exochitinases appear to be effective in the hydrolysis of fungal cell wall chitin. Class 1 chitinases have chitinolytic activity against bacterial cell walls and are known to bind chitin directly. By contrast, the class II chitinases do not act on bacterial cell walls and lack chitin binding activity; they are postulated to play a role in production of fungal elicitors that trigger the host defense response (Graham and Sticklen 1994, Fritig et al. 1998). In general, the basic chitinases and glucanases (class I) accumulate intracellularly in the vacuole, and the acidic isoforms (class II) are extracellular, with some exceptions (e.g., Wu et al. 1994; Graham and Sticklen 1994). Comelissen and coworkers (Sela-Buurlage et al. 1993) and others (Graham and Sticklen 1994) observed that the specific activities of class I chitinases and glucanases are higher than those of the class II enzymes. Class 1 chitinases are encoded by small gene families in most plants and in the fungi. The structure of various chitinase genes and proteins has been reviewed (Graham and Sticklen 1994).

Of the five major classes of β-glucanases, only the β-1, 3-glucanases have been shown to exhibit antifungal activity (Simmons 1994). The β-1,3-glucanases are members of small multigene families in plants (Payne et al. 1990, Xu et al. 1992, Beffa and Meins 1996, Simmons 1994), but are single-copy genes in *Fusarium sporotrichioides* (FIG. 27). Class I glucanases accumulate in the vacuoles, whereas Class II and III glucanases are acidic and extracellular (see Beffa and Meins 1996). Class I glucanases have been widely studied in the context of pathogen defense and stress responses in tobacco (Linthorst et al. 1990; Linthorst 1991; Payne et al. 1990), barley (Jutidamrongphan et al. 1991; Xu et al. 1992; Malehom et al. 1993), wheat (Jutidamrongphan et al. 1991; Cruz-Ortega et al. 1997), and other species (Krishnaveni et al. 1999a, reviewed in Simmons 1994). Chitinases and glucanases act preferentially on the tips of growing fungal hypha (for instance, Broekaert et al. 1988, Collinge et al. 1993). Both chitinases and β-1,3-glucanases are differentially expressed during plant development (Lotan et al. 1989) as well as in response to pathogen attack. Glucanases appear to have roles in cell division and flower development (Beffa and Meins 1996) and the stress response (Simmons 1994) in plants. The role of chitinases in plant development is not as well-characterized; however, they have been implicated in embryogenesis and cell division (for review, see Collinge et al. 1993)

Some of the chitinases and β1,3-glucanases produced by naturally occurring bacteria and fungi have anti-Fusarium properties (Mitchell and Alexander 1961; Michael and Nelson 1972, Chérif and Benhamou 1990). Glucanases and chitinases from plants can degrade isolated cell walls of *Fusarium solani* (Mauch et al. 1988). Chitinases from tobacco were inhibitory to the growth of *F. oxysporum* (Yun et al. 1996) and *F. solani* (Sela-Buurlage et al. 1993) in culture. Krishnaveni et al. (1999b) have described three chitinases from sorghum seeds that inhibit the growth of *F. moniliforme*. The synergistic action of chitinases and glucanases against fungal pathogens is widely reported (reviewed in Graham and Sticklen 1994, Van Loon 1997). For instance, Mauch et al. (1988) observed that a chitinase and a β1,3-glucanase from pea wee active against a wide range of fungi. Melchers et al. (1994) reported the combined action of a Class V endochitinase plus a Class I β1,3-glucanase, both from tobacco, synergistically inhibited the growth of *F. solani*. Expression of a tobacco acidic chitinase with a tobacco β1,3-glucanase conferred resistance to *F. oxysporum* in tomato, whereas each protein had much less effect when expressed singly (Jongedijk et al. 1995). Likewise, the fungal pathogen *Cercospora nicotiana* was curtailed on tobacco expressing both a rice basic chitinase and an alfalfa acidic β-1,3-glucanase (Zhu et al. 1994). The synergistic action of a barley Class II chitinase and a barley Class II b-1,3-glucanase conferred protection to tobacco against *Rhizoctonia solani* (Jach et al. 1995). This chitinase in combination with a barley ribosome inactivating protein also inhibited *R. solani* infection.

Apparent Specificity of Glucanases and Chitinases

Although fungi and many, if not all, plants express glucanases and chitinases, not all of the enzymes are equally effective against all types of microorganisms (Graham and Sticklen 1994, and references therein). For example, Broekaert and co-workers (1988) observed that chitinases from thorn-apple, tobacco and wheat had antifungal activity against *Trichoderma harzianum* and *Phycomyces blakesleeanus* but not against *Botrytis cinerea*. Mauch et al. (1988) reported the differential action of a chitinase and a glucanase from pea on *Trichoderma viride* and *F. solani*, respectively. In combination, the enzymes were active against a wide range of other fungi. A tobacco chitinase with activity against Fusarium and Trichoderma were inactive against *Aspergillus flavus, Phytophthora parasitica* and other pathogens (Yun et al. (1996). The differential activities of the chitinases are attributed to inherent properties of the enzymes (Sela-Buurlage et al. 1993, Brunner et al. 1998), to differences in cell wall architecture (Sivan and Chet 1989a, Van Loon 1997) among the fungi, or to other factors.

Other Anti-Fusarium Proteins

Additional types of proteins have been found to have anti-Fusarium activity in vitro or in planta. Boyapati et al. (1994) reported a cysteine protease inhibitor from pearl millet that inhibited the growth of *Fusarium moniliforme* in culture. A cysteine-rich polypeptide from *Impatiens balsamina* seeds was active against *F. culmorum* (Tailor et al. 1997). Cecropin A, a polypeptide from the Cecropia moth, was a potent inhibitor of both *F. moniliforme* and *F. oxysporum* (deLucca et al. 1997, Cavallarin et al. 1998). Antifungal proteins from seeds of sorghum had activity against *F. moniliforme* (Seetharaman et al. 1997), and two wheat seed proteins of the PR4 family of pathogenesis-related proteins inhibited hyphal growth of *F. culmorum* and *F. graminearum* (Caruso et al. 1996). Hu and Reddy (1997) isolated a thaumatin-like protein from *Arabidopsis thaliana* with activity against *F. oxysporum*. Non-specific lipid transfer proteins from barley and maize leaves were inhibitory to *F. solani* (Molina et al., 1993). A combination of a wheat purothionin and a 2S albumin from radish or oilseed rape was effective against the growth of *F. culmorum* in vitro (Terras et al. 1993).

Microbial Genes as Anti-Fungal Transgenes in Plants

A majority of antifungal genes that have been examined both in vitro and in planta are of plant origin. To our knowledge, there are two examples of genes from fungi that exhibit antifungal activity. Endochitinases from the parasitic fungus *Trichoderma harzianum* conferred activity against *Alternaria alternata* and *B. cinerea* in transgenic tobacco, and against *A. solani* and *Rhizoctonia solani* in transgenic potato (Lorito et al. 1998). Terakawa et al. (1997) observed protection of transgenic tobacco against *Sclerotinia sclerotiorum* and *B. cinerea*, using a chitinase gene from the fungus *Rhizopus oligosporus*. A chitinase from the bacteria *Serratia marcescens* showed antifungal activity when expressed in tobacco (Suslow et al. 1988).

SUMMARY OF THE INVENTION

The present invention is directed to nucleic acid sequences derived from Fusarium fungal genes which encode polypeptides having cell wall-degrading activity as well as isolated polypeptides having cell wall-degrading activity. The invention is also directed to recombinant nucleic acid molecules, vectors, and host cells comprising the nucleic acid sequences and methods for producing and using the polypeptides, including expression in plant cells to confer or enhance a plant's resistance to Fusarium and other pathogens.

More particularly, the invention provides isolated nucleic acid molecules that encode polypeptides having cell wall-degrading activity comprising glucanase, endochitinase or exochitinase activity. Genomic sequences encoding glucanase and exochitinase and cDNA sequences encoding glucanase, endochitinase and exochitinase are specifically exemplified herein. Included within the scope of this invention are nucleic acid sequences encoding a polypeptide having the glucanase, endochitinase or exochitinase polypeptide sequences exemplified below and nucleic acid molecules encoding polypeptides having glucanase, endochitinase or exochitinase activity.

Nucleic acid sequences which hybridize specifically to an enzyme coding sequence or its complement under medium or high stringency conditions and which encode a polypeptide having glucanase, endochitinase or exochitinase activity are also encompassed by the present invention.

Nucleic acid sequences having at least 70% sequence identity with the exemplified glucanase sequences as described in detail, below, and which encode a polypeptide having glucanase activity are also encompassed by the present invention. Nucleic acid sequences encoding a polypeptide having at least 80% sequence identity with the exemplified glucanase polypeptide sequences as described in detail, below, and which encode a polypeptide having glucanase activity are also encompassed by the present invention.

Nucleic acid sequences having at least 75% sequence identity with the exemplified endochitinase or exochitinase sequences as described in detail, below, and which encode a polypeptide having endochitinase or exochitinase activity are also encompassed by the present invention. Nucleic acid sequences encoding a polypeptide having at least 85% sequence identity with the exemplified endochitinase or exochitinase polypeptide sequences as described in detail, below, and which encode a polypeptide having endochitinase or exochitinase activity are also encompassed by the present invention.

The present invention is also directed to isolated polypeptides having glucanase, endochitinase or exochitinase activity. A polypeptide having an amino acid sequence which has at least 80% sequence identity with exemplified glucanase polypeptides as described in detail, below, is encompassed by the invention. A polypeptide having an amino acid sequence which has at least 85% sequence identity with exemplified endochitinase or exochitinase polypeptides as described in detail, below, is also encompassed by the invention. Polypeptides encoded by a nucleic acid sequence which hybridizes under medium or high stringency conditions with exemplified nucleic acid sequences as discussed in detail, below, are also encompassed by the invention. Variants of the polypeptides are encompassed by the invention as well as fragments having glucanase, endochitinase or exochitinase activity.

The invention is also directed to methods of producing and using the polypeptides of the invention.

A further aspect of the invention is the provision of recombinant nucleic acid molecules containing the sequences encoding polypeptides having the fungal cell wall-degrading activity, including glucanase, endochitinase or exochitinase activity. Such molecules include, for example, recombinant vectors, such as cloning, expression or transformation vectors, which contain a DNA sequence encoding a glucanase, endochitinase or exochitinase.

Another aspect of the invention is the provision of cells which are transformed by the above vectors or DNA sequences.

A particular use of the invention is the provision of cells transformed with one or more nucleic acid sequences of the invention. A more particular use of the invention is the provision of plants, plant seeds or plant cells transformed with one or more nucleic acid sequences encoding a polypeptide having glucanase, endochitinase or exochitinase coding activity to provide plants having resistance to plant pathogens, including fungi, particularly, Fusarium species or to provide plants having enhanced resistance to plant pathogens.

A further aspect of the invention is the provision of oligonucleotide probes capable of detecting a glucanase, endochitinase or exochitinase gene or functional equivalents thereof in fungi of the genus Fusarium and the use of the probes to isolate nucleic acid sequences encoding a glucanase, endochitinase or exochitinase gene or functional equivalent thereof. The nucleic acid sequences which specifically hybridize to the probes and which encode a functional glucanase, endochitinase or exochitinase are encompassed by the present invention.

Using the nucleic acid sequences of the invention facilitates the isolation of homologous genes from fungi to obtain genes which protect host cells, including fungi, bacteria, and plants against related fungal pathogens.

The invention also includes the application of transgene constructs in combination with each other, that is, glucanase and endochitinase; glucanase and exochitinase; endochitinase and exochitinase; and glucanase, endochitinase and exochitinase. Also included are transgenic monocot or dicot lines, plant cells, and progeny obtained by sexual or asexual propagation, that carry any combination of the transgene constructs.

In accordance with this discovery, it is an object of the invention to provide nucleic acid sequences encoding fungal cell wall-degrading enzymes selected from the group consisting of glucanase, exochitinase, and endochitinase; isolated polypeptides having glucanase, endochitinase or exochitinase activity; recombinant nucleic acid molecules including expression vectors encoding polypeptides having cell wall-degrading activity; and cells harboring the recombinant nucleic acid molecules or expression vectors.

It is also an object of the invention to provide transformation vectors comprising a cell wall-degrading recombinant molecule, which vectors are effective for stably introducing the recombinant molecule into a plant.

It is also an object of the invention to provide methods of producing and using polypeptides having glucanase, endochitinase or exochitinase activity.

It is another object of the invention to provide transgenic plants having bacterial or fungal resistance, wherein the resistance is a result of expression of a recombinant nucleic acid molecule of the invention.

A further object of the invention is to provide fungal genes which generate cell wall-degrading enzymes, including proteins having the capability of degrading the glucan and chitin cell wall components of *F. venenatum* and other Fusarium species, including *F. graminearum* and *F. culmorum*, the principle causal agents of head blight (scab) in the U.S.

Another object of the invention is expression of the cell wall-degrading enzymes in transgenic monocots, including wheat, barley or oats, to confer partial or complete resistance to Fusarium species and/or to other fungal pathogens of wheat and other cereal crops. Such transgenic lines will be useful genetic stocks for generating improved crops.

A still further object of the invention is the provision of novel wheat germplasms that express genes designed to limit the spread of the pathogenic fungus Fusarium and indirectly to curtail the accumulation of DON in infected heads.

Other objects and advantages of the invention will become readily apparent from the ensuing description.

BRIEF DESCRIPTION OF THE DRAWINGS

FIG. 1 is a comparison of glucanases encoded by *F. venenatum* cDNA (upper) and *F. sporotrichioides* genomic DNA (lower) (SEQ ID NOS:5 and 4, respectively).

FIG. 2 shows the *F. venenatum* endochitinase 5' cDNA PCR product and the deduced polypeptide sequence (SEQ ID NOS:6 and 7, respectively). Bold type indicates new sequence obtained in 5' PCR product. Non-bold type shows the portion of the *F. venenatum* endochitinase 5' cDNA sequence that matches the *F. venenatum* endochitinase partial cDNA sequence.

FIG. 3 shows the *F. sporotrichioides* exochitinase 5' genomic PCR product and a portion of the deduced polypeptide sequence (SEQ ID NOS:8 and 9, respectively). The underlined segment indicates an intron. The nucleotide segment before the ATG (first M) is the promoter and 5' untranslated region. Bold type indicates new sequence obtained in 5' PCR product. Non-bold type shows the portion of the *F. sporotrichioides* genomic sequence that matches the *F. venenatum* exochitinase cDNA sequence.

FIG. 4 shows the comparison of exochitinases encoded by *F. venenatum* cDNA (upper) and *F. sporotrichioides* genomic DNA (lower) (SEQ ID NOS: 14 and 15, respectively).

FIG. 5 illustrates the modification to the Ubiquitin-1 promoter.

FIG. 6 shows the map of plasmid FvGluS; monocot expression vector having the modified full-length glucanase cDNA in the sense orientation.

FIG. 7 shows the map of plasmid FvGluAS; monocot expression vector having the modified full-length glucanase cDNA in the antisense orientation.

FIG. 8 shows the map of plasmid FvEndoS; monocot expression vector having the modified full-length endochitinase cDNA in the sense orientation.

FIG. 9 shows the map of plasmid FvEndoAS; monocot expression vector having the modified full-length endochitinase cDNA in the antisense orientation.

FIG. 10 shows the map of plasmid FvExoS; monocot expression vector having the modified full-length exochitinase cDNA in the sense orientation.

FIG. 11 shows the map of plasmid FvExoAS; monocot expression vector having the modified full-length exochitinase cDNA in the antisense orientation.

FIG. 12 shows the PCR analyses of transgenic lines for stably integrated transgene DNA. UT indicates untransformed plant; T1–T3 indicates transformed plants; C indicates plasmid (construct) control; mw indicates 100 bp ladder.

FIG. 13 shows the Northern blot of FvEndo mRNA in *Triticum aestivum* line AB8–108.

FIG. 14 shows detection of 5 ' portion of glucanase transcripts in endosperm and glume of *Triticum aestivum* using RT-PCR.

FIG. 15 shows detection of 5' and 3' portions of endo- and exo-chitinase transcripts in endosperm and glume of *Triticum aestivum* using RT-PCR.

FIG. 16 shows authentication of endochitinase 5' RT-PCR product using restriction endonucleases.

FIG. 17 shows authentication of exochitinase 5' RT-PCR product using restriction exonucleases.

BRIEF DESCRIPTION OF THE SEQUENCES

SEQ ID NO:1 is a *F. venenatum* glucanase full-length unmodified cDNA sequence.

SEQ ID NO:2 is the glucanase encoded by SEQ ID NO:1.

SEQ ID NO:3 is the genomic DNA segment containing the *F. sporotrichioides* glucanase gene.

SEQ ID NO:4 is the glucanase sequence encoded by SEQ ID. NO:3.

SEQ ID NO:5 is a glucanase encoded by a *F. venenatum* cDNA sequence.

SEQ ID NO:6 is a *F. venenatum* endochitinase 5' cDNA PCR product.

SEQ ID NO:7 is the polypeptide encoded by SEQ ID NO:6.

SEQ ID NO:8 is a *F. sporotrichioides* exochitinase 5' genomic PCR product.

SEQ ID NO:9 is a portion of the polypeptide sequence encoded by SEQ ID NO:8.

SEQ ID NO:10 is a *F. venenatum* endochitinase unmodified full-length cDNA sequence.

SEQ ID NO:11 is the endochitinase encoded by SEQ ID NO:10.

SEQ ID NO:12 is a *F. sporotrichioides-F. venenatum* chimeric sequence.

SEQ ID NO:13 is the exochitinase encoded by SEQ ID NO:12.

SEQ ID NO:14 comprises amino acids 1 to 249 of an exochitinase encoded by a *F. venenatum* cDNA.

SEQ ID NO:15 comprises amino acids 1 to 249 of a *F. sporotrichioides* genomic DNA.

SEQ ID NO:16 is a *F. venenatum* glucanase modified full-length CDNA sequence.

SEQ ID NO:17 is the glucanase encoded by SEQ ID NO:16.

SEQ ID NO:18 is a *F. venenatum* endochitinase modified full-length cDNA sequence.

SEQ ID NO:19 is the endochitinase encoded by SEQ ID NO:18.

SEQ ID NO:20 is a *F. venenatum* exochitinase modified full-length cDNA sequence.

SEQ ID NO:21 is the exochitinase encoded by SEQ ID NO:20.

Figure 5:
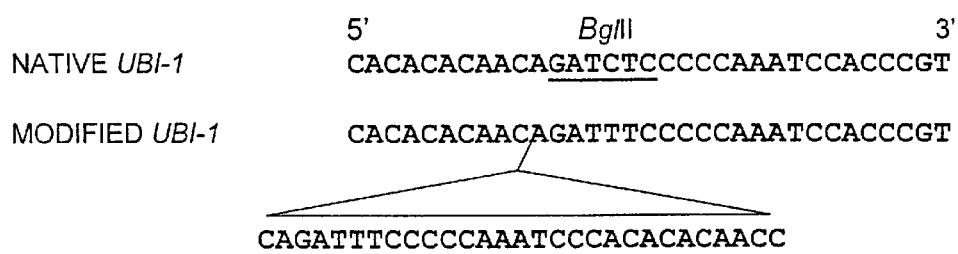

SEQ ID NOS:22–24 are the native Ubiquitin-1 and modified Ubiquitin-1 sequences shown in FIG. 5 (upper, middle, and lower, respectively).

SEQ ID NO:25 is a leader sequence.

SEQ ID NO:26 is primer Ml3F.

SEQ ID NO:27 is primer MI 3R.

SEQ ID NOS:28–74 are the primers shown in Table 2.

SEQ ID NOS:75–82 are the PCR primers shown in Table 3.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., Rieger, R., et al.(eds.), Springer Verlag (1991); and Hale & Marham, THE HARPER COLLINS DICTIONARY OF BIOLOGY (1991).

To facilitate understanding of the invention, a number of terms are defined below.

"Glucanase" refers to a protein or polypeptide with hydrolytic activity on glucan, a component of fungal cell walls. In particular, glucanase refers to a polypeptide having the enzymatic ability to degrade the β-1,3 linkages of glucan.

The term "glucanase activity" is defined herein as hydrolytic activity which catalyzes the degradation of the β-1,3 linkages of glucan. Glucanase activity can be measured by adding a suitable substrate (e.g., glucan, laminarin) to a cellular extract, e.g., wheat endosperm tissue, leaf tissue, according to published methods. Assays are described in Keen and Yoshikawa (1983) and Fontaine et al. (1997).

"Chitinase" refers to a protein or polypeptide with hydrolytic activity on chitin, a macromolecule composed primarily of N-acetyl-glucosamine and found in cell walls of fungal hyphae and spores.

"Endochitinase" refers to a protein or polypeptide that enzymatically degrades chitin by cleaving randomly between C1 and C4 linkage with the chitin polymer.

The term "endochitinase activity" is defined herein to mean the ability to degrade chitin by cleaving randomly between C1 and C4 linkage with the chitin polymer.

"Exochitinase" refers to a protein or polypeptide that enzymatically degrades chitin by cleaving sequentially between each C1 and C4 linkages from the terminus of the chitin polymer.

The term "exochitinase activity" is defined herein to mean ability to degrade chitin by cleaving sequentially between each C1 and C4 linkages from the terminus of the chitin polymer.

Chitinase (endochitinase or exochitinase) activity can be measured by adding a suitable substrate to a cellular extract, e.g., wheat endosperm tissue, leaf tissue, according to published methods. Assays are described in Harman et al. (1993); McCreath and Gooday (1992); Tronsmo and Harman (1993), Bolar et al. (2000), and U.S. Pat. No. 5,378,821.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be a "native DNA sequence," or a "heterologous DNA sequence" (i.e., "foreign DNA"). The term "native DNA sequence" refers to a nucleotide sequence which is naturally found in the cell into which it is introduced so long as it does not contain some modification (e.g., a point mutation, the presence of a selectable marker gene, etc.) relative to the naturally-occurring sequence.

The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes a native DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "transformation" as used herein refers to the introduction of a transgene into a cell. Transformation of a cell may be stable or transient.

The term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Stable transformation of a plant may also be detected by using the polymerase chain reaction to amplify transgene sequences from genomic DNA from cells of the progeny of that plant. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "isolated" when used in relation to a nucleic acid molecule, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Fusarium, or another or related organism and thus, for example, may be an allelic or species variant of the polypeptide encoding region of the nucleic acid sequence.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least about 20% pure, preferably at least about 40% pure, more preferably at least about 60% pure, even more preferably at least about 80% pure, and most preferably at least about 90% or 95% pure. Purity may be determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The term "identity," as known in the art, is a relationship between two or more polypeptide sequences or two or more polynucleotide sequences, as determined by a comparison of the sequences. In the art, "identity" also means the degree of sequence relatedness between polypeptide or polynucleotide sequences, as determined by the match between strings of such sequences. "Identity" can be readily calculated by known methods, including but not limited to those described in Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; and Sequence Analysis in Molecular Biology, von Heinje, G., Academic Press, 1987. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990) and Altschul et al., Gapped BLAST and PSI-BLAST: a new generation of protein database search programs. Nucleic Acids Res. 25: 3389–3402 (1997).), ALIGN (http://dot.imgen.bcm.tmc.edu:9331/seq-search/alignment.html), and ClustalW (http://dot.imgen.bcm.edu:9331/cgi-bin/multi-align/multi-align.pl) (Higgens, 1989).

"Percentage of sequence identity" is determined by comparing two optimally aligned sequences over a comparison window, wherein the portion of the polynucleotide sequence or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. It is preferred that the comparison window is at least 50% of the coding sequence, preferably 60%, more preferably 75% or 85%, and even more preferably 95% to 100%.

The term "hybridization" as used herein includes "any process by which a strand of nucleic acid joins with a complementary strand through base pairing."[Coombs J (1994) *Dictionary of Biotechnology*, Stockton Press, New York N.Y.]. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

The phrase "hybridizes under stringent conditions" refers to the formation of a double-stranded duplex from two single-stranded nucleic acids. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid.

Nucleic acid probes to identify and clone DNA encoding polypeptides having the desired enzyme activity from strains of different genera or species can be prepared according to methods well known in the art. Such probes can be used for hybridization with the genomic or cDNA of the genus or species of interest, following standard Southern blotting procedures, in order to identify and isolate the corresponding gene therein. Both DNA and RNA probes can be used. The probes are typically labeled for detecting the corresponding gene (for example, with $^{32}P$, $^{3}H$, $^{35}S$, biotin, or avidin).

For long probes of at least 100 nucleotides in length, high or medium stringency conditions are used. High stringency conditions when used in reference to nucleic acid hybridization comprise conditions equivalent to binding or hybridization at 68° C. in a solution consisting of 5×SSPE, 1% SDS, 5×Denhardt's reagent and 100 µg/ml denatured salmon sperm DNA followed by washing in a solution comprising 0.1×SSPE, and 0.1% SDS at 68° C. when a probe of about 100 to about 1000 nucleotides in length is employed, or the above-mentioned conditions with 50% formamide at 42° C. High stringency washes can include 0×SSC to 0.2×SSC, 1% SDS, 65° C., 15–20 min. An example of stringent wash conditions for a Southern blot of such nucleic acids is a 0.2×SSC wash at 65° C. for 15 minutes (see, Sambrook et al., Molecular Cloning—A Laboratory Manual ($2^{nd}$ ed.) Vol. 1–3, Cold Spring Harbor Laboratory, Cold Spring Harbor Press, NY, 1989, for a description of SSC buffer). Other exemplary high stringency hybridization conditions include, for example, 7% SDS, 0.25 M sodium phosphate buffer, pH 7.0–7.2, 0.25 M sodium chloride at 65° C.–68° C. or the above-mentioned conditions with 50% formamide at 42° C. Exemplary medium stringency conditions are as described above for high stringency except that 35% formamide at 42° C. is used, and the washes are carried out at 55° C.

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the material with immobilized DNA is washed once in 6×SCC plus 0.1% SDS for 15 minutes and twice each for 15 minutes using 6×SSC at 5° C. to 10° C. below the calculated $T_m$.

A genomic DNA or cDNA library prepared from other organisms may be screened for DNA which hybridizes with the probes described above and which encodes a polypeptide having the desired enzyme activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable material. In order to identify a clone or DNA which is homologous with a selected sequence or a subsequence thereof, the material with immobilized DNA is used in a Southern blot. For purposes of the present invention, hybridization indicates that the nucleic acid sequence hybridizes to a labeled nucleic acid probe corresponding to the selected nucleic acid sequence, its complementary strand, or a subsequence thereof, under medium to high stringency conditions. Molecules to which the nucleic acid probe hybridizes under these conditions are detected using X-ray film.

The term "nucleic acid construct" refers to a nucleic acid molecule, either single- or double-stranded, which is isolated from a naturally occurring gene or which has been modified to contain segments of nucleic acid which are combined and juxtaposed in a manner which would not otherwise exist in nature. The nucleic acid construct can include, for example, a coding sequence of the invention, and control sequences such as a promoter, and transcriptional and translation stop signals. The term nucleic acid construct is synonymous with the term expression cassette when the nucleic acid construct contains all the control sequences required for expression of a coding sequence of the present invention. Exemplary constructs include plasmids and vectors, including cloning vectors, recombinant expression vectors. A "vector" is a nucleic acid composition which can transduce, transform or infect a cell and generally be replicated in the cell, thereby causing the cell to express vector-encoded nucleic acids and, optionally, proteins other than those native to the cell, or in a manner not native to the cell. A vector includes a nucleic acid (ordinarily RNA or DNA) to be expressed by the cell. A vector optionally includes materials to aid in achieving entry of the nucleic acid into the cell, such as a retroviral particle, liposome, protein coating or the like. Vectors contain nucleic acid sequences which allow their propagation and selection in bacteria or other non-plant organisms. For a description of vectors and molecular biology techniques, see CURRENT PROTOCOLS IN MOLECULAR BIOLOGY, Ausubel, et al., (eds.), Current Protocols, a joint venture between Greene Publishing Associates, Inc. and John Wiley & Sons, Inc., (through and including the 1998 Supplement) (Ausubel).

The term "coding sequence" is defined herein as a nucleic acid sequence which directly specifies the amino acid sequence of its protein product, e.g., a sequence which is transcribed into mRNA and translated into a polypeptide. The boundaries of the coding sequence are generally determined by the ATG start codon (eukaryotes) and a translation terminator (stop codon). A coding sequence can include, but is not limited to, DNA, cDNA, and recombinant nucleic acid sequences.

The term "sense orientation" refers to the orientation of a cDNA sequence or coding sequence with respect to the promoter in a construct, such that the 5' end of the cDNA sequence or coding sequence is adjoined to the promoter. The term "antisense" (or reverse) refers to the orientation of a nucleic acid sequence such as the cDNA or coding sequence with respect to the promoter in a construct, such that the 3' end of the sequence is adjoined to the promoter.

The term "control sequences" is defined to include all components which are necessary or advantageous for the expression of a polypeptide. Such control sequences include, but are not limited to, a leader, a polypeptide sequence, a promoter, a signal peptide sequence or a targeting sequence, an enhancer, and a transcription terminator. At a minimum, the control sequences include a promoter, and a transcriptional terminator sequence. The portion of a gene or nucleic acid construct containing the 5' leader sequence, generally 5 to 15 nucleotides in length immediately upstream of the ATG start codon, can also be considered a control sequence as it can affect the efficiency of translation. The control sequences may be provided with linkers for the purpose of introducing specific restriction sites facilitating ligation of the control sequences with the coding region of the nucleic acid sequence encoding a polypeptide. The term "operably linked" is defined here as a configuration in which a control sequence is placed at a position relative to the coding sequence of the nucleic acid sequence such that the control sequence directs the production of a messenger RNA and/or a polypeptide.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. A DNA sequence is "operatively associated" with the promoter in a cell when RNA polymerase which binds the promoter sequence transcribes the coding sequence into MnRNA which is then in turn translated into the protein encoded by the coding sequence.

The control sequence may also be a suitable transcription terminator sequence, a sequence recognized by a host cell to terminate transcription. The terminator sequence is operably linked to the 3' terminus of the nucleic acid sequence encoding the polypeptide.

The control sequence may also be a suitable leader sequence, a nontranslated region of an mRNA which is important for translation by the host cell. The leader sequence is operably linked to the 5' terminus of the nucleic acid sequence encoding the polypeptide.

The control sequence may also be a polyadenylation sequence, a sequence operably linked to the 3' terminus of the nucleic acid sequence and which, when transcribed, is recognized by the host cell as a signal to add polyadenosine residues to transcribed mRNA.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide.

The control sequence may also be a localization peptide that codes for an amino acid sequence linked to the carboxy terminus of a polypeptide and directs the encoded polypeptide to specific locations in a cell.

Antisense technology comprises cloning a nucleic acid segment and operatively linking it to a promoter such that the antisense (or complementary) strand of RNA will be transcribed. The construct is then transformed into the host cell and the antisense strand of RNA is produced.

The term "expression vector" refers to a vector comprising a nucleic acid construct and sequences for delivery into and autonomous replication in microbial host cells. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, subcellular localization or the like. The variant sequence may be constructed on the basis of the nucleic acid sequence presented as the polypeptide encoding part of an exemplified sequence, a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for enzyme activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS* Letters 309: 59–64).

The term "host cell" is a cell which has been transformed or transfected, or is capable of transformation or transfection by an exogenous polynucleotide sequence. The host cell may be a unicellular microorganism, e.g., a prokaryote, or a non-unicellular microorganism, e.g., a eukaryote. Eukaryote cells can include any cell such as from an insect, fungus or plant. Exemplary host cells, introduction of a vector into a host cell, and cloning are described in U.S. Pat. No. 5,374,540 which is hereby incorporated by reference.

Plant host cells include but are not limited to, somatic cells, gametes or embryos. "Embryo" refers to a sporophytic plant before the start of germination. Embryos can be formed by fertilization of gametes by sexual crossing or by selfing. A "sexual cross" is pollination of one plant by another. "Selfing" is the production of seed by self-pollenization, i.e., pollen and ovule are from the same plant. The term "backcrossing" refers to crossing a F. hybrid plant to one of its parents. Typically, backcrossing is used to transfer genes which confer a simply inherited, highly heritable trait into an inbred line. The inbred line is termed the recurrent parent. The source of the desired trait is the donor parent. After the donor and the recurrent parents have been sexually crossed, F, hybrid plants which possess the desired trait of the donor parent are selected and repeatedly crossed (i.e., backcrossed) to the recurrent parent or inbred line.

Embryos can also be formed by "embryo somatogenesis" and "cloning." Somatic embryogenesis is the direct or indirect production of embryos from cells, tissues and organs of plants. Indirect somatic embryogenesis is characterized by growth of a callus and the formation of embryos on the surface of the callus. Direct somatic embryogenesis is the formation of an asexual embryo from a single cell or group of cells on an explant tissue without an intervening callus phase. Because abnormal plants tend to be derived from a callus, direct somatic embryogenesis is preferred.

The term "plant" as used herein refers to a plurality of plant cells which are largely differentiated into a structure that is present at any stage of a plant's development. Such structures include, but are not limited to, whole plants, plant parts or organs, e.g., callus, root, fruit, seed, shoot, stem, tuber, leaf, floret organs including glume, lemma, palea, tapetum, and pollen, and progeny of same. Plant progeny includes progeny of plants, plant parts and plant cells. The class of plants which can be used in the methods of the invention is generally as broad as the class of higher plants amenable to transformation techniques, including both monocotyledonous (a monocot) and dicotyledonous (a dicot) plants.

The term "progeny" refers to the descendants of a particular plant or regenerant (self-cross) or pair of plants (crossed or backcrossed). The descendants by self-fertilization can be of the $T_1$, the $T_2$, or any subsequent generation, and descendants by crossing can be of the $F_1$, the $F_2$, or any subsequent generation. Typically, the parents are the pollen donor and the ovule donor which are crossed to make the progeny plant of this invention. Parents also refer to $F_1$ parents of a hybrid plant of this invention (the $F_2$ plants). Finally, parents refer to a recurrent parent which is backcrossed to hybrid plants of this invention to produce another hybrid plant of this invention.

The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, etc.). Plant tissue may be in planta, in organ culture, tissue culture, or cell culture.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

"Transgenic plants" are plants into which a nucleic acid sequence has been introduced through recombinant techniques, i.e., nucleic acid-containing vectors, cloning, somatic embryogenesis or any other technique used by those of skill to produce plants.

"Line" pertains to a plant or its germplasm, a primary regenerant from transformation, $(T_0)$ plant or its progeny, resulting from genetic transformation, in which all or a portion of transgene has been stably integrated.

The term "monocot" refers to a plant species having a single cotyledon, including wheat, oat, barley, rice, rye, triticale, maize (corn), and other cereals, as well as sugarcane, sorghum, pineapple, yam, onion, banana, coconut, date, hops, and grasses such as meadow grass and forage grass.

The common names of cereal crop plants used throughout this disclosure refer to varieties of plants of the following genera:

| Common Name | General |
| --- | --- |
| Wheat (soft, hard and durum varieties) | Triticum |
| Sorghum | Sorghum |
| Rice | Oryza |
| Barley | Hordeum |
| Maize or corn | Zea |
| Rye | Secale |
| Triticale | Triticale |
| Oat | Avena |

Dicotyledonous refers to plant species characterized by a pair of embryonic seed leaves that appear at germination, including tobacco, potato, tomato, soybean, pea, bean, sugar beet, papaya, Cucurbita (squash, cucumber, melon, pumpkin, zucchini), stone fruit trees, cotton, sweet potato, cruciferous plants (family Brassicaceae), such as cauliflower, rape seed, and the closely related model organism *Arabidopsis thaliana*.

Other plants susceptible to fungal or bacterial diseases are also encompassed, including, for example, grapes, coca beans, and nuts.

"EST" refers to Expressed sequence tag; nucleotide sequence of a complete or partial cDNA, representing a transcript or messenger RNA that is expressed in an organ, tissue or cell type; usually 100 or more nucleotides in length.

DETAILED DESCRIPTION OF THE INVENTION

I. Fungal Cell Wall-Degrading Enzymes and Nucleic Acid Molecules Encoding the Enzymes The present invention is directed to isolated nucleic acid sequences derived from Fusarium fungal genes which encode polypeptides having cell wall-degrading activity comprising glucanase, endochitinase or exochitinase activity as well as isolated polypeptides having cell wall-degrading activity.

A1. Nucleic Acid Molecules Which Encode Glucanase Activity

Glucanase refers to a polypeptide having the ability to degrade the β-1,3 linkages of glucan. In a first embodiment, the present invention is directed to isolated nucleic acid molecules which encode a polypeptide having glucanase activity, selected from the group consisting of:

(a) a nucleic acid sequence having at least 70% nucleotide sequence identity with SEQ ID NO:1 from nucleotide 37 through nucleotide 942, SEQ ID NO:3 from nucleotide 1801 through nucleotide 2761 or SEQ ID NO:16 from nucleotide 18 to nucleotide 923;

(b) a nucleic acid sequence encoding a polypeptide having an amino acid sequence which has at least 80% identity with amino acids 1 to 301 of SEQ ID NO:2, 4, 5 or 17;

(c) a nucleic acid sequence which hybridizes under medium or high stringency conditions with (i) SEQ ID NO:1 from nucleotide 37 through nucleotide 942, SEQ ID NO:3 from nucleotide 1801 through nucleotide 2761 or SEQ ID NO:16 from nucleotide 18 to nucleotide 923; (ii) a subsequence of (i) of at least 100 contiguous nucleotides, or (iii) a complementary strand of (i) or (ii); and (d) a subsequence of (a), (b) or (c) wherein the subsequence encodes a polypeptide fragment which has glucanase activity.

The isolated nucleic acid molecules which encode a polypeptide having glucanase activity include genomic sequences which encode a glucanase and which direct and regulate the transcriptional and translational expression of the glucanase coding sequences, and cDNA sequences which encode a polypeptide having glucanase activity.

Specific embodiments of nucleotide sequences which encode polypeptides having glucanase activity are given in SEQ ID NOS:1, 3, and 16. An exemplified glucanase gene product has a predicted amino acid sequence as given in SEQ ID NOS:2, 4, 5, and 17. A genomic DNA sequence containing the full-length glucanase gene is presented in SEQ ID NO:3. The genomic DNA sequence is 3622 bp in length, and nucleotide sequence analysis reveals 2 exons and 1 intron. The coding region comprises nucleotide 1801 to 2014 and 2070 to 2761 which encodes a protein 301 amino acids in length (SEQ ID NO:4). A *F. venenatum* glucanase full-length unmodified cDNA sequence is given in SEQ ID NO:1. The cDNA sequence is 1023 bp in length. The resulting open reading frame (coding portion), initiating at base 37 and terminating at base 942 encodes a protein 301 amino acids in length (SEQ ID NO:2). A *F. venenatum* modified full length cDNA sequence which encodes a glucanase is given in SEQ ID NO:16. This cDNA is 932 bp in length. The open reading frame initiating at base 18 and terminating at base 923 encodes a protein of 301 amino acids (SEQ ID NO:17). One modification made to the unmodified glucanase sequence is the substitution of a CA-rich 5' leader sequence, GGATCCACCAACCAGCG, (bases #1–#17 of GLUC 5' primer, Table 2). The modified 5' leader sequence occurs immediately upstream of the ATG start codon of the glucanase coding sequence. The modification renders the leader sequence rich in C and A nucleotides, and minimizes the number of T nucleotides. These characteristics are reported to enhance the translational efficiency of genes in plants. SEQ ID NO:5 shows a glucanase having 301 amino acids which is encoded by a *F. venenatum* cDNA.

In another embodiment, the nucleic acid molecule is the sequence contained in plasmid GLU2 (SEQ ID NO:16 which is a *F. venenatum* glucanase modified full-length cDNA sequence) that is contained in *Escherichia coli* NRRL B-30201.

In another embodiment, the nucleic acid molecule is the sequence contained in plasmids FvGluS or FvGluAS that are contained in *Escherichia coli* NRRL B-30204 and NRRL B-30205, respectively.

The invention also encompasses nucleic acid sequences which have a degree of sequence identity to the coding region of SEQ ID NO:1, 3 or 16 or coding region plus intron of SEQ ID NO:3 of at least 70%, preferably at least about 75%, preferably at least about 80%, more preferably at least about 85%, more preferably at least about 90%, and even more preferably about 95% and which encode a polypeptide effective to degrade β-1,3-linkages of glucan. For purposes of the present invention, the degree of identity between two nucleic acid sequences is determined by the Clustal method (Thompson et al. 1994), using ClustalW 1.7 or 1.8 (http://dot.imzen.bcm.tmc.edu:9331/multi-align/multi-align.html) with the following pairwise alignment parameters: K-tuple=2; gap penalty=5; window size=4; diagonals—4. Multiple alignment parameters were: gap opening penalty=10; gap extension penalty=5.

Further, nucleic acid sequences which hybridize under medium stringency or high stringency conditions, as defined above, with the coding region of the DNA sequence of SEQ ID NO:1, 3 or 16 or coding region plus intron of SEQ ID NO:3 and which encode a polypeptide effective to degrade β-1,3-linkages of glucan are included in the present invention.

Also encompassed by the invention are subsequences of at least 100 contiguous nucleotides and preferably at least 200 contiguous nucleotides which hybridize under medium stringency or high stringency conditions, as defined above, with the coding region of the DNA sequence of SEQ ID NO:1, 3 or 16 or coding region plus intron of SEQ ID NO:3.

The invention further encompasses a complementary strand of a nucleic acid sequence or subsequence of at least 100 contiguous nucleotides and preferably at least 200 contiguous nucleotides of a nucleic acid sequence which hybridizes under medium stringency or high stringency conditions, as defined above, with the coding region of the DNA sequence of SEQ ID NO:1, 3 or 16 or coding region plus intron of SEQ ID NO:3.

The invention is further directed to a subsequence of the aforenamed nucleic acid sequences wherein the subsequence encodes a polypeptide fragment which has glucanase activity.

A2. Polypeptides Having Glucanase Activity

The present invention is also directed to isolated polypeptides having glucanase activity which are encoded by the nucleic acid molecules described above. Isolated polypeptides having glucanase activity comprise:

(a) a polypeptide having an amino acid sequence which has at least 80% identity with amino acids 1 to 301 of SEQ ID NO:2, 4, 5 or 17;

(b) a polypeptide encoded by a nucleic acid sequence which hybridizes under medium stringency or high stringency conditions with (i) SEQ ID NO:1 from nucleotide 37 through nucleotide 942, SEQ ID NO:3 from nucleotide 1801 through nucleotide 2761 or SEQ ID NO:16 from nucleotide 18 to nucleotide 923; (ii) a subsequence of (i) of at least 100 nucleotides, or (iii) a complementary strand of (i) or (ii); and (c) a fragment of (a), or (b) that has glucanase activity.

FIG. 1 is a comparison of full-length glucanases encoded by *F. venenatum* cDNA (upper) and *F. sporotrichioides* genomic DNA (lower) (SEQ ID NOS:5 and 4, respectively).

Isolated nucleic acid sequences encoding polypeptides comprising an amino acid sequence which has a degree of identity to the amino acid sequence of SEQ ID NO:2, 4, 5 or 17 with amino acids 1 to 301 of at least about 80%, preferably at least 85%, more preferably at least about 90%, further more preferably at least about 95%, and most preferably at least about 97%, and which have glucanase activity (homologous polypeptides), are encompassed by the invention. For purposes of the present invention, the degree of identity between two amino acids is determined by the FASTA/FASTP method of Pearson (1990), using ALIGN (http://dot.imgen.bcm.tmc.edu:9331/seq-search/alignment.html), with the BLOSUM50 or PAM250 scoring matrix and the following pairwise alignment parameters: gap penalty=−12 for the first residue in the gap, and −2 for additional residues; K-tuple=2. Multiple alignments are carried out with the BLOSUM matrix, using the ClustalW 1.7 algorithm (Thompson et al. 1994). Multiple alignment parameters are: gap opening penalty=10, gap extension penalty=0.05; hydrophilic gap penalties on (hydrophilic residues GPSNDQERK); with residue-specific gap penalties.

Preferably, the polypeptides of the present invention comprise an amino acid sequence of SEQ ID NO:2, 4, 5 or 17 or a fragment thereof that has glucanase activity. In another preferred embodiment, the polypeptide of the present invention comprises amino acids 1 to 301 of SEQ ID NO:2, 4, 5 or 17 or a fragment thereof that has glucanase activity.

A fragment of SEQ ID NO:2, 4, 5 or 17 is a polypeptide having one or more amino acids deleted from the amino and/or carboxyl terminus of this amino acid sequence. Preferably, a fragment contains at least 256 amino acid residues, more preferably at least 271 amino acid residues, and most preferably at least 286 amino acid residues.

The present invention relates to isolated polypeptides having glucanase activity which are encoded by nucleic acid sequences which hybridize under medium stringency conditions or high stringency conditions, as described in detail above, with (i) SEQ ID NO:1 from nucleotide 37 through nucleotide 942, SEQ ID NO:3 from nucleotide 1801 through nucleotide 2761 or SEQ ID NO:16 from nucleotide 18 to nucleotide 923; (ii) a subsequence of (i) of at least 100 nucleotides, or (iii) a complementary strand of (i) or (ii). The subsequence of SEQ ID NO:1, 3 or 16 may be at least 100 contiguous nucleotides or preferably at least 200 contiguous nucleotides. Moreover, the subsequence may encode a polypeptide fragment which has glucanase activity.

The degeneracy of the genetic code is well known to the art; therefore, synonymous coding sequences with one or more codon substitutions can be readily determined by one of ordinary skill in the art. Synonymous coding sequences vary from the exemplified coding sequences but encode proteins of the same amino acid sequences as those specifically provided herein.

Examples of conservative substitutions are within the groups of basic amino acids (such as arginine, lysine and histidine), acidic amino acids (such as glutamic acid and aspartic acid), polar amino acids (such as glutamine and asparagine), hydrophobic amino acids (such as leucine isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art as described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ele, Leu/Val, Ala/Glu, and Asp/Gly as well as these in reverse.

The polypeptides of the present invention have at least 20%, preferably at least 40%, more preferably at least 60%, even more preferably at least 80%, even more preferably at least 90%, and most preferably at least 100% of the glucanase activity of the polypeptide of SEQ ID NO:2, 4, 5 or 17.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted.

A polypeptide of the present invention may be a fungal polypeptide, for example, Aspergillus, Fusarium, Magnaporthe, or Phytophthora. In a preferred embodiment, the polypeptide is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* polypeptide.

In a more preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of Fusarium are defined by D. L. Hawksworth, P. M. Kirk, B. C. Sutton, and D. N. Pegler (editors), 1995, In Ainsworth & Bisby's *Dictionary of the Fungi*, Eighth Edition, CAB International, University Press, Cambridge, England, pp. 173–174.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g, Sambrook et al., 1989, supra).

As defined herein, an "isolated" polypeptide is a polypeptide which is essentially free of other non-glucanase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

B1. Nucleic Acid Molecules Which Encode Endochitinase Activity

Endochitinase refers to a polypeptide that degrades chitin by cleaving randomly between C1 and C4 linkages within the chitin polymer. In a first embodiment, the present invention is directed to isolated nucleic acid molecules which encode a polypeptide having endochitinase activity, selected from the group consisting of:

(a) a nucleic acid sequence having at least 75% nucleotide sequence identity with SEQ ID NO:10 from nucleotide 186 through nucleotide 1385 or SEQ ID NO:18 from nucleotide 18 to nucleotide 1217;

(b) a nucleic acid sequence encoding a polypeptide having endochitinase activity, said polypeptide having an amino acid sequence which has at least 85% identity with amino acids 1 to 399 of SEQ ID NO:11 or 19;

(c) a nucleic acid sequence which hybridizes under medium stringency or high stringency conditions with (i) SEQ ID NO:10 from nucleotide 186 through nucleotide 1385 or SEQ ID NO:18 from nucleotide 18 to nucleotide 1217; (ii) a subsequence of (i) of at least 100 contiguous nucleotides, or (iii) a complementary strand of (i) or (ii); and (d) a subsequence of (a), (b) or (c) wherein the subsequence encodes a polypeptide fragment which has endochitinase activity.

The fungal endochitinase nucleic acid molecules include genomic sequences which encode an endochitinase and which direct and regulate the transcriptional and translational expression of the endochitinase coding sequences, and cDNA sequences which encode an endochitinase.

Specific embodiments of nucleotide sequences which encode a polypeptide having endochitinase activity are given in SEQ ID NOS: 10 and 18. An exemplified endochitinase gene product has a predicted amino acid sequence as given in SEQ ID NOS:11 AND 19. A *F. venenatum* endochitinase full-length unmodified cDNA sequence is given in SEQ ID NO:10. The cDNA sequence is 1494 bp in length. The resulting open reading frame (coding portion), initiating at base 186 and terminating at base 1385 encodes a protein 399 amino acids in length (SEQ ID NO:11). A modified full length cDNA sequence which encodes a polypeptide having endochitinase activity is given in SEQ ID NO:18. This cDNA is 1227 bp in length. The open reading frame initiating at base 18 and terminating at base 1217 encodes a protein of 399 amino acids (SEQ ID NO:19). One modification made to the unmodified endochitinase sequence is the substitution of a CA-rich 5' leader sequence, GGATCCACCAACCAGCG, (SEQ ID NO:25)(bases #1–#17 of ENDO 5' primer, Table 2). The modified 5' leader sequence occurs immediately upstream of the ATG start codon of the endochitinase coding sequence. The modification renders the leader sequence rich in C and A nucleotides, and minimizes the number of T nucleotides. These characteristics are reported to enhance the translational efficiency of genes in plants. The DNA sequence containing the 5' portion of the endochitinase cDNA (FIG. 2), from which the remainder of the primer was designed, is presented in SEQ ID NO:6. The partial cDNA is 467 bp in length.

In another embodiment, the nucleic acid molecule is the sequence contained in plasmid Endo 167 (SEQ ID NO:18 which is a *F. venenatum* endochitinase modified full-length cDNA sequence) that is contained in *Escherichia coli* NRRL B-30202.

In another embodiment, the nucleic acid molecule is the sequence contained in plasmids FvEndoS or FvEndoAS that are contained in *Escherichia coli* NRRL B-30206 and NRRL B-30207, respectively.

The invention also encompasses nucleic acid sequences which have a degree of sequence identity to the coding region of SEQ ID NO:10 or 18 of at least 75%, preferably at least about 80%, more preferably at least about 85%, more preferably at least about 90%, and even more preferably about 95% and which encode a polypeptide having endochitinase activity, that is, the ability to degrade chitin by cleavage of internal glycosidic linkages. For purposes of the present invention, the degree of identity between two nucleic acid sequences is determined by the Clustal method (Thompson et al. 1994), using ClustalW 1.7 or 1.8 with the following pairwise alignment parameters: K-tuple=2; gap penalty=5; window size=4; diagonals—4. Multiple alignment parameters were: gap opening penalty=10; gap extension penalty=5.

Further, nucleic acid sequences which hybridize under medium stringency or high stringency conditions, as defined above, with the coding region of the DNA sequence of SEQ ID NO:10 or 18 and which encode a polypeptide having endochitinase activity are encompassed by this invention.

Also encompassed by the invention are subsequences of at least 100 contiguous nucleotides and preferably at least 200 contiguous nucleotides which hybridize under medium stringency or high stringency conditions, as defined above, with the coding region of the DNA sequence of SEQ ID NO:10 or 18.

The invention further encompasses a complementary strand of a nucleic acid sequence or subsequence of at least 100 contiguous nucleotides and preferably at least 200 contiguous nucleotides of a nucleic acid sequence which hybridizes under medium stringency or high stringency conditions, as defined above, with the coding region of the DNA sequence of SEQ ID NO:10 or 18.

The invention is further directed to a subsequence of the aforenamed nucleic acid sequences wherein the subsequence encodes a polypeptide fragment which has endochitinase activity.

B2. Polypeptides Having Endochitinase Activity

The present invention is also directed to isolated polypeptides having endochitinase activity which are encoded by the nucleic acid molecules described above. Isolated polypeptides having endochitinase activity comprise:

(a) a polypeptide having an amino acid sequence which has at least 85% identity with amino acids 1 to 399 of SEQ ID NO:11 or 19;

(b) a polypeptide encoded by a nucleic acid sequence which hybridizes under medium stringency or high stringency conditions with (i) SEQ ID NO:10 from nucleotide 186 through nucleotide 1385 or SEQ ID NO:18 from nucleotide 18 to nucleotide 1217; (ii) a subsequence of (i) of at least 100 contiguous nucleotides, or (iii) a complementary strand of (i) or (ii); and (c) a fragment of (a), or (b) that has endochitinase activity.

Isolated nucleic acid sequences encoding polypeptides comprising an amino acid sequence which has a degree of identity to the amino acid sequence of SEQ ID NO:11 or 19 of at least about 85%, preferably at least about 90%, more preferably at last about 95%, and most preferably at least about 97%, and which have endochitinase activity, (homologous polypeptides), are encompassed by the invention. For purposes of the present invention, the degree of identity between two amino acids is determined by the FASTA/FASTP method of Pearson (1990), using ALIGN (http://dot.imgen.bcm.tmc.edu:9331/seq-search/alignment.html), with the BLOSUM50 or PAM250 scoring matrix and the following pairwise alignment parameters: gap penalty=−12 for the first residue in the gap, and −2 for additional residues; K-tuple=2. Multiple alignments are carried out with the BLOSUM matrix, using the ClustalW 1.7 algorithm (Thompson et al. 1994). Multiple alignment parameters are: gap opening penalty=10, gap extension penalty=0.05; hydrophilic gap penalties on (hydrophilic residues GPSNDQERK); with residue-specific gap penalties.

Preferably, the polypeptides of the present invention comprise an amino acid sequence of SEQ ID NO:11 or 19 or a fragment thereof that has endochitinase activity. In another preferred embodiment, the polypeptide of the present invention comprises amino acids 1 to 399 of SEQ ID NO:11 or 19 or a fragment thereof that has endochitinase activity.

A fragment of SEQ ID NO:11 or 19 is a polypeptide having one or more amino acids deleted from the amino and/or carboxyl terminus of this amino acid sequence. Preferably, a fragment contains at least 339 amino acid residues, more preferably at least 359 amino acid residues, and most preferably at least 379 amino acid residues.

The present invention relates to isolated polypeptides having endochitinase activity which are encoded by nucleic acid sequences which hybridize under medium stringency conditions or high stringency conditions, as described in detail above, with (i) SEQ ID NO:10 from nucleotide 186 through nucleotide 1385 or SEQ ID NO:18 from nucleotide 18 to nucleotide 1217; (ii) a subsequence of (i) of at least 100 contiguous nucleotides, or (iii) a complementary strand of (i) or (ii).

The subsequence of SEQ ID NO:10 or 18 may be at least 100 contiguous nucleotides or preferably at least 200 contiguous nucleotides. Moreover, the subsequence may encode a polypeptide fragment which has endochitinase activity. Synonymous coding sequences and conservative amino acid substitutions, as described in detail, above, are incorporated herein by reference.

The polypeptides of the present invention have at least 20%, preferably at least 40%, more preferably at least 60%, even more preferably at least 80%, even more preferably at least 90%, and most preferably at least 100% of the endochitinase activity of the polypeptide of SEQ ID NO:11 or 19.

A polypeptide of the present invention may be obtained from microorganisms of any genus as described in detail above and which is incorporated herein by reference.

As defined herein, an "isolated" polypeptide is a polypeptide which is essentially free of other non-endochitinase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides as described in detail above and which is incorporated herein by reference.

C1. Nucleic Acid Molecules Which Encode Exochitinase Activity

Exochitinase refers to a polypeptide having the ability to degrade chitin by cleaving sequentially between each C1–C4 linkage initiating from the terminus of the chitin polymer. In a first embodiment, the present invention is directed to isolated nucleic acid molecules which encode a polypeptide having endochitinase activity, selected from the group consisting of:

(a) a nucleic acid sequence having at least 75% nucleotide sequence identity with SEQ ID NO:12 from nucleotide 108 to 1853 or SEQ ID NO:20 from nucleotide 18 to 1763;

(b) a nucleic acid sequence encoding a polypeptide having endochitinase activity, said polypeptide having an amino acid sequence which has at least 85% identity with amino acids 1 to 581 of SEQ ID NO:13 or 21;

(c) a nucleic acid sequence which hybridizes under medium stringency or high stringency conditions with (i) SEQ ID NO:12 from nucleotide 108 to 1853 or SEQ ID NO:20 from nucleotide 18 to 1763; (ii) a subsequence of (i) of at least 100 contiguous nucleotides, or (iii) a complementary strand of (i) or (ii); and (d) a subsequence of (a), (b) or (c) wherein the subsequence encodes a polypeptide fragment which has endochitinase activity.

The isolated nucleic acid molecules which encode a polypeptide having exochitinase activity include genomic sequences which encode an exochitinase and which direct and regulate the transcriptional and translational expression of the exochitinase coding sequences, and cDNA sequences which encode an exochitinase.

Specific embodiments of nucleotide sequences which encode exochitinase are given in SEQ ID NOS:8, 12 and 20. An exemplified exochitinase gene product has a predicted amino acid sequence as given in SEQ ID NOS:13 and 21. A Fusarium exochitinase full-length unmodified cDNA sequence is given in SEQ ID NO:12. The cDNA sequence is 1949 bp in length. The resulting open reading frame (coding portion), initiating at base 108 and terminating at base 1853 encodes a protein 581 amino acids in length. The encoded protein is described in SEQ ID NO:13. A *F. venenatum* modified full length cDNA sequence which encodes exochitinase is given in SEQ ID NO:20. This cDNA is 1781 bp in length. The open reading frame, initiating at base 18 and terminating at base 1763 encodes a protein of 581 amino acids (SEQ ID NO:21). One modification made to the unmodified exochitinase sequence is the substitution of a CA-rich 5' leader sequence, GGATCCACCAACCAGCG, (SEQ ID NO:25)(bases #1–#17 of EXO 5' primer, Table 2). The modified 5' leader sequence occurs immediately upstream of the ATG start codon of the exochitinase coding sequence. The modification renders the leader sequence rich in C and A nucleotides, and minimizes the number of T nucleotides. These characteristics are reported to enhance the translational efficiency of genes in plants.

The genomic DNA sequence containing a 5' portion of the exochitinase gene of *F. sporotrichioides* is presented in SEQ ID NO:8 (FIG. 3). The deduced polypeptide sequence is given in SEQ ID NO:9. The genomic DNA sequence is 995 bp in length, and nucleotide sequence analysis reveals 2 exons and 1 intron.

In another embodiment, the nucleic acid molecule is the sequence contained in plasmid Exo9 (SEQ ID NO:20 which is a *F. venenatum* exochitinase modified full-length cDNA sequence) that is contained in *Escherichia coli* NRRL B-30203.

In another embodiment, the nucleic acid molecule is the sequence contained in plasmids FvExoS or FvExoAS that are contained in *Escherichia coli* NRRL B-30208 and NRRL B-30209, respectively.

The invention also encompasses nucleic acid sequences which have a degree of sequence identity to the coding region of SEQ ID NO:12 or 20 of at least 75%, preferably at least about 80%, more preferably at least about 85%, more preferably about 90%, and even more preferably about 95% and which encode a polypeptide having exochitinase activity, that is, ability to degrade chitin by cleavage of terminal glycosidic linkages. For purposes of the present invention, the degree of identity between two nucleic acid sequences is determined by the Clustal method (Thompson et al. 1994), using ClustalW 1.7 or 1.8 with the following pairwise alignment parameters: K-tuple=2; gap penalty=5; window size 4; diagonals—4. Multiple alignment parameters were: gap opening penalty 10; gap extension penalty= 5.

Further, nucleic acid sequences which hybridize under medium stringency or high stringency conditions, as defined above, with the coding region of the DNA sequence of SEQ ID NO:12 or 20 and which encode a polypeptide having exochitinase activity are encompassed by this invention.

Also encompassed by the invention are subsequences of at least 100 contiguous nucleotides and preferably at least 200 contiguous nucleotides which hybridize under medium stringency or high stringency conditions, as defined above, with the coding region of the DNA sequence of SEQ ID NO:12 or 20.

The invention further encompasses a complementary strand of a nucleic acid sequence or subsequence of at least 100 contiguous nucleotides and preferably at least 200 contiguous nucleotides of a nucleic acid sequence which hybridizes under medium stringency or high stringency conditions, as defined above, with the coding region of the DNA sequence of SEQ ID NO:12 or 20.

The invention is further directed to a subsequence of the aforenamed nucleic acid sequences wherein the subsequence encodes a polypeptide fragment which has exochitinase activity.

C2. Polypeptides Having Exochitinase Activity

The present invention is also directed to isolated polypeptides having exochitinase activity which are encoded by the nucleic acid molecules described above. Isolated polypeptides having exochitinase activity comprise:

(a) a polypeptide having an amino acid sequence which has at least 85% identity with amino acids 1 to 581 of SEQ ID NO:13 or 21;

(b) a polypeptide encoded by a nucleic acid sequence which hybridizes under medium stringency or high stringency conditions with (i) SEQ ID NO:12 from nucleotide 108 to 1853 or SEQ ID NO:20 from nucleotide 18 to 1763; (ii) a subsequence of (i) of at least 100 contiguous nucleotides, or (iii) a complementary strand of (i) or (ii); and (c) a fragment of (a), or (b) that has exochitinase activity.

FIG. 4 shows the comparison of exochitinases encoded by *F. venenatum* cDNA (upper) and *F. sporotrichioides* genomic DNA (lower) (SEQ ID NOS: 14 and 15, respectively).

Isolated nucleic acid sequences encoding polypeptides comprising an amino acid sequence which has a degree of identity to the amino acid sequence of SEQ ID NO:13 or 21 of at least about 85%, preferably at least about 90%, more preferably at last about 95%, and most preferably at least about 97%, and which have exochitinase activity, (homologous polypeptides), are encompassed by the invention. For purposes of the present invention, the degree of identity between two amino acids is determined by the FASTA/FASTP method of Pearson (1990), using ALIGN (http://dot.imgen.bcm.tmc.edu:9331/seq-search/alignment.html), with the BLOSUM50 or PAM250 scoring matrix and the following pairwise alignment parameters: gap penalty=−12 for the first residue in the gap, and −2 for additional residues; K-tuple=2. Multiple alignments are carried out with the BLOSUM matrix, using the ClustalW 1.7 algorithm (Thompson et al. 1994). Multiple alignment parameters are: gap opening penalty=10, gap extension penalty=0.05; hydrophilic gap penalties on (hydrophilic residues GPSNDQERK); with residue-specific gap penalties.

Preferably, the polypeptides of the present invention comprise an amino acid sequence of SEQ ID NO:13 or 21 or a fragment thereof that has exochitinase activity. In another preferred embodiment, the polypeptide of the present invention comprises amino acids 1 to 581 of SEQ ID NO:13 or 21 or a fragment thereof that has exochitinase activity.

A fragment of SEQ ID NO:13 or 21 is a polypeptide having one or more amino acids deleted from the amino and/or carboxyl terminus of this amino acid sequence. Preferably, a fragment contains at least 494 amino acid residues, more preferably at least 523 amino acid residues, and most preferably at least 552 amino acid residues.

The present invention relates to isolated polypeptides having exochitinase activity which are encoded by nucleic acid sequences which hybridize under medium stringency conditions or high stringency conditions, as described in detail above, with (i) SEQ ID NO:12 from nucleotide 108 to 1853 or SEQ ID NO:20 from nucleotide 18 to 1763; (ii) a subsequence of (i) of at least 100 contiguous nucleotides, or (iii) a complementary strand of (i) or (ii).

The subsequence of SEQ ID NO:12 or 20 may be at least 100 contiguous nucleotides or preferably at least 200 contiguous nucleotides. Moreover, the subsequence may encode a polypeptide fragment which has exochitinase activity. Synonymous coding sequences and conservative amino acid substitutions, as described in detail, above, are incorporated herein by reference.

A polypeptide of the present invention may be obtained from microorganisms of any genus as described in detail above and which is incorporated herein by reference.

As defined herein, an "isolated" polypeptide is a polypeptide which is essentially free of other non-exochitinase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides as described in detail above and which is incorporated herein by reference.

D. Nucleic Acid Molecules Encoding Cell Wall-Degrading Enzymes

Any isolated cell wall-degrading nucleic acid molecule encoding a polypeptide having glucanase, endochitinase or exochitinase activity can be used in the present invention. The particular polynucleotide and amino acid sequences used are not critical features of the invention, so long as the desired cell wall-degrading function is achieved.

E. Comparison to Known Funzal Cell Wall Hydrolytic Enzymes

Computerized searches of the GenBank/EMBL sequence databases (Altschul et al. 1997) indicated that the *F. venenatum* full length cDNA sequences encoded polypeptides that had identity to known fungal cell wall hydrolytic enzymes. The *F. venenatum* glucanase shares 37% amino acid sequence identity with glucan 1,3-β-glucosidases from the yeast *Schizosaccharomyces pombe* (GenBank accession nos. Z99126 and AB000539), and 34% amino acid sequence identity with glucan 1,3-β-glucosidase precursors from the yeast *Saccharomyces cerevisiae* (SwissPro accession no. P15703; Klebl and Tanner 1989) and the yeast Candida albicans (SwissPro accession no. P43070). The *F. venenatum* endochitinase and exochitinase are similar to chitinases from other fungi. The endochitinase shares 56% amino acid sequence identity with an *Aspergillus nidulans* chitinase (GenBank accession no. D87063), 53% identity with chitinase antigens from *Coccidioides immitis* (Yang et al. 1996; Zimmerman et al. 1996), and 48% identity to a chitinase from *Aphanocladium album* (Blaiseau and Lafay 1992). The *F. venenatum* exochitinase had 66% and 58% amino acid sequence identity with two exochitinases from *Trichoderma harzianum* (Draborg et al. 1995), and 64% identity with a N-acetyl-β-D-glucosaminidase from *T. harzianum* (Peterbauer et al. 1996).

II. Using Probes to Identify and Isolate Homologs of the Sequences

The isolation of other Fusarium cell wall-degrading genes or homolog genes, including non-functional sequence homologs, may be accomplished by a number of techniques. For instance, nucleic acid probes based on the disclosed sequences can be used to isolate the desired gene from a cDNA or genomic DNA library, as described in detail, above. Nucleic acid probes can be either DNA or RNA. The desired gene can be isolated by hybridization of the probes to target sequences, including genomic library clones, cDNA library clones, or uncloned isolated DNA or cDNA fragments. Hybridization can be carried out under stringent, highly stringent, or low-stringency conditions either on membranes or in solution. Nucleic acid probes can be used as restriction fragment length polymorphic (RFLP) markers for the genetic mapping of loci, especially in fungi, or for the identification of homologous genes or loci in fungi.

III. Using Primers to Amplify Nucleotide Sequences

Primers based on the disclosed sequences can be used to isolate the desired genes from a cDNA or genomic library. The nucleic acids of interest can be amplified from nucleic acid samples using amplification techniques. For instance, polymerase chain reaction (PCR) technology can be used to amplify the sequences of the Fusarium cell wall-degrading enzymes and related genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired DNA or mRNA in samples, for nucleic acid sequencing, or for other purposes. For a general overview of PCR see, PCR PROTOCOLS: A GUIDE TO METHODS AND APPLICATIONS, Innis, et al. (eds.), Academic Press, San Diego (1990).

IV. Preparation of Recombinant Nucleic Acid Molecules (Constructs)

In one embodiment of this invention, recombinant nucleic acid molecules which contain isolated cell wall-degrading sequences and are suitable for transformation of host cells are prepared. A nucleic acid sequence coding for the desired polypeptide, for example, a cDNA or a genomic sequence encoding a full length protein or, a nucleic acid sequence encoding a homologous polypeptide is conveniently used to construct a recombinant expression cassette which can be introduced into the desired host cell. An expression cassette will typically comprise the Fusarium cell wall-degrading nucleic acid sequence operably linked to a one or more control sequences which direct the expression of the coding sequence in a suitable host cell under conditions compatible with the control sequences, and may include other transcriptional and translational initiation regulatory sequences which will direct the transcription of the sequence from the sense or antisense gene in the intended tissues of the transformed host cell. Expression will be understood to include any step involved in the production of the polypeptide including, but not limited to, transcription, post-transcriptional modification, translation, post-translational modification, and secretion.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequences include all components which are necessary or advantageous for the expression of a polypeptide of the present invention. Such control sequences include, but are not limited to, a leader, polyadenylation sequence, propeptide sequence, promoter, signal peptide sequence, and transcription terminator sequence, as described in detail above.

Promoter sequence as used herein, refers to a DNA sequence which when ligated to a nucleotide sequence of interest is capable of controlling the transcription of the nucleotide sequence of interest into mRNA. This is discussed in detail, above.

Promoters may be constitutive. The term "constitutive" when made in reference to a promoter means that the promoter is capable of directing transcription of an operably linked nucleic acid sequence under most environmental and developmental conditions in the absence of a stimulus (e.g., heat shock, chemicals, light, etc.), and/or in several or many tissues, cell types, or organs.

Promoters may be tissue specific or cell specific. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant.

For example, a constitutive plant promoter fragment may be employed which will direct expression of the Fusarium cell wall-degrading enzyme in some to many tissues of a plant. Such promoters are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Promoters for constitutive expression of anti-Fusarium genes in cereals and the tissues in which they have been shown to be active are the following: maize ubiquitin-1, young leaf, root, pollen, seed (cereals) (Christensen and Quail, 1996); maize Adh-1, embryo shoots, roots, anther, pollen, seed (rice) (Freeling and Bennett, 1985); rice ACT-1, shoot leaf, root, floral parts, including pollen (rice) (Zhang et al., 1991); CaMV 35S, leaf, root (rice) (Battraw et al.); ScBv, stem, palea, lemma, other floret organs, anther (oat) (Tzafrir et al.),1998.

Organ-specific promoters may be, for example, a promoter from storage sink tissues such as seeds, potato tubers, and fruits (Edwards & Coruzzi, 1990*, Ann. Rev. Genet.* 24:275–303), or from metabolic sink tissues such as meristems (Ito et al., 1994*, Plant Mol. Biol.* 24: 863–878), a seed specific promoter such as the glutelin, prolamin, globulin, or albumin promoter from rice (Wu et al., 1998*, Plant and Cell Physiology* 39:885–889), the storage protein napA promoter from *Brassica napus*, or any other seed specific promoter known in the art. Furthermore, the promoter may be a leaf specific promoter such as the rbcS promoter from rice or tomato (Kyozuka et al., 1993*, Plant Physiology* 102:991–1000, or the aldP gene promoter from rice (Kagaya et al., 1995*, Molecular and General Genetics* 248: 668–674), or a wound inducible promoter such as the potato pin2 promoter (Xu et al., 1993*, Plant Molecular Biology* 22:573–588).

Alternatively, the plant promoter may be under environmental or developmental control. Such promoters are referred to here as "inducible" promoters. Examples of environmental conditions that may effect transcription by inducible promoters include pathogen attack, anaerobic conditions, or the presence of light.

A promoter enhancer element may also be used to achieve higher expression of the gene in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin gene to enhance expression.

In a preferred embodiment, regulatory sequences or promoters that are particularly suitable for expression of genes in monocots are used. For example, as illustrated in the Examples, below, we selected the promoter of the maize Polyubiquitin-1 gene (Ubi-1, Christensen and Quail 1996) for regulating the expression of the glucanase and chitinase genes in wheat. The Ubi-1 promoter is active in a number of cereal species. It is termed a "constitutive" promoter because it functions in many different organs and tissues, including callus, young leaves, endosperm (A. Blechl, unpub.), mature pollen, and the floret organs of wheat (P. Okubara and A. Blechl, unpub.), in dividing embryogenic calli, leaves, roots and mature pollen of rice (Comejo et al. 1993), and plumules and radicals of maize seedlings (Liu et al. 1995). The use of the Ubi-1 promoter is envisioned to extend the application of the constructs to pathogens that attack other organs of wheat and to pathogens that attack other cereal crops, such as rice, maize, oat and barley.

The promoters can also be used to initiate transcription of MRNA molecules to inhibit expression of the gene. Means for inhibiting gene expression in host cells using recombinant DNA techniques are well known. For instance, antisense technology can be conveniently used. See, e.g., Sheehy et al., *Proc. Nat. Acad. Sci. USA*, 85:8805–8809 (1988), and Hiatt et al, U.S. Pat. No. 4,801,340. Introduction of nucleic acid configured in the sense orientation has also been shown to be an effective means by which to block the transcription of target genes. For an example of the use of sense suppression to modulate expression of endogenous genes see, Napoli et al., *The Plant Cell* 2:279–289 (1990), and U.S. Pat. Nos. 5,034,323, 5,231,020, and 5,283,184.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

The vector comprising the sequences from the cell wall-degrading genes may comprise a marker gene which confers a selectable phenotype on plant cells. Alternatively, and more typically for cereal transformation, a marker gene may be co-transformed on a separate vector molecule. For example, the marker may encode biocide resistance, particularly antibiotic resistance, such as resistance to kanamycin, carbenicillin, ampicillin or herbicide resistance, such as resistance to chlorosulfuron, or phosphinothricin (the active ingredient in bialaphos and Basta).

As described in the Examples below, for the expression the glucanase and chitinase genes, we constructed a vector derived from pAHC20 (Christensen and Quail 1996), in which the bar selectable marker gene is regulated by the maize Ubi-1 promoter (0.9 kb, including the first exon and first intron located in the 5' untranslated region) and NOS 3' terminator. The bar gene, conferring resistance to the herbicide bialaphos (de Block et al. 1987), is successfully and routinely used in our laboratory as a selectable marker for transgenic wheat plants. pUBK, engineered by Dr. Kent McCue (USDA-ARS, Albany, Calif.) to avoid the use of ampicillin resistance, was used. To construct pUBK, Dr. McCue replaced the origin of replication and gene for ampicillin resistance (bla) of pAHC20 (Christensen and Quail 1996) with the corresponding portion of pBGS9 (Spratt et al. 1986), which encodes kanamycin resistance (nptII). pUBK is publicly available from Dr. McCue.

Another factor in making recombinant constructs of transgenes is the efficiency of translation of the transgene mRNA. Computerized analyses of gene sequences and in vitro experiments indicate that the efficiency of translation initiation is mediated by three nucleotides (−3 to −1) immediately preceding the ATG start (initiation) codon. The −3 to—1 start codon context consensus for eukaryotic genes was reported to be ACC (Kozak 1987); a survey of plant genes yielded a consensus of ACA (Fuitterer and Hohn 1996); the start codon context for 85 maize genes was preferentially GGC or AAG (Luehrsen and Walbot 1994). To examine the hypothetical efficiency of translational initiation of leaf- or endosperm-specific mRNAs in pollen, we undertook a limited survey of start codon contexts for some monocot (*T. aestivum, H. vulgare, O. sativa, A. sativa, Z. mays*) genes from GenBank and EMBL databases. The consensus start codon context for wheat leaf mRNAs was GCC, and for monocot pollen mRNAs was G/A,A/C, not T.

Additionally, the 15–20 nucleotides upstream of ATG, including −3 to −1, are AC-rich in many monocot genes. Enhancements of translational efficiency of heterologous genes, e.g., fungal genes in monocots have been engineered.

V. Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g, a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vector may also contain sequences that stabilize the integration and expression of the nucleic acid construct in a host cell. These include DNA sequences carrying matrix attachment regions also known as scaffold attachment regions, for example, for yeast or plant, e.g., Arabidopsis or wheat, sources.

The vector may also contain one or more selectable markers which permit easy selection a transformed cells.

The vector may also contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination.

For autonomous replication, the vector may further comprise an origin of replication enabling the vector to replicate autonomously in the host cell in question.

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

VI. Preparation of Transgenic Host Cells and Production of Polypeptide

The present invention also relates to recombinant host cells, comprising a nucleic acid sequence of the invention, which are advantageously used in the recombinant production of the polypeptides. Preparation of transformed host cells and cloning methods are described by U.S. Pat. No. 5,374,540, which is incorporated herein by reference.

The host cell may be a unicellular microorganism, e.g., a prokaryote, or a non-unicellular microorganism, e.g., a eukaryote. Eukaryote cells can include any cell such as from an insect, fungus or plant. The term "plant" includes whole plants, plant parts or organs, plant tissue, as described in detail, above.

The present invention also relates to methods for producing a polypeptide comprising cultivating a host cell under conditions suitable for production of the polypeptide and recovering the polypeptide. The cells are cultivated in nutrient medium suitable for production of the polypeptide using methods know in the art. The polypeptides may be detected and recovered using methods known in the art.

The present invention also relates to methods for producing a polypeptide of the present invention comprising (a) cultivating a transgenic plant or a plant cell comprising a nucleic acid sequence encoding a polypeptide having enzyme activity of the present invention under conditions conducive for production of the polypeptide; and (b) recovering the polypeptide.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J. -C. Janson and Lars Ryden, editors, VCH Publishers, New York, 1989).

VIII. Preparation of Transgenic Plants

The transgenic plant or plant cell expressing an RNA transcript or polypeptide of the present invention may be constructed in accordance with methods known in the art. In brief, the plant or plant cell is constructed by incorporating one or more expression constructs encoding a polypeptide of the present invention into the plant host genome and propagating the resulting modified plant or plant cell into a transgenic plant or plant cell.

In a preferred embodiment of this invention, the transgenic plants of this invention are cereal crop plants, including but not limited to, wheat, rye, triticale, barley, maize, sorghum and rice. In a more preferred embodiment, the transgenic plants are wheat, maize, barley, oats, and rye. In an alternate preferred embodiment, the transgenic plants of this invention are dicotyledonous plants.

The DNA constructs described above may be introduced into the genome of the desired plant host by a variety of conventional techniques. Techniques for transforming a wide variety of higher plant species are well known and described in the technical and scientific literature. See, for example, Weising, et al., *Ann. Rev. Genet.* 22:421–477 (1988).

The DNA construct may be introduced directly into the genomic DNA of the plant cell using techniques such as biolistic methods, electroporation, PEG poration, and microinjection of plant cell protoplasts or embryogenic callus. Alternatively, the DNA constructs may be combined with suitable T-DNA flanking regions and introduced using an *Agrobacterium tumefaciens* or *A. rhizogenes* vector.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

Particle bombardment techniques are described in Klein, et al., *Nature* 327:70–73 (1987). A particularly preferred method of transforming wheat and other cereals is the bombardment of calli derived from immature embryos as described by Weeks, et al., *Plant Physiol.* 102:1077–1084 (1993).

Microinjection techniques are known in the art and well described in the scientific and patent literature. The introduction of DNA constructs using polyethylene glycol precipitation is described in Paszkowski, et al., *EMBO J.* 3:2717–2722 (1984). Electroporation techniques are described in Fronum, et al., *Proc. Nat'l Acad. Sci. USA* 82:5824 (1985).

*Agrobacterium tumefaciens*-meditated transformation techniques are also well described in the scientific literature. See, for example Horsch, et al., *Science* 233:496–498 (1984), and Fraley, et al. *Proc. Nat'l Acad. Sci. USA* 80:4803 (1983). Although Agrobacterium is useful primarily in dicots, certain monocots can be transformed by Agrobacterium. For instance, Agrobacterium transformation of rice is described by Hiei, et al, *Plant J.* 6:271–282 (1994); U.S. Pat. No. 5,187, 073; U.S. Pat. No. 5,591,616; Li, et al., *Science in China* 34:54 (1991); and Raineri, et al., *Bio/Technology* 8:33 (1990). Xu, et al., *Chinese J. Bot.* 2:81 (1990) transformed maize, barley, triticale and asparagus by Agrobacterium infection.

The present invention is particularly useful in wheat and other cereals. A number of methods of transforming cereals have been described in the literature. For instance, reliable methods for stable transformation of wheat, including the highly-regenerable cultivars such as the hard white spring wheat Bobwhite, are described (Vasil, et al., 1992, 1993; Weeks, et al., 1993; Becker et al., 1994; Nehra et al. 1994, Blechl and Anderson, 1996). U.S. Pat. Nos. 5,650,558 and 5,914,450 to Blechl et al. describe transformation of wheat and non-wheat cereal plants, which patents are incorporated herein by reference. Chen et al. (1998) introduced a rice chitinase gene under control of the 35S promoter into wheat. It was expressed in the first generation, but was subsequently silenced in progeny plants. Jensen et al. (1998) introduced a modified heat-stable 1,3–1,4-glucanase gene under control of its own promoter into barley and obtained plants that expressed the gene in germinating aleurone and scutellum. Bliffeld et al. (1998) introduced a barley seed class II chitinase gene under control of the maize Ubiquitin-1 promoter into wheat. Two lines of transgenic plants containing this construct showed increased resistance to infection by the powdery mildew-causing fungus *Erysiphe graminis*. Transgenic maize regenerants have been described by Fromm, et al., *Bio/Technology* 8:833–839 (1990) and Gordon-Kamm, et al., *Plant Cell* 2:603–618 (1990)). Similarly, oats (Sommers, et al., *Bio/Technology* 10:1589–1594 (1992)), sorghum (Casas, et al., *Proc. Nat'l Acad. Sci. USA* 90:11212–11216 (1993)), rice (Li, et al., *Plant Cell Rep.* 12:250–255 (1993)), barley (Yuechun & Lemaux, *Plant Physiol.* 104:37–48 (1994)), and rye (Castillo, et al., *Bio/Technology* 12:1366–1371 (1994)) have been transformed via bombardment. Transformation of rice is described by Toriyama, et al., *Bio/Technology*

6:1072–1074 (1988), Zhang, et al., Theor. Appl. Gen. 76:835–840 (1988), and Shimamoto, et al., *Nature* 338:274–276 (1989).

The present invention further relates to plants, seeds, plant tissues, plant organs, and plant cells transiently expressing the claimed sequences. Transient expression refers to the generation of mRNA and/or protein from the claimed DNA sequences in plants without stable integration of the plasmid into host genomes. Such expression might be observed after 1 to 14 days following introduction of DNA by particle gun bombardment, Agrobacterium, and other means used for plant transformation.

Transformed plant cells that are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the cell wall-degrading polynucleotide sequences. Plant regeneration from cultured protoplasts is described in Evans, et al., PROTOPLASTS ISOLATION AND CULTURE, HANDBOOK OF PLANT CELL CULTURE, Macmillian Publishing Company, New York, pp. 124–176 1983; and Binding, REGENERATION OF PLANTS, PLANT PROTOPLASTS, CRC Press, Boca Raton, pp. 21–73 1985. Regeneration can also be obtained from plant callus, explants, organs, or parts thereof. Such regeneration techniques are described generally in Klee, et al. *Ann. Rev. of Plant Phys.* 38:467–486 (1987).

Transformed plants are evaluated for the presence of the desired properties and/or the extent to which the desired properties are expressed. A first evaluation may include the level of expression of the newly introduced genes, the level of fungal resistance of the transformed plants, and stable heritability of the desired properties.

One of skill will recognize that after the expression cassette is stably incorporated in transgenic plants and confirmed to be operable, it can be introduced into other plants by sexual crossing. A technique used to transfer a desired phenotype to a breeding population of plants is through backcrossing. However, any of a number of standard breeding techniques can be used, depending upon the species to be crossed.

Any plant species or variety that is subject to fungal attack may be transformed with one or more genetic constructs according to the invention in order to improve resistance to Fusarium or other pathogens, for example, to improve resistance to Fusarium head blight and other fungal diseases, including by (a) generation of cell wall-degrading enzymes, including proteins having the capability of degrading the glucan and chitin cell wall components of *F. venenatum* and other Fusarium species, including *F. graminearum* and *F. culmorum*, the principle causal agents of head blight (scab) in the U.S., (b) expression of the cell wall-degrading enzymes in transgenic monocots, including wheat, barley or oats, to confer partial or complete resistance to Fusarium species and to other fungal pathogens of wheat and other cereal crops, (c) limiting the spread of the pathogenic fungus Fusarium and curtailing the accumulation of DON in infected heads, and (d) expression of the cell wall-degrading enzymes in dicots to confer resistance to plant pathogens.

The following, non-limitative, list is illustrative of fungal diseases: Fusarium head blight, Fusarium wilt caused by *Fusarium oxysporum* or *Fusarium solani*, stock rot caused by *Fusarium moniliforme*, fungal diseases caused by Phytophthora.

As a matter of illustration the species of the following, non-limitative, list are moncots of particular interest: wheat, rice, barley, maize, rye, oat, sorghum, triticale.

Analysis of transgenic lines may be done by northern blots, in situ hybridization, RT-PCR, S1 nuclease protection assays, RNase protection assays, Western blots, enzyme assays or other methods for detection of expressed mRNA or protein.

IX. USES

As discussed above, a particular use of the invention is the provision of plants or plant cells transformed with a DNA sequence encoding a glucanase, endochitinase or exochitinase coding sequence to provide plants having resistance to plant pathogens, particularly, Fusarium species.

Also, another use of the invention is as probes and primers capable of detecting a glucanase, endochitinase or exochitinase gene or functional equivalents thereof in fungi of the genus Fusarium and the use of the probes to isolate DNA sequences encoding a glucanase, endochitinase or exochitinase gene or functional equivalent thereof.

Using the nucleic acid sequences of the invention facilitates the isolation of homologous genes from hosts to obtain genes which protect host cells, including fungi and plants against related fungal pathogens.

Another use of the sequences is in the antisense orientation as a gene knock-out.

Another use is to generate Fusarium cell wall-degrading proteins for research purposes.

Another use is to generate cell-wall degrading chitinases and glucanases for use in degrading seafood waste, such as shells that contain chitin, or for use for chemical modification of chitin or glucan.

Overview: In our examples, below, we describe in detail work to combat Fusarium head blight (scab) and other Fusarium-mediated diseases of wheat and other crops. We isolated cDNAs and genes encoding enzymes that digest the glucan and chitin components of fungal cell walls, and identified three distinct cDNA clones (encoding a glucanase, an endochitinase, and an exochitinase) from *Fusarium venenatum*, and gene homologs for the endochitinase and exochitinase from *F. sporotrichioides*. *F. venenatum* is a close relative of the causal agent of head blight, *F. graminearum*. Both *F. venenatum* and *F. sporotrichioides* produce mycotoxins similar to that made by the head blight pathogen. Cell-wall degrading enzymes from a Fusarium species are required by the fungus for normal growth and development.

The nucleotide sequences of two glucanase cDNA clones, an endochitinase cDNA clone, and 3 exochitinase cDNA clones from a collection of *F. venenatum* ESTs were examined. Both glucanase cDNA clones were determined to be full-length, whereas all the chitinase clones were partial cDNA clones that were missing the 5' ends, including the ATG translational start codons. To restore the missing sequences, we performed a polymerase chain reaction (PCR) method known as 5' anchored PCR on a genomic library of *F. sporotrichioides*. The resulting 5' genomic fragments for both the endo- and exochitinase could not be added directly to the partial cDNA clones because each fragment carried an intron. However, the nucleotide sequences of these 5' fragments provided the necessary data for the design of oligonucleotide PCR primers with which full length clones were eventually obtained.

To obtain full-length cDNA clones of the endo- and exochitinases, we performed a second polymerase chain reaction procedure using a cDNA library of *F. venenatum*. The primers used to amplify the cDNAs eliminated most of the untranslated sequences flanking the coding region. The PCR primers specific to the 5' ends of the genes included additional nucleotides that replaced the 15–16 bases immediately upstream of the ATG start codon with A or C nucleotides. The AC-rich start codon context (and 5' flanking nucleotides) was expected to render the translation of the gene transcripts more facile in a variety of wheat and other monocot organs. The PCR primers added a 5' BamHI restriction site and a 3' BglII restriction site to the termini of the amplified portions of the cDNAs. These sites were useful for cloning the cDNAs into our monocot expression vector.

The endo- and exochitinase PCR products, and the glucanase cDNA, were first cloned in bacterial vectors, either pCR2.1 or pBKS+. Production of appropriate amounts of the cDNA plasmids for subsequent cloning were readily obtained in the bacterial host. Also, nucleotide sequences were verified for all three cDNAs after cloning in bacterial vectors, to check that PCR amplification introduced modifications to the 5' region and eliminated unwanted flanking sequences without altering the coding regions. The cDNAs were then introduced into the vector, pUBKBg1II-, for expression in monocotyledonous plants. The monocot expression vector carried a promoter from the maize Polyubiquitin-1 (Ubi-1) gene, the bar gene for resistance to the herbicide bialaphos, a 3' terminator segment from the nopaline synthase (nos) gene of *Agrobacterium tumefaciens*, and the nptII marker gene for resistance to the antibiotic kanamycin. A BglII restriction enzyme site located in the Ubi-1 promoter was destroyed by site-directed mutagenesis. This allowed the removal of the bar gene from pUBKBglII- with restriction enzymes BglII and BamHi, and substitution of the *F. venenatum* cDNAs. Both sense and antisense orientations of the three cDNAs (6 total) were obtained, as determined from nucleotide sequences of the promoter-transgene and transgene-terminator junctions.

Embryos of *Triticum aestivum* cultivar Bobwhite were bombarded simultaneously with plasmids carrying the sense orientations of the cDNAs plus a selector marker plasmid carrying the bar gene. Calli and regenerated plants were cultured using methods developed in the laboratory. Candidate transgenic plants were selected on the basis of growth in the presence of the herbicide bialaphos (conferred by the bar gene). DNA from leaf sections of candidate tranformants were further analyzed by PCR with a primer designed from the maize Ubi-1 promoter sequence and a second primer specific for each of the transgene (glucanase, endochitinase, and exochitinase) sequences. Those plants carrying transgene DNA are being propagated for production of seed that are homozygous for the transgenes. Homozygous lines are tested for expression of the transgenes and tested for resistance to *F. graminearum* and other fungal pathogens.

EXAMPLES

The following examples are intended only to further illustrate the invention and are not intended to limit the scope of the invention which is defined by the claims. The examples use many techniques well known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art. Reagents, buffers and culture conditions are also known to the art. References providing standard molecular biological procedures include Sambrook et al. (1989) *Molecular Cloning*, second edition, Cold Spring Harbor Laboratory, Plainview, N.Y.; R. Wu (ed.) (1993) *Methods in Enzymology* 218; Wu et al. (eds.) *Methods in Enzymology* 100, 101; Glover (ed.) (1985); *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include Kung and Arntzen (eds.) (1989) *Plant Biotechnology*, Butterworths, Stoneham, Mass.; R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) Academic Press, San Diego, Calif.; I. Potrykus (1991) *Ann. Rev. Plant Physiol. Plant Mol. Biol.* 42:205; Weising et al. (1988) *Annu. Rev. Genet.* 22:421; van Wordragen et al. (1992) *Plant Mol. Biol. Rep.* 19:12; Davey et al. (1 989) *Plant Mol. Biol.* 13:273; Walden and Schell (1990) *Eur. J Biochem.* 192:563; Joersbo and Brunstedt (1991) *Physiol. Plant.* 81:256 and references cited in those references. Abbreviations and nomenclature, where employed, are deemed standard in the field and are commonly used in professional journal such as those cited herein. All references cited in the present application are expressly incorporated by reference herein.

Example 1

Isolation of *Fusarium venenatum* Mycelia

*Fusarium venenatum* CC 1–3, a morphological mutant of Fusarium strain ATCC 20334 (Wiebe et al., 1991*, Mycol. Research* 95: 1284–1288), was grown in a two-liter lab-scale fermentor using a fed-batch fermentation scheme with NUTRIOSE™ (Roquette Freres, S. A., Beinheim, France) as the carbon source and yeast extract. Ammonium phosphate was provided in the feed. The pH was maintained at 6 to 6.5, and the temperature was kept at 30° C. with positive dissolved oxygen.

Mycelial samples were harvested at 2, 4, 6, and 8 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981*, Cell* 26: 29–37), and the RNA samples were analyzed by Northern hybridization after blotting from 1% formaldehyde-agarose gels (Davis et al., 1986*, Basic Methods in Molecular Biology*, Elsevier Science Publishing Co., Inc., New York). Polyadenylated MRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 $\mu$g of poly(A)+mRNA according to the method of Gubler and Hoffman (1983*, Gene* 25: 263–269) except a NotI-(dT) 18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen Corporation, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent *E. coli* TOP10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) which contained kanamycin at a final concentration of 50 µg/ml.

Two independent directional cDNA libraries were constructed using the plasmid cloning vector pZErO-2. 1. Library A was made using MRNA from mycelia harvested at four days, and Library B was constructed with mRNA from the six day time point. Neither cDNA library was amplified in order to examine a representative "snapshot" of the gene expression profile in the cells. Instead the libraries were plated, titered, and independent clones from each were analyzed by DNA sequencing.

Library A (4 day cells) consisted about $7.5 \times 10^4$ independent clones and Library B (6 day cells) consisted of roughly $1.2 \times 10^5$ clones. Miniprep DNA was isolated from forty colonies in each library and checked for the presence and size of cDNA inserts. In this analysis 39 of 40 colonies (97.5%) from Library A contained inserts with sizes ranging from 600 bp to 2200 bp (avg.=1050 bp). Similarly, 39 of 40 colonies (97.5%) picked from Library B had inserts with sizes ranging from 800 bp to 3600 bp (avg.=1380 bp).

Example 3

Template Preparation and Nucleotide Sequencing

From each cDNA library described in Example 2, 1192 transformant colonies were picked directly from the transformation plates into 96-well microtiter dishes which contained 200 µl of 2YT broth (Miller, 1992, supra) with 50 µg/ml kanamycin. The plates were incubated overnight at 37° C. without shaking. After incubation 100 µl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing was done with a Perkin-Elmer Applied Biosystems Model 377 Sequencer XL (Perkin-Elmer Applied Biosystems, Inc., Foster City, Calif.) using dye-terminator chemistry (Giesecke et al., 1992, *Journal of Virology Methods* 38: 47–60) and the reverse lac sequencing primer (New England Biolabs, Inc., Beverly, Md.).

Example 4

Analysis of DNA Sequence Data

Nucleotide sequence data were scrutinized for quality, and samples giving improper spacing or ambiguity levels exceeding 2% were discarded or re-run. Vector sequences were removed with assistance of FACTURA™ software (Perkin-Elmer Applied Biosystems, Inc., Foster City, Calif.). In addition, sequences were truncated at the end of each sample when the number of ambiguous base calls increased. All sequences were compared to each other to determine multiplicity using AutoAssembler™ software (Perkin-Elmer Applied Biosystems, Inc., Foster City, Calif.). Lastly, all sequences were translated in three frames and searched against a non-redundant data base (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5

Identification of ESTs Encoding Putative Chitinolytic Enzymes

EST clones encoding putative chitinolytic enzymes were identified by partial sequencing of random cDNA clones using an Applied Biosystems Model 377 XL Automated DNA Sequencer according to the manufacturer's instructions and comparison of the deduced amino acid sequence of each EST to the amino acid sequences in a NRDS made from publicly available protein and nucleic acid databases (e.g., GENBANK, EMBL, TREMBL, GENPEPT, SWISSPROT, PIR). EST translations showing deduced amino acid sequence identities to *Trichoderma harzianum* exochitinase (TREMBL P78739), the endochitinase 1 precursor of *Coccidioides immitis* (SWISSPROT P54196), *Coccidioides immitis* chitinase (PIR JC4565), exo-beta-1,3-glucanase from *Saccharomyces cerevisiae* (SWISSPROT P15703), poly-beta-glucosaminidase from *Clostridium thermocellum* (TREMBL Q59326), *Emericella nidulans* chitinase (GENPEPT D87063), and the chitooligosaccharidolytic beta-N-acetylglucosaminidase from *Bombyx mori* (SWISSPROT P49010) were identified as described in Example 4.

Example 6

Transformation of *E. coli* with Plasmid DNA Carrying the Glucanase Full-Length cDNA, and the Endochitinase and Exochitinase Partial cDNAs Two *F. venenatum* glucanase cDNA clones, an endochitinase cDNA clone, and 3 exochitinase cDNA clones, all in the vector pZErO-2 (Invitrogen, Carlsbad, Calif.), were selected from Example 5. These clones were assigned identities based on matches to known chitinases and glucanases in the GenBank database as described in Example 5. From preliminary nucleotide sequences (ESTs) of the 5' ends of the cDNAs, one full-length glucanase clone, one partial endochitinase cDNA clone, and the longest of the 3 exochitinase partial clones were selected for all further work.

Approximately 5 to 10 ng of plasmid DNAs carrying the above three cDNAs were introduced separately into *E. coli* host strain NM522 by electroporation. Electroporation was performed on 50 µL aliquots of cells ($3.5 \times 10^7$/µg) using the Bio-Rad Gene Pulser (Bio-Rad, Hercules, Calif.), in 0.2 cm gap cuvettes at 2500 Volts. Following electroporation, the cells were suspended in 1 mL 2% (w:v) Bacto tryptone, 0.5% (w:v) yeast extract, 0.05% (w:v) sodium chloride, 20 mM glucose, 10 mM magnesium chloride, and 2.5 mM potassium chloride. The cells were maintained at 37° C. for 60 minutes with agitation at 200–300 rpm. Aliquots of 50 to 200 μL of cells were spread onto agar plates of Luria broth (LB) containing 50 μg/mL kanamycin sulfate. After culture at 37° C. for 16–20 hr, bacterial colonies showing good growth were transferred to a fresh LB-kanamycin plate. From this stock plate, additional cultures of individual colonies were grown for plasmid DNA isolation.

Example 7

Plasmid DNA Isolation

For plasmid DNA isolation, 30 mL cultures of *E. coli* containing the above cDNA clones were incubated at 37° C., 16–18 hr, with agitation. Culture medium was a modified LB containing 1.5% (w:v) Bacto tryptone, 0.75% (w:v) yeast extract, 0.75% (w:v) sodium chloride, 15 mM TRIS-Cl buffer, pH 7.0, 1.5 mM magnesium chloride, and 50 μg/mL kanamycin sulfate. Cells were collected by centrifugation at 8000×g for 10 minutes at 4° C. Plasmid DNA was isolated according to the protocol described in the Qiagen Plasmid Midi Kit (Qiagen, Inc., Valencia, Calif.). Plasmid DNA was isolated from 1.5 mL cultures using the QIAprep 8 kit and QIAvac Manifold-6S (Qiagen, Inc., Valencia, Calif.).

Example 8

Authentication of the cDNA Clones by Restriction Enzyme Treatment

Preliminary nucleotide sequence (EST) data were analyzed for the presence of restriction enzyme recognition sites using the Lasergene software programs EditSeq and Map-Draw (DNASTAR, Inc, Madison, Wis.). Restriction enzymes that cleaved in one or more of the cDNA coding sequences or in the polylinker region of pZErO-2 were used. Plasmid DNAs (~0.5–1 μg), prepared as described in Example 7, were incubated with ApaI, BamHI, EcoRI or KpnI in a total volume of 15 μL as prescribed by the enzyme manufacturers. The cleavage products were partitioned on 1% agarose in 40 mM TRIS acetate, pH 8.2, 1 mM EDTA, stained with an ethidium bromide solution (~1 μg/mL), and visualized by irradiation with an ultraviolet light source (UVT 400-M transilluminator, IBI Kodak, Rochester, N.Y.). The results are shown in the Table 1, below.

TABLE 1

| Plasmid/cDNA | Restriction Enzyme | Fragments Obtained (kb) | Theoretical Fragments (kb) |
|---|---|---|---|
| Glucanase | Apa I | 3.7, 0.6 | 3.6, 0.7 |
| | BamHI | 4.4 | ~4.3 |
| | EcoRI | 4.4 | ~4.3 |
| | Kpn I | no digestion | no digestion |
| Endochitinase | Apa I | 3.7, 0.9 | 3.7, 1.0 |
| | BamHI | 4.6 | 4.5–4.7 |
| | EcoRI | 4.5 | 4.5–4.7 |
| | Kpn I | 4.5, 0.3 | 4.4, 0.2 |
| Exochitinase | Apa I | 4.7 | 4.5–4.7 |
| | BamHI | 4.7 | 4.5–4.7 |
| | EcoRI | 4.7 | 4.5–4.7 |
| | Kpn I | 3.8, 0.9 | 3.3, 1.4 |

Example 9

Nucleotide Sequence Determination and Sequence Analysis of the Glucanase Full-Length cDNA Clone, and the Endochitinase and Exochitinase Partial cDNA Clones One glucanase cDNA clone, the endochitinase cDNA clone, and the longest exochitinase cDNA clone were selected for more rigorous, double strand nucleotide sequence determinations. Each cDNA was sequenced by a modified method of Sanger et al. (1977), using 250–500 ng of plasmid DNA in 2 μL, 8 μL of BigDye Terminator Mix and 1 μL of primer (4 uM) in a total volume of 20 μL, according to the ABI Prism BigDye™ Terminator Cycle Sequencing Ready Reaction Kit (Perkin Elmer Applied Biosystems, Foster City, Calif.). The PCR protocol (25 cycles of 96° C., 30 sec, 50° C. for 15 sec, 60° C. for 4 min) was performed in a PTC-100 Programmable Thermal Controller (MJ Research, Watertown, Mass.). Fluorescently-labeled PCR products were enriched from unincorporated fluorescent dideoxynucleotides by passage through a column containing 50 mg (dry weight) of Sephadex G-50 Fine, DNA grade, (Amersham Pharmacia, Biotech AB, Uppsala, Sweden) imbibed in water. Sequence data of these clones and all other DNA templates were obtained with the ABI Prism 310 Genetic Analyzer. Best results were obtained with an injection time of 45 seconds at 3 kV injection voltage, and a run time of 90–120 minutes at 15 kV and 42° C., using the Seq POP6 (1 mL) E module. Sequence data was assembled and proofread using the ABI Prism 310 Genetic Analyzer Data Collection software, version 1.0.2 (Perkin Elmer Applied Biosystems, Foster City, Calif.).

Nucleotide sequences of the 5' and 3' ends of the cDNA inserts in pZErO-2 were obtained with primers M13F (5' GTAAAACGACGGCCAG)(SEQ ID NO:26) and Ml3R (5' AGCGAATAACAATTTCACACAGGA)(SEQ ID NO:27). Additional sequences were obtained by primer walking. Primers synthesized for this purpose, shown in Table 2, were 902A and 902B for the glucanase cDNA; 958A–D for the endochitinase clone; and 1082 A–D for the exochitinase clone. The glucanase cDNA was 1023 bp. The full length unmodified glucanase cDNA is shown in SEQ ID NO:1. Using agarose gel electrophoresis, the unmodified partial cDNA endochitinase was 1290 bp, and the unmodified partial exochitinase cDNA was 1390 bp.

Sequences were compared to entries in the GenBank database using BLASTN and BLASTX algorithms (Altschul et al., 1997). Portions of the *F. venenatum* glucanase cDNA showed 60–70% amino acid sequence identity to a 1,3-beta-glucosidase gene from *Schizosaccharomyces pombe* (Accession Number Z99126). The glucanase cDNA was full-length, having an ATG start codon at approximately the same position as that observed in the *S. pombe* gene. Segments of the *F. venenatum* endochitinase partial cDNA had 70–80% amino acid sequence identity to a chitinase antigen from *Coccidioides immitis* [Accession Number U33265, Yang et al., *Infect. Immun.*, 64:1992–1997 (1996)]. Segments of the exochitinase partial cDNA sequence shared about 80% amino acid sequence identity with an exochitinase gene from *Trichoderma harzianum* [Accession Number S80069, Draborg et al., *Biochem. Mol. Biol. Int*. 36:781–791 (1995)]. Both the endo- and exochitinase cDNAs appeared to be partial clones based on the absence of candidate 5' ATG start codons and on comparisons with the sequences identified in the database searches.

TABLE 2

Primers Used for Polymerase Chain Reaction Experiments

| Name | Purpose | Target DNA | Sequence (5' to 3') | SEQ ID NO: |
|---|---|---|---|---|
| 128 | Sequencing of 5' exo-chitinase PCR product | λgt11 cloning vector | TCCTGGAGCCCGTCAGTATCGG | 28 |
| 129 | PCR amplification of 5' portion of exochitinase, | λgt11 cloning vector | TGGCTGAATATCCACGGTTTCC | 29 |
| 410 | Sequencing of 5' endo-chitinase PCR product | pZERO-2 cloning vector | ATTTAGGTGACACTATAG | 30 |
| 720 | PCR amplification of 5' portion of endochitinase, | pZERO-2 cloning vector | CAGGACAGGAAACAGCTATGACC | 31 |
| 902 A | Sequencing of glucanase cDNA, forward | Glucanase cds | CFATCAAGCAGCACGG | 32 |
| 902 B | Sequencing of glucanase cDNA, reverse | Glucanase cds | CTGGAAGGTCTTGAGGC | 33 |
| 958 A | Sequencing of chitinase cDNA, forward | Endochitinase cds | GATATCGATTGGGAGTACC | 34 |
| 958 B | Sequencing of chitinase cDNA, reverse | Endochitinase cds | CATGGTACGTGACTGAGG | 35 |
| 958 C | Sequencing of chitinase cDNA, forward | Endochitinase cds | CAACCCTCAGTCACGTAC | 36 |
| 958 D | Sequencing of chitinase cDNA, reverse | Endochitinase cds | CCTCGTTGGCATCCTG | 37 |
| 1003 | PCR amplification of 5' portion of exochitinase | Exochitinase cds | AGATCCTTATAGGCAAGCTCAAC GACACCG | 38 |
| 1009 | Sequencing of 5' exo-chitinase PCR product | 5' portion of exo-chitinase gene | CATAAATACCGGCAAGATCC | 39 |
| 1010 | PCR amplification of 5' pottion of endochitinase | Endochitinase cds | ATCGATATCTATACCGTCAAAACCG | 40 |
| 1011 | Sequencing of 5' endo-chitinase PCR product | 5' porfion ofendo-chitinase cDNA | ATCGATATCTATACCGTCAAAACCG | 41 |
| 1014 | Sequencing of glucanase genomic fragment | pFSC22-2 | ATCTGCTGGGCGAGCTTC | 42 |
| 1015 | Sequencing of glucanase genomic fragment | pFSC22-2 | CAGAAACCACTGGCATCC | 43 |
| 1016 | Sequencing of glucanase genomic fragment | pFSC22-2 | AAGTTCGGCCTTACTTGC | 44 |
| 1017 | Sequencing of glucanase genomic fragment | pFSC22-2 | CTTTGGGCTCGTATTCAC | 45 |
| 1018 | Sequencing of glucanase genomic fragment | pFSC22-2 | CTTCAGCACTCTCAGCAC | 46 |
| 1021 | Sequencing of glucanase genomic fragment | pFSC22-2 | GGACTGAGGGAGTCTTCGTTC | 47 |
| 1023 | Sequencing of glucanase genomic fragment | pFSC22-2 | TCTACCCTACAACACTCATC | 48 |
| 1038 | Sequencing of glucanase genomic fragment | pFSC22-2 | GTCGATCATGGTGGAAAG | 49 |
| 1040 | Sequencing of glucanase genomic fragment | pFSC22-2 | TGTCCCTGTTACTAACGG | 50 |
| 1042 | Sequencing of glucanase genomic fragment | pFSC22-2 | TAGTCGCCTTTCTAAGCC | 51 |
| 1047 | Sequencing of 5' exo-chitinase PCR product | 5' portion of exo-chitinase gene | AAGAA GCCTCGATGAGGGTACTCG | 52 |
| 1048 | Sequencing 5' exo-chitinase PCR product | 5' portion of exo-chitinase gene | ATCTCACTCACCTCACCTC | 53 |
| 1082 A | Sequencing of chitinase cDNA, forward | Exochitinase cds | CCGGTATTTATGAGTATGG | 54 |
| 1082 B | Sequencing of chitinase cDNA, reverse | Exochitinase cds | GATAGTCTCAGTCCATACGG | 55 |
| 1082 C | Sequencing of chitinase cDNA, forward | Exochitinase cds | GTACCTTGACTGTGGGC | 56 |
| 1082 D | Sequeucing of chitinase cDNA, reverse | Exochitinase cds | GGAAATGCGAGGGAAG | 57 |
| ENDO 3' | Start codon context modification | Endochitinase gene | AGATCTCGCCTCAATTGTCCGGAACC | 58 |
| ENDO 5' | Start Codon context modification | Endochitinase gene | GGATCCAACACCACGCGATGGGTGG TGGACCCGAAGG | 59 |
| EXO 3' | Start codon context | Exochitinase gene | AGATCTGCGTCAAATTTATCATCCCTCG | 60 |
| EXO 5' | Stact codon context modification | Exochitinase gene | GGATCCACCAACCAGCGATGTCG TCCAAGGCTCTTCTGGCCGTTG | 61 |
| FVEN B1 | PCR amplification of Ubiquitin-endochitinase gene fusion | Endochitinase cds | GCTTCATGCAACCGTACAAGTTGG | 62 |
| FVEX B1 | PCR amplification of Ubiquitin -exochitinase gene fusion | Exochitinase cds | CGACTTCACCCACTGCTTCTTTTGC | 63 |

TABLE 2-continued

Primers Used for Polymerase Chain Reaction Experiments

| Name | Purpose | Target DNA | Sequence (5' to 3') | SEQ ID NO: |
|------|---------|------------|---------------------|------------|
| FVGLU B1 | PCR amplification of Ubiquitin-glucanase gene fusion | Glucanase cds | CCCAGACGCCAACAAGGATCTTC | 64 |
| GLUC 3' | Start codon context modification | Glucanase gene | AGATCTGGCTTAGCAAGTAAGG CTGAAC | 65 |
| GLUC 5' | Start codon context modificaiicn | Glucanase gene | GGATCCACCAACCAGCGATGAAGTT CTTCAGCACTCTTAGC | 66 |
| Glucgene-1 | Sequencing of glucanase genomic fragment | pFSC22-2 | GTACTGGGTTGGTGAGAC | 67 |
| Glucgene-2 | Sequencing of glucanase genomic fragment | pFSC22-2 | CCATTCCAAGACCAGGC | 68 |
| NOS A | Sequcncing across the Transgene-NOS fusion border | NOS 3' UT | CCCATCTCATAAATAACGTC | 69 |
| UBI1A | Sequencing across the Ubiquitin-transgene fusion border | Ubiquitin promoter | CCTCCCTTCATACGCTAT | 70 |
| UBI A2 | PCR amplification of Ubiquitin-transgene fusion | Ubiquitin promoter | CCTCCCTTCATACGCTATTTATTTGC | 71 |
| UBI 1B | Sequencing mutated BglII site in promoter | Ubiquitin promoter | GACACCAACCACCGAACCA | 72 |
| UBI 1E | Removal of Bgl II site from promoter by site-directcd mutagenesis | Ubiquitin promoter | CACACACAACCAGATTTCCCCC AAATCCACC | 73 |
| UBI 1F | Removal of Bgl II site from promoter by site-directcd mutagenesis | Ubiquitin promoter | GGTGGATTTGGGGGAAATCTG GTTGTGTGTG | 74 |

Example 10

Isolation and Sequencing of *F. sporotrichioides* Genomic DNA Fragments encoding a Glucanase and the 5' Ends of the Endochitinase and Exochitinase Genes Glucanase. The nucleotide sequence of a *F. sporotrichioides* genomic fragment encoding a glucanase was obtained as described in Example 9 from plasmid clone pFSC22-2. Primers used for sequencing were: 1014, 1015, 1016, 1017, 1018, 1021, 1023, 1038, 1040, 1042, Glucgene-1 and Glucgene-2 (Table 2). The nucleotide sequence was proofread and assembled as in Example 9.

Endochitinase. The 5' end of the endochitinase cDNA (FIG. 2) was obtained by PCR amplification of 0.5 μg of the *F. venenatum* cDNA library using primers 1010 (from the endochitinase EST) and 720 (from the pZERO-2 sequence for M13 reverse primer). PCR conditions for the 1010/720 reaction were 94° C., 30 sec (1 min. first cycle); 52° C., 25 sec; 72° C., 60 sec, for 25 cycles. The PCR product was purified after partitioning on an agarose gel. Nucleotide sequence data of the endochitinase PCR product (5' end) was obtained using primers 410, corresponding to the SP6 promoter of the cloning vector pZERO-2 (Invitrogen), and 1011, corresponding to the endochitinase cDNA. PCR conditions for the 1011/410 cycle sequencing reactions were 94° C., 30 sec (1 min. first cycle); 52° C., 25 sec; 72° C., 50 sec, for 25 Note: the reaction for 1011/410 took advantage of internal primers to reduce non-specific amplification of the initial PCR reaction.

Exochitinase. A genomic library of *Fusarium sporotrichioides* was constructed in phage Lambda λgt11 as described in Huynh et al. 1984. The 5' portion of the exochitinase gene (FIG. 3) was amplified from the *F. sporotrichioides* library (0.5 μg of DNA in a 20 μL reaction) with primers 129, corresponding to sequence located upstream of the EcoRI site of the λgt11 cloning vector (Huynh et al. 1984), and 1003, corresponding to the exochitinase cDNA. PCR conditions for the 129/1003 reaction were 94° C., 30 sec (1 min. first cycle); 52° C., 25 sec; 72° C., 135 sec, for 25 cycles. The resulting PCR product was purified from an agarose gel. Nucleotide sequence data of the PCR product (5' portion of the exochitinase gene) was obtained with primers 128, corresponding to sequence located upstream of the EcoRI site of λgt11, and 1009, corresponding to the exochitinase cDNA. PCR conditions for the 128/1009 cycle sequencing reactions were 94° C., 30 sec (1 min. first cycle); 52° C., 25 sec; 72° C., 50 sec, for 25 cycles. Note: the second PCR reaction (128/1009) took advantage of internal primers to reduce background from the initial PCR reaction.

Example 11

Assembly of Full-Length Endochitinase and Exochitinase cDNA Sequences

Overlaps in the nucleotide sequences of the partial cDNAs and the corresponding 5' PCR products were detected both by visual examination and by analysis of open reading frames using MapDraw (DNASTAR, Inc, Madison, Wis.). For the *F. venenatum* full-length endochitinase, a composite was assembled directly from the partial cDNA sequence and from the sequence of the 5' cDNA PCR product. The full-length exochitinase cDNA represents a composite of the *F. sporotrichioides* 5' genomic sequence adjoined to the partial *F. venenatum* cDNA sequence. The transcriptional start of the exochitinase message is hypothesized to be the first A nucleotide following the putative TATAA consensus element.

Example 12

Generation of Full-Length cDNAs with Modified Start Codon Contexts

A 930 bp, full-length glucanase cDNA with an AC-rich 5' untranslated region was obtained by PCR amplification. The PCR amplification reaction consisted of: 50 ng of glucanase plasmid DNA cleaved with EcoRi, 0.4 uM GLUC 3' and GLUC 5' primers (Table 2), 0.2 uM of each deoxyribonucleotide (dATP, dCTP, dGTP, TTP), and 1 Unit of Elongase (Gibco BRL, Rockville, Md.) in a total volume of 50 $\mu$L buffer (60 mM TRIS sulfate, pH 9.1, 18 mM ammonium sulfate, 1 mM magnesium sulfate). PCR was carried out for 5 cycles at 92° C. for 30 sec, 57° C. for 30 sec, 68° C. for 60 sec followed by 25 cycles at 92° C. for 30 sec, 62° C. for 30 sec, 68° C. for 60 sec.

Full-length cDNAs of the endochitinase and exochitinase were obtained by PCR amplification of genomic DNA fragments using ENDO 3' plus ENDO 5' primers or EXO 3' plus EXO 5' primers, respectively (Table 2). The final step in generating the full-length endochitinase cDNA was accomplished in a 100 4 $\mu$L reaction using 32 pmol each of primers ENDO 5' and ENDO 3'. Amplification was performed with approximately 0.5 $\mu$g of *F. venenatum* cDNA library "A" and Pfu polymerase (Stratagene, La Jolla, Calif.) in Pfu buffer according to the manufacturer's protocol. Conditions for amplification were: 94° C., 30 sec (1 minute for the first cycle); 56° C., 25 sec; 72° C., 150 sec, for 25 cycles. The PE 2400 thermocycler (Perkin Elmer) was used. The fragments were cloned into bacterial and monocot expression vectors as described in Examples 6 and 17, respectively.

PCR amplification of the exochitinase full-length cDNA was accomplished in a 100 $\mu$L reaction using 32 pmol each of primers EXO 5' and EXO 3'. Amplification of *F. venenatum* cDNA library "A" (approx. 0.5 $\mu$g) was performed with Pfu (Stratagene, La Jolla, Calif.) in Pfu buffer according to the manufacturers' protocol, using a PE 2400 thermocycler (Perkin Elmer). PCR conditions were 94° C., 30 sec (1 min first cycle); 56° C. 25 sec; 72° C., 150 sec, for 25 cycles. The resulting PCR product was gel-purified and cloned into bacterial and monocot expression vectors, as described in Examples 6 and 18.

cDNA fragments were separated from unincorporated primers and from other PCR products by partitioning on agarose gels (Example 8). PCR products of the desired size (930 bp for glucanase, 1240 bp for endochitinase, 1780 bp for exochitinase) were excised from gels with a clean razor blades, then recovered from the gel segments by adsorption onto silica beads (GENECLEAN Spin Kit, BIO 101, Inc., Vista, Calif.) as recommended. cDNA fragments were eluted from the silica matrix with water and stored at −20° C. for subsequent cloning (Examples 16–18).

Example 13

Construction of the Monocot Expression Vector pUBKBglII-

Removal of the BglII restriction enzyme recognition site in the Ubi-1 promoter region of pUBK was carried out using the QuikChange™ Site-Directed Mutagenesis Kit and protocols (Stratagene, La Jolla, Calif.). pUBK plasmid DNA (50 ng) was suspended in a reaction mixture of: 125 ng primer UBI 1E (Table 2), 125 ng primer UBI 1F (Table 2), 10 mM of each deoxynucleotide, and 2.5 Units of Pfu polymerase in a total volume of 50 $\mu$L 20 mM TRIS chloride, pH 8.0, 10 mM potassium chloride, 6 mM ammonium sulfate, 2 mM magnesium sulfate, 0.1% Triton X-100, and 10 $\mu$g/mL bovine serum albumin. PCR was performed with a DNA Thermal Cycler (Perkin Elmer Cetus, currently Foster City, Calif.) and an amplification protocol of 16 cycles of 96° C. for 30 sec, 55° C. for 60 sec, 68° C. for 13 min. The resulting amplified products were treated with 10 Units of Dpn I restriction enzyme for 1 hour at 37° C. Competent *E. coli* XL1-Blue host cells were incubated on ice with 1 $\mu$L of the Dpn-treated PCR mix for 30 minutes, immediately transferred to a water bath at 42° C. for 45 sec, then placed on ice for 2 minutes. Cells were suspended in 0.5 mL of liquid medium containing 1% (w:v) NZ amine, 0.5% (w:v) yeast extract, 0.5% (w:v) sodium chloride, 20 mM glucose, 12.5 mM magnesium chloride, and 12.5 mM magnesium sulfate. Cells were incubated at 37° C. for 1 hour with agitation at 225 rpm. Cells were concentrated by centrifugation at 4° C., 1700×g for 3 minutes, then spread onto an LB agar plate containing 50 Atg/mL kanamycin sulfate.

Bacterial colonies showing growth on LB-kanamycin were cultured in 1.5 mL of liquid LB-kanamycin for plasmid DNA isolation as described in Example 7. Plasmid DNA was treated with Bgl II restriction enzyme and the cleavage products visualized in an agarose gel as described in Example 8. A single fragment was obtained, indicating that one of the two Bgl II sites in pUBK had been ablated in the mutagenized plasmid. Nucleotide sequence data of a portion of the Ubi-1 promoter region spanning the mutated site was obtained as described in Example 9 with primer UBI 1B (Table 2). In addition to the conversion of the AGATCT (BglII site) to AGATTT, a 29 bp duplication of a portion of the Ubi-1 promoter was also noted (see FIG. 5).

The mutagenized plasmid was further treated with BamHI+BglII, PstI and PvuII restriction enzymes as recommended by the manufacturer, and the cleavage products visualized on an agarose gel as described in Example 8. The mutagenized plasmid lacked about 0.7 kb of DNA that was present in pUBK prior to site-directed mutagenesis. To correct this deletion, a 2.0 kb portion of the mutagenized plasmid was excised with HindIII and BamHI restriction enzymes, then ligated to pUBK from which the native HindIII-BamHI fragment had been removed. The ligation reaction contained approximately 50 ng of 2.0 kb fragment, 50 ng of pUBK vector, 0.5 Units of T4 DNA ligase in 10 $\mu$L of 50 mM TRIS chloride, pH 7.8, 10 mM magnesium chloride, 10 mM dithiothreitol, 2 mM ATP, and 50 $\mu$g/mL bovine serum albumin. The reaction was incubated at 15° C. for 17 hours. Electrocompetent *E. coli* NM522 cells were subjected to electroporation in the presence of 1 $\mu$L of the ligation mixture and further treated as described in Example 6. Six kanamycin-resistant bacterial colonies were individually cultured in 1.5 mL LB-kanamycin for plasmid isolation as described in Example 7. As expected, these plasmids gave 4.5 kb and 2.0 kb fragments upon digestion with HindIII+ BamHI, and a single fragment of about 6.6 kb following BglII treatment. One plasmid, called the monocot expression vector, was selected for subsequent cloning experiments.

Example 14

Activity of the Modified Ubi-1 Promoter in Organs of Wheat

To test the activity of the Ubi-1 promoter following mutagenesis, the 2.0 kb HindIII-BamHI fragment (Example 13) carrying the mutant region was substituted for the original region in a plasmid carrying a Ubi-1-betaglucuronidase gene (uidA) fusion, such that the GUS reporter gene was under regulation of the modified Ubi-1 promoter. This plasmid was introduced into embryos of *Triticum aestivum* (wheat), using procedures described in Example 19. The organs of the floret of uidA transgenic lines were tested for β-glucuronidase (GUS) activity.

Whole heads of transgenic wheat carrying at least 1 copy of the Ubi::uidA transgene were surface-sterilized by treatment in 70% ethanol for 5 minutes and 20% (v/v) bleach for 15 minutes. Whole heads were rinsed 4 to 5 times in distilled water that had either been autoclaved or passed through 0.2 micron Millipore filter membranes. Florets were dissected in a sterile hood such that glumes, lemmas, paleas, developing seeds and anthers were separated. The floret organs were immediately immersed in a substrate solution containing 10 mM sodium phosphate buffer, pH 7, 0.5 mM potassium ferrocyanide, 0.5 mM potassium ferricyanide, 0.5% (w:v) Triton X-100, and 330 µg/mL 5-bromo-4-chloro-3-indoyl-beta-D-glucuronide (Jersey Lab and Glove Supply, Livingston, N.J.). After 16–20 hours of incubation in darkness, the substrate solution was withdrawn. The plant materials were rinsed twice with 0.1 M sodium phosphate buffer, pH 7. Chlorophyll and other pigments were removed from the green tissues by successive immersions in 70%, 80% and 90% ethanol solutions, 20–24 hours per solution. Treatments with 90% ethanol were repeated until the tissues appeared translucent and nearly white. Activity of the GUS gene was evident as a dark blue pigment within the developing seed and pollen of wheat, indicating that the modified Ubi-1 promoter was active in these organs. GUS activity was also detected in the chlorophyll-containing cells and tissues of the glume, lemma and palea. No GUS activity was seen in the brush or in the anther.

Example 15

Introduction of Modified Full-Length cDNAs into Bacterial Cloning Vectors

PCR products representing full-length cDNA fragments of the glucanase, endochitinase, and exochitinase, with 15 to 16 bases of AC-rich 5' untranslated sequence, were mobilized into either pCR2.1 (Invitrogen, Carlsbad, Calif.; for glucanase) or Bluescript vector pBKS+(Stratagene, La Jolla, CA; for endochitinase and exochitinase). Ligations were carried out as described in Example 13 with approximately 50–100 ng of bacterial vector DNA that was previously treated with SmaI restriction enzyme, and 60 ng of the PCR product. Transformations of *E. coli* NM522 host cells (for glucanase) or DH5-alpha host cells (for endochitinase and exochitinase) were carried out as described in Example 6. Transformants were selected on LB agar plates containing 100 µg/mL carbenicillin.

To facilitate the identification of transformants carrying the endochitinase and exochitinase cDNAs, colony blot hybridizations were performed (Sambrook et al., 1989). Carbenicillin-resistant colonies were transferred in an ordered array to both fresh agar plates and to 82 mm disks of Hybond N+ nylon membrane (Amersham) laid atop LB-carbenicillin agar. Transferred colonies were grown at 37° C. for 16–18 hours. Nylon disks with colonies were placed on a sheet of 3MM (Whatman) paper that was saturated with 0.5 N sodium hydroxide, 1.5 M sodium chloride for 5 minutes, blotted briefly on clean paper, then transferred to paper saturated with 0.5 M TRIS-Cl, pH 7.0, 3 M sodium chloride for 5 minutes. The colony disks were submerged in 2×SSC (0.3 M sodium chloride, 0.03 M sodium citrate, pH 7.0) for 10 minutes with agitation at 60–70 rpm to loosen bacterial debris, rinsed in fresh 2×SSC and dried in air. The colony disks were incubated in glass tubes in a Hybaid hybridization oven (National Labnet, Woodbridge, N.J.) at 65° C. for 17 to 18 hours in 20 mL of a hybridization solution containing 5×SSC, 0.1% (w:v) sodium lauryl sarcosine, 0.02% (w:v) sodium dodecyl sulfate, and blocking reagent (Boehringer Mannheim). Colony disks were transferred to 10 mL of fresh hybridization solution containing 20–25 ng of heat-denatured probe and incubated at 65° C. for 16 to 20 hours in the hybridization oven. Digoxygenin-labeled hybridization probes were made with ~100 ng of the endochitinase and exochitinase PCR products and 4 µL of DIG HighPrime mix in a final volume of 20 µL (Boehringer Mannheim), incubated at 37° C. for 16 to 20 hours. Unincorporated label was removed by precipitation of the probe DNA in 0.5 M lithium chloride and 2.5 volumes of 95% or 100% ethanol at −80° C. for 20 minutes. Probe DNA was resuspended in water for use in hybridization solutions. Hybridized filters were washed in the hybridization tubes as follows: two washes of 50 mL 2×SSC, 0.1% SDS at room temperature for 5 minutes and two washes of 50 mL 0.5×SSC, 0.1% SDS, 65° C. for 25 minutes. Filters were transferred to 1 L beakers and incubated at 70 to 75 rpm, room temperature in: 100 mL 0.1 M maleic acid, 0.15 M sodium chloride, pH 7.5, 0.3% (v:v) Tween 20; 100 mL 0.1 M maleic acid, 0.15 M sodium chloride, pH 7.5, and 0.1 volumes of blocking solution, 30 minutes; 40 mL 0.1 M maleic acid, 0.1 5M sodium chloride, pH 7.5, 0.1 volumes of blocking solution, and 4µL anti-DIG-AP conjugate (Boehringer Mannheim); two washes of 100 mL 0.1 M maleic acid, 0.1 5M sodium chloride, pH 7.5, 0.3% (v:v) Tween 20, 15 minutes each; 40 mL 0.1 M TRIS-Cl, pH 9.2, 0.1 M sodium chloride, 5 minutes. DIG hybridization to colonies on the filters was detected with CSPD reagent (Boehringer Mannheim) and subsequent exposure on XAR 5 scientific imaging film (Kodak, Rochester, N.Y.).

Candidate glucanase cDNA clones were treated with BamHI+BglII, Eco RI or EcoRV; candidate endochitinase cDNA clones were treated with BamHI, Bgl II, and BamHI+BglII; candidate exochitinase cDNA clones were treated with BamHI, Bgl II, BamHI+BglII, ClaI, and XhoI. The restriction enzyme digestion patterns indicated that all three cDNAs had been cloned in both orientations within the bacterial plasmid vectors, and that a BamHI and a BglII site had been added to each cDNA.

To verify the fidelity of the polymerase chain reaction and cloning, nucleotide sequences of both strands of each cDNA were obtained by automated fluorescent sequencing as described in Example 9 (see SEQ ID NOS. 16, 18, and 20). Double-stranded sequences of the cDNAs were analyzed for the presence of restriction sites as described in Part 3, and for matches to entries in the GenBank database with BLASTX.

Example 16

Introduction of the Modified Full-Length Glucanase cDNA into the Monocot Expression Vector PCR-modified cDNAs having nucleotide sequences identical to the original cDNAs were introduced into a monocot expression vector, pUBKBglII-, for use in wheat transformation experiments. The monocot expression plasmid vector was digested extensively with BamHI and BglII restriction enzymes. The pUBKBglII-plasmid vector DNA was purified by partitioning on agarose as described in Example 8.

A glucanase clone in which the 5' end of the glucanase coding sequence was inserted proximal to the T7 promoter and M13 forward primer sites of pCR2.1 was selected to generate the modified glucanase cDNA. The modified glucanase cDNA was excised from pCR2.1 by partial digestion with BamHI restriction enzyme as a follows: In a 1.5 mL conical bottom tube, 25 μg of glucanase plasmid DNA was suspended in 125 μL of 150 mM sodium chloride, 10 mM TRIS-Cl, pH 7.9, 1 mM magnesium chloride, 1 mM dithiothreitol, and 100 μg/mL bovine serum albumin. Thirty microliter aliquots of the mixture were dispensed to two other tubes. To the mix remaining in the first tube, 10 Units of BamHI enzyme was added and thoroughly mixed. Then, 30 μL of the plasmid-restriction enzyme mixture was added to a tube containing 30 μL of plasmid mix without Bam HI restriction enzyme, and mixed thoroughly. The resulting solution was diluted about two-fold for BamHI enzyme. A sequential dilution of the enzyme mix to about 1:4 was carried out with the second tube of plasmid mix (without BamHI enzyme). Incubation of all 3 tubes was performed at 37° C. for 85 minutes. Four different DNA fragments representing partial BamHI digestion products were visualized on a 1% agarose gel. About 6 to 8 μg of plasmid DNA from the digestion mixture containing 1:4 diluted Bam-HI was partitioned on 1% agarose. A fragment of about 1 kb carrying the modified glucanase cDNA was excised from the agarose gel and purified on silica beads as described in Example 12.

About 36 ng of the glucanase cDNA fragment and 220 ng of pUBKBglII-vector DNA, digested with BamHII and BglII, were ligated in 10 μL at 15° C. for 22 hours. Two microliters of the ligation mixture was used to transform *E. coli* host DH5-alpha as described in Example 6. Bacterial colonies were selected for growth on LB agar containing 50 μg/mL kanamycin. Cells were prepared from 1.5 mL liquid cultures as described in Example 7. Plasmid DNA and pUBKBglII- DNA were partitioned on 1% agarose at 69V for about 1 hour. Plasmids that showed slower migration in the agarose gel were further treated with BamHI+BglII or BamHI restriction enzymes. Insertion of the modified glucanase CDNA in the sense orientation with respect to the Ubi-1 promoter gave BamHI fragments of 0.55 kb in size, and were distinguishable from the antisense orientation of the cDNA, which resulted in a 0.39 kb BamHI fragment.

Figure 6:
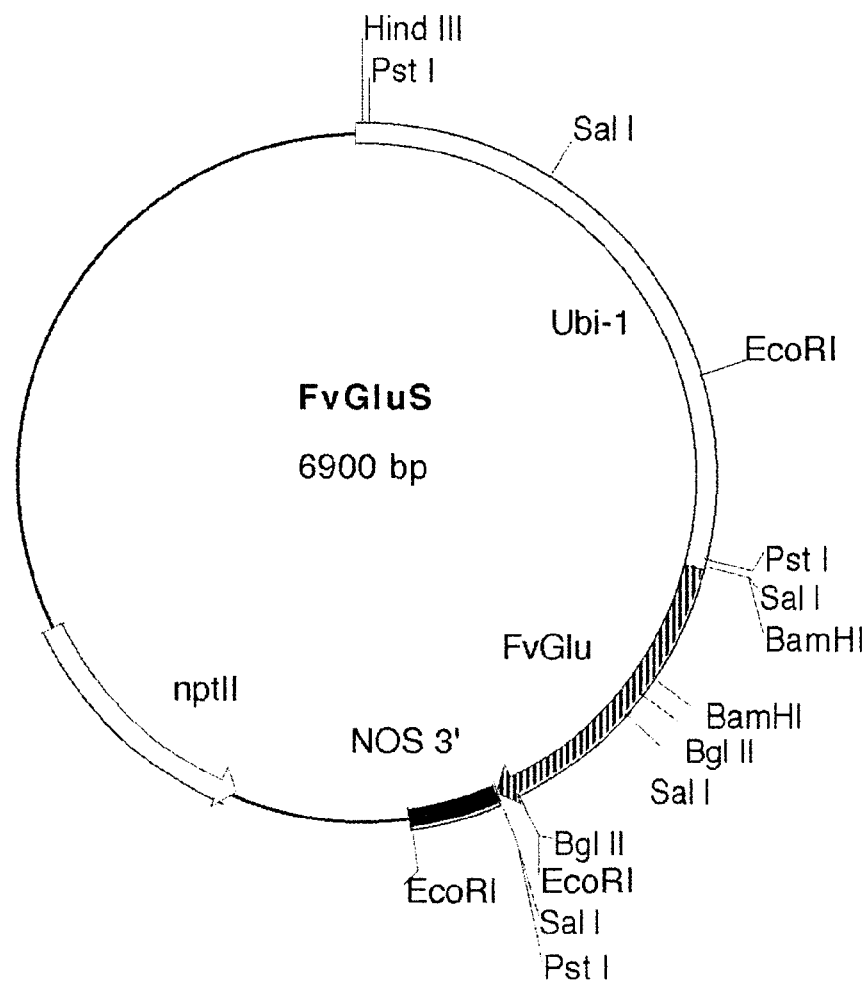
Figure 7:
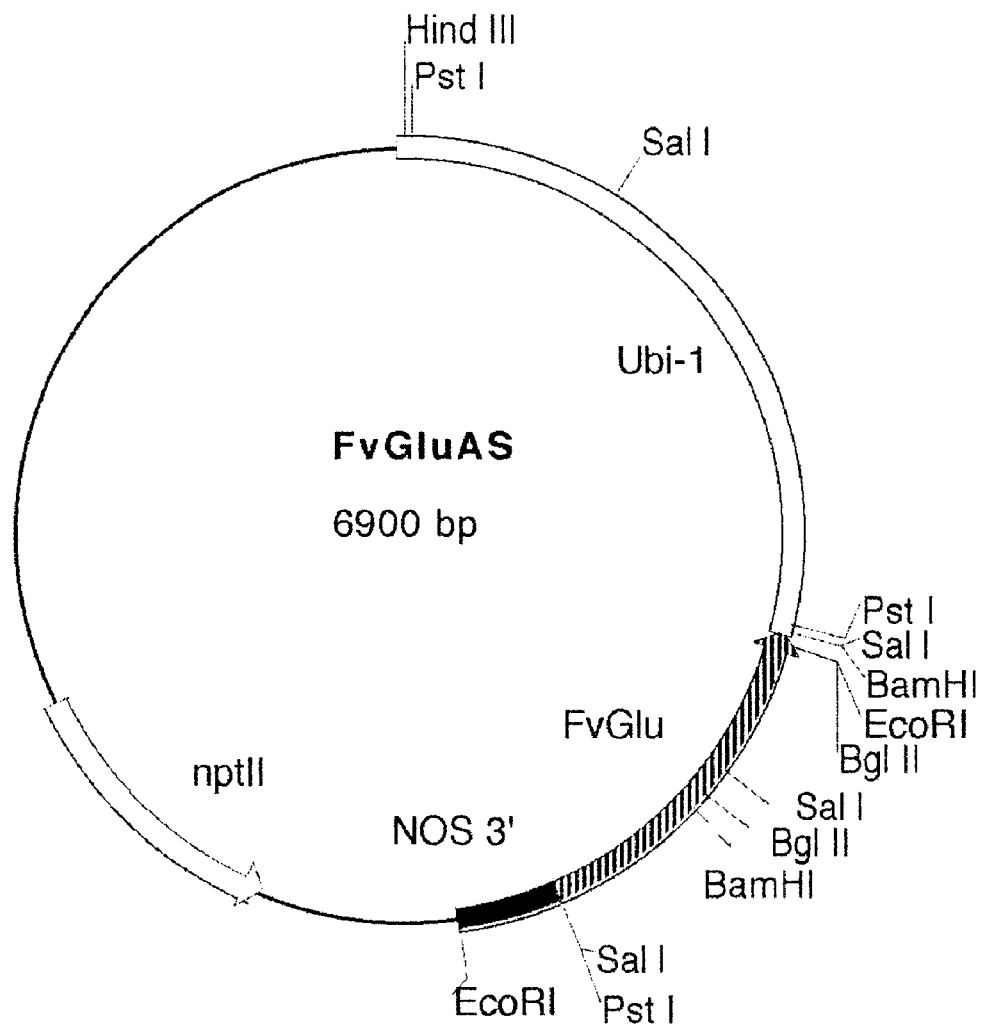

Several clones representing each orientation were selected for nucleotide sequence verification. The junction of the Ubi-l promoter-glucanase gene fusion (Ubi::Glu) was sequenced with primer UBI 1A (see Table 2); the glucanase gene-NOS terminator fusion (Glu::NOS) was sequenced with primer NOS A (see Table 2). Sequences of representative sense and antisense clones of the modified glucanase cDNA are given. In the sense orientation, a BamHI site at the Ubi-1 junction is present at the 5' end of the cDNA (FIG. 6). A BglII site, and 47 bp of DNA from the polylinker region of pCR2.1 containing an EcoRI site, are present at the 3' end. In the antisense orientation, the BamHI site at the Ubi-1-cDNA junction is followed by 47 bp of the pCR2.1 polylinker region (with an EcoRI site), then the BglII site that occurs at the 3' end of the modified glucanase cDNA (FIG. 7). The antisense version contains a chimeric non-functional BamHI-BglII site at the cDNA-NOS terminator junction.

Example 17

Introduction of the Modified Full-Length Endochitinase cDNA into the Monocot Expression Vector The modified full-length endochitinase cDNA was obtained from a clone in which the 5' end of the coding sequence was proximal to the T7 promoter site of pBKS+. About 4 μg of plasmid DNA was cleaved extensively with 30 Units of BamHI and 30 Units of BglII restriction enzymes in 50 μL of 150 mM sodium chloride, 10 mM TRIS-Cl, pH 7.9, 1 mM magnesium chloride, 1 mM dithiothreitol, and 100 μg/mL bovine serum albumin. The cDNA fragment was recovered from the agarose gel by partitioning on silica beads as described in Example 12. Ligation of 90 ng of cDNA fragment and 440 ng of pUBKBglII-, digested with BamHI and BglII, was carried out in 15 μL as described in Example 13. *E. coli* DH5-alpha cells were transformed with 3 μL of the ligation mixture (see Example 6) and grown at 37° C. in the presence of 50 μg/mL kanamycin sulfate. Plasmid DNA was extracted from candidate kanamycin-resistant colonies. Plasmids that migrated more slowly than pUBKBglII- on agarose gels were cleaved with BamHI and BglII restriction enzymes. A ~1.2 kb fragment was seen in some (sense orientation) clones. The absence of any cleavage by BamHI+BglII was expected for antisense clones.

Figure 8:
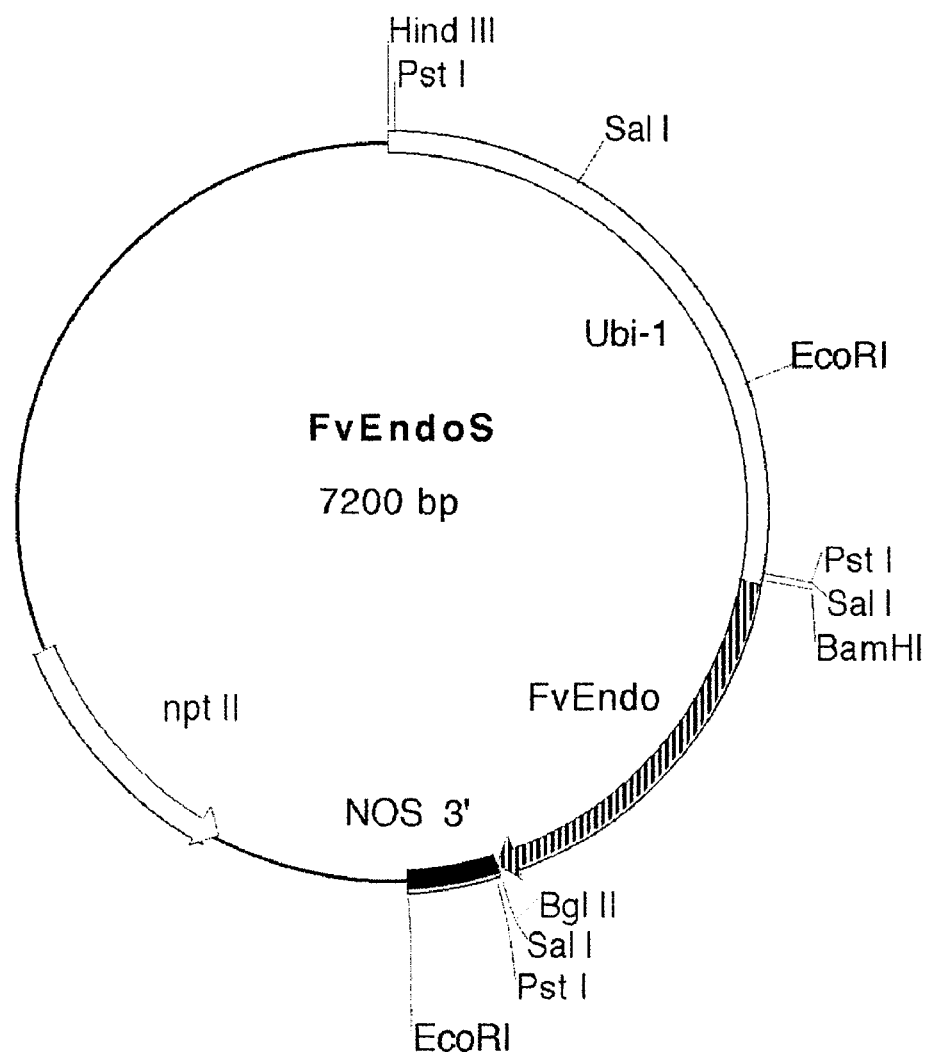
Figure 9:
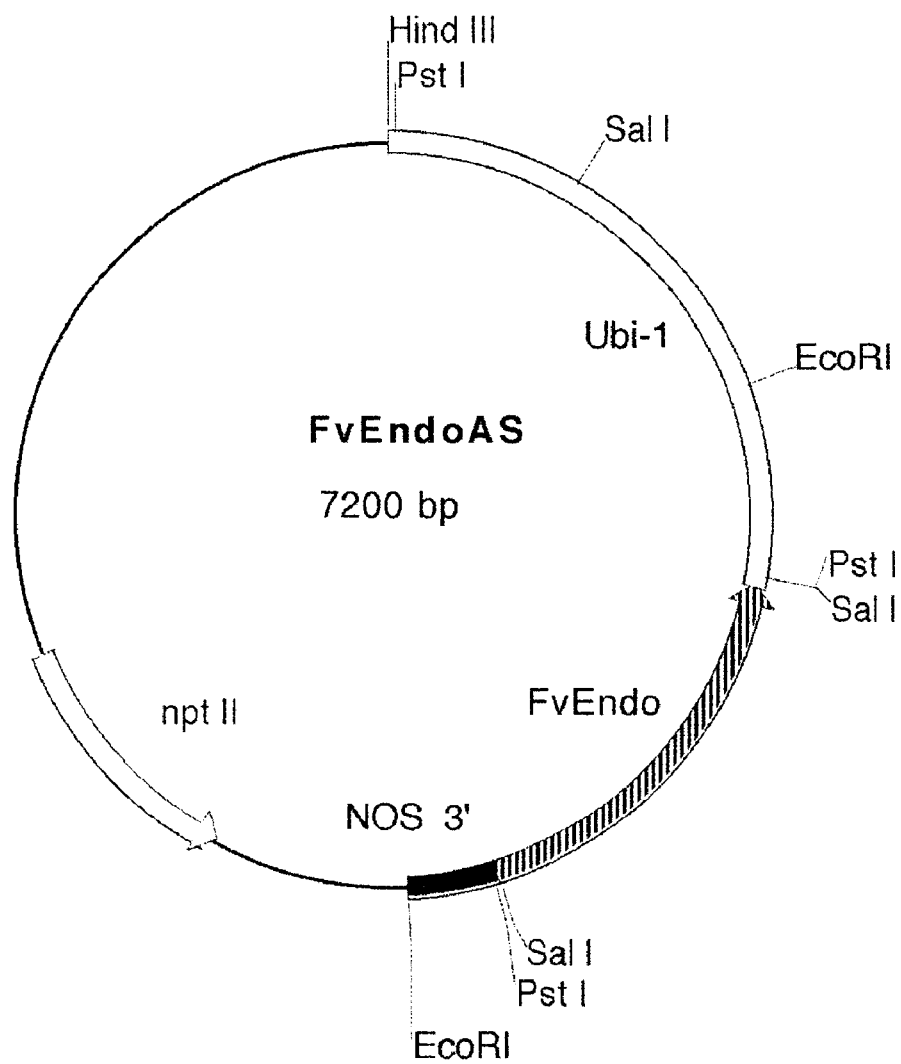

The junctions of the Ubi-1 promoter-endochitinase cDNA fusion of several clones were sequenced with primer UBI 1A (see Table 2); the endochitinase cDNA-NOS terminator fusion was sequenced with primer NOS A (see Table 2). Representative sense and antisense orientations of the cDNA in pUBKBglII- are shown in FIGS. 8 and 9, respectively. The sense clone of the endochitinase contains a BamHI restriction site at the Ubi-1-coding sequence junction and a BglII restriction site at the cDNA-NOS junction. BamHII and BglII sites are absent in the endochitinase antisense clone.

Example 18

Figure 10:
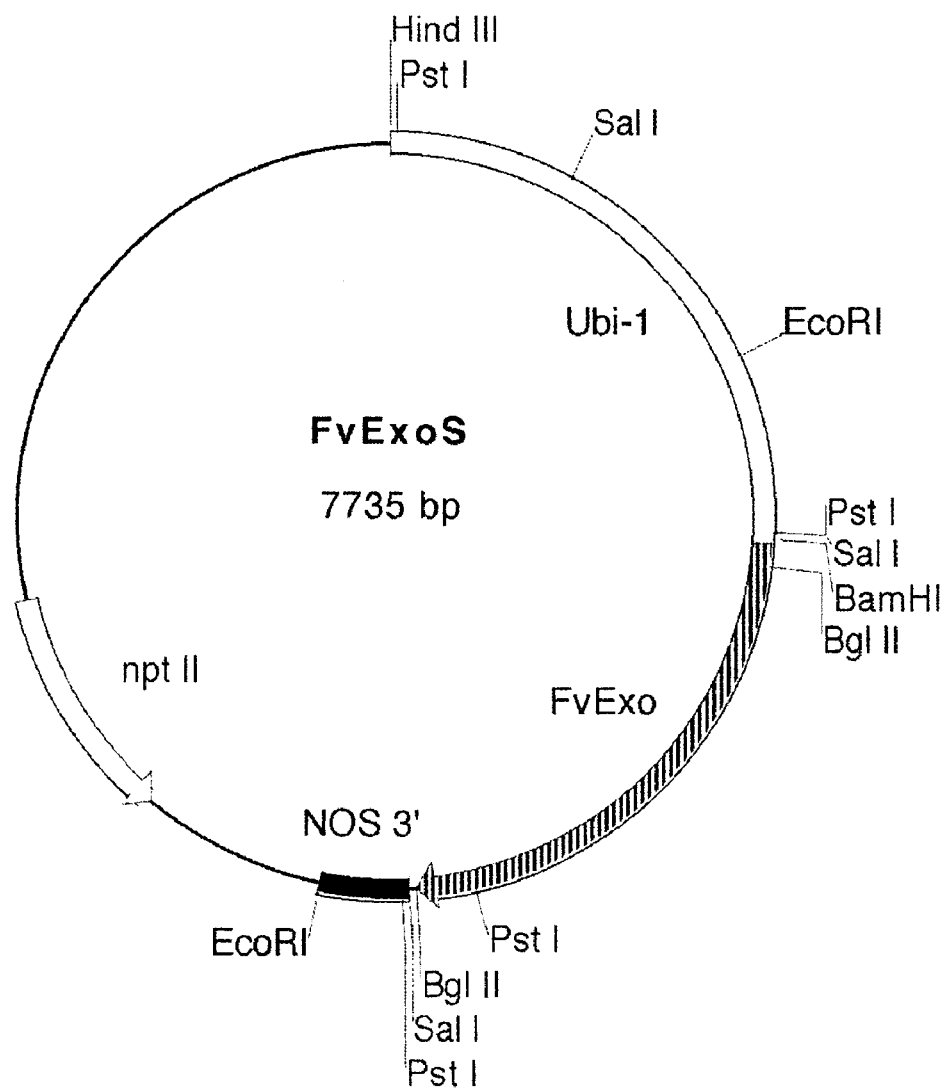
Figure 11:
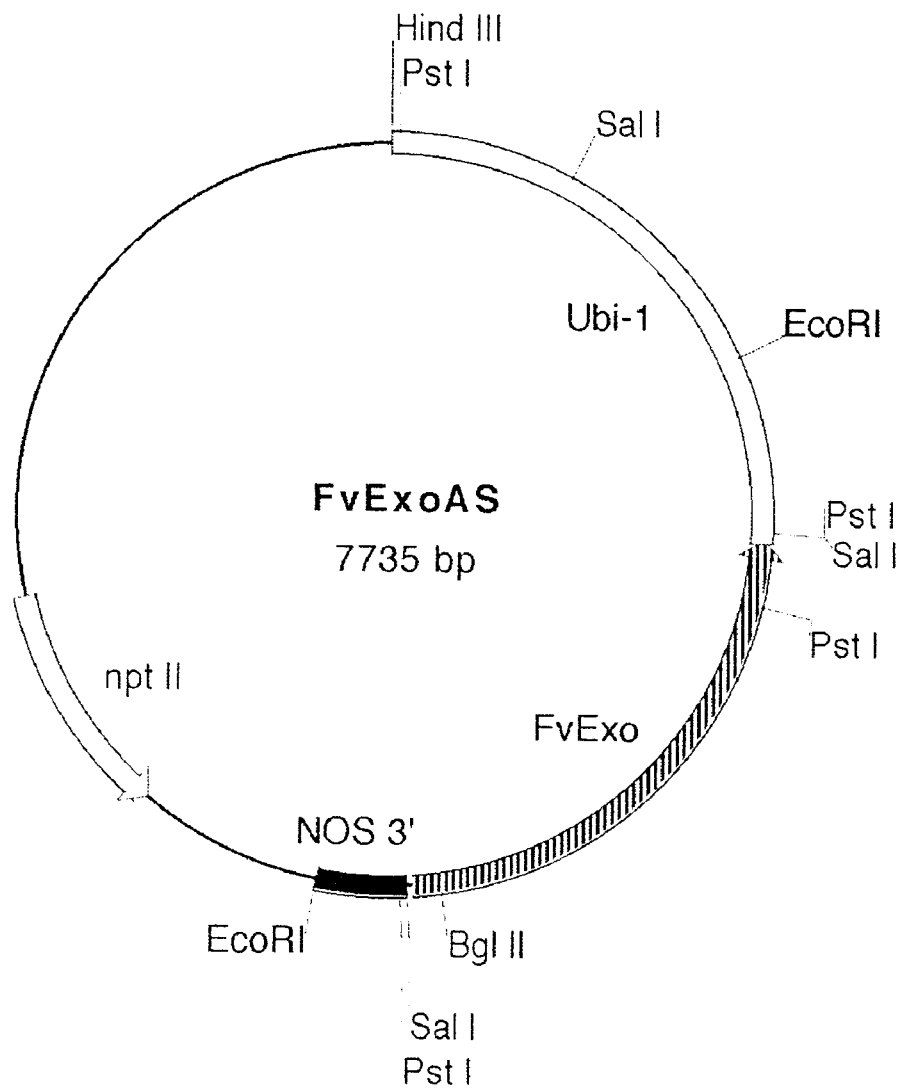

Introduction of the Modified Full-Length Exochitinase cDNA into the Monocot Expression Vector To obtain the modified exochitinase cDNA, an exochitinase clone was selected in which the 5' end of the exochitinase coding sequence was proximal to the T3 primer site in pBKS+. About 3 μg of plasmid DNA was treated with 20 Units of BamHI in a final volume of 30 μL 150 mM sodium chloride, 10 mM TRIS-Cl, pH 7.9, 1 mM magnesium chloride,1 mM dithiothreitol, and 100 μg/mL bovine serum albumin at 37° C. for 90 minutes. A DNA fragment of about 2.0 kb was purified from an agarose gel as described in Example 8. The ligation mixture contained about 60 ng of the cDNA fragment and 220 ng of pUBKBglII- DNA (see Example 16). Transformants of *E. coli* DH5-alpha were generated and grown as in Example 15. Plasmid DNA that migrated slower than the pUBKBglII- vector was subjected to nucleotide sequence analysis (Example 9) using UBI 1A and NOS A primers to determine the orientation of the coding sequence within pUBKBglII-. Additional exochitinase clones were identified using the colony blot procedure (see Example 15). Representative sequences for the sense and antisense orientations of the exochitinase cDNA in pUBKBglII- are shown in FIGS. 10 and 11, respectively. The sense clone of the exochitinase contains a BamHIII restriction site at the Ubi-1-coding sequence junction and a BglII restriction site at the cDNA-NOS junction. These BamHI and BglII sites are absent in the exochitinase anti-sense clone.

Example 19

Transformation of Wheat (*Triticum aestivum*) with the Fungal Transgenes

The method of Weeks et al. (1993) was used to introduce the modified full-length cDNA clones (in the monocot expression vector, pUBKBgIII-) into wheat, but with following additions and modifications. Embryos were excised from seeds of *T. aestivum* cultivar Bobwhite at about 10–12 days post anthesis (dpa). Embryos were placed scutellum-side up onto 15 mm×100 mm plates containing 30 mL of MMS medium [4.3 g/L Murashige & Skoog salt mixture (Gibco BRL, Rockville, Md.), 0.5 mg/L thiamine hydrochloride, 0.15 g/L L-asparagine, 40 g/L maltose] solidified with 3.5 g/L Phytagel (Sigma Chemical Co., St. Louis, Mo.) and supplemented with 2 mg/L 2,4-D. The embryos were incubated at 25° C. in darkness for 5 days to allow development of callus and then transferred to 15 mm×60 mm plates containing 20 mL of the above medium supplemented with 0.35 M mannitol. After 4 hours on mannitol-containing medium, embryos were subjected to bombardment with 0.7 mg per plate of 1–2 micron (average diameter) particles of gold (Bio-Rad, Hercules, Calif.) coated with 17.4 $\mu$g of pUBKBgIII- and 19.5 $\mu$g of FvEndoS or with 15.5 $\mu$g pUBKBglII- and 16.2 $\mu$g of FvGluS or with 12.5 $\mu$g pUBK and 22.6 $\mu$g FvExoS. The next day, embryogenic calli were transferred to "MMS2" medium (MMS media supplemented with 2 mg/L 2,4 D and solidified with 2.5 g/L Phytagel). The calli were placed at a density of 20 (FvGluS) or 40 (FvEndoS and FvExoS) per plate and incubated at 25° C. in darkness for two weeks. The calli were then selected for two 2-week periods by incubation in darkness at 25° C. on plates containing MMS2 media supplemented with the following additions: for FvEndo, 0 or 1 mg/L bialaphos (Meiji Seika Kaisha Ltd., Tokyo, Japan), then 2 mg/L bialaphos; for FvExoS 1 or 1.5 mg/L, then 3 mg/L bialaphos; for FvGluS, 1 mg/L, then 2 mg/L bialaphos. The surviving calli were then transferred to MMS media solidified with 2.5 g/L Phytagel and containing 0.2 mg/L 2,4-D and 3 mg/L bialaphos and incubated in the light at 26° C. for six weeks. Green shoots that formed during this time were transferred to 25×150 mm test tubes containing 18 mls of rooting medium [2.15 g/L Murashige & Skoog salt mixture, 0.25 mg/L thiamine hydrochloride, 0.075 g/L L-asparagine, 20 g/L maltose, 2.5 g/L Phytagel]. The tubes were incubated in the light at 26° C. Shoots that formed roots were transferred to soil (Sunshine mix#1) and incubated in the light at 22° C. under saran wrap for one week. Humidity was lowered by poking an increasing number of holes in the saran wrap during a second week of incubation. The plants were then transplanted to the greenhouse maintained at 23° C. with supplemental lights set for 16/8-hour day/night cycle. Immature embryos about 21 dpa were excised from the seeds of these plants and precociously germinated in magenta boxes containing 100 mls of MMS medium solidified with 2.5 g/L phytagel.

Example 20

Analysis of Wheat Lines for Stable Incorporation of the Transgenes

Genomic DNA or total DNA was extracted from wheat leaves to analyze candidate lines for stable incorporation of the modified, full-length glucanase, endochitinase and exochitinase cDNA constructs. Untransformed plants of the cultivar Bobwhite were sampled as negative controls.

Genomic DNA was prepared by a modified method of d'Ovidio et al. (1992). Three to five grams fresh weight of healthy leaf tissue was excised from the plant, placed on ice immediately, then in liquid nitrogen, or placed directly in liquid nitrogen. Leaf samples were often stored at –80° C. prior to extraction of genomic DNA. Leaf tissue was ground with a chilled mortar and pestle in the presence of liquid nitrogen. Powdered tissue was transferred to 35–40 mL of chilled homogenization buffer containing 0.5 M sucrose, 80 mM potassium chloride, 10 mM TRIS-chloride, 10 mM EDTA, 4 mM spermine, 1 mM spermidine, pH 9.5, 180 mg/L phenylmethylsulfonyl fluoride (added immediately before use), and 0.1% (v:v) beta-mercaptoethanol (added immediately before use). The leaf material was further homogenized with three to four 5-second pulses in a chilled blender. The homogenate was filtered through four layers of cheesecloth, followed by one layer of Miracloth filtration material (Calbiochem, La Jolla, Calif.). The clarified extract was centrifuged at 1000×g for 20 minutes at 4° C. The supernatant was carefully decanted and the pellet containing nuclei washed twice in 20 to 40 mL homogenization buffer supplemented with 0.5% Triton X-100 (Sigma Chemical Co., St. Louis, Mo.). The washed nuclei pellet was resuspended in 1 mL of a buffer solution containing 50 mM TRIS-chloride, pH 8, 100 mM EDTA, 100 mM sodium chloride, and 600 $\mu$g of proteinase K. An additional 4 mL of buffer, pre-warmed to 65° C. without proteinase K, was added. The homogenate was incubated at 65° C. for 30 minutes and then at room temperature (23°–25° C.) for 30 minutes prior to thorough mixing with 2.5 mL phenol (equilibrated with TRIS buffer, pH 7.9). After the DNA-phenol mixture was placed at 4° C. for 12–16 hours, 2.5 mL of chloroform was added and mixed thoroughly. The extract was centrifuged at 4000×g at room temperature for 15 minutes. The aqueous (upper) phase was extracted twice more with chloroform. DNA was precipitated in 0.1 volume of 2.5 M sodium acetate, pH 5.2, and 0.7 volumes of isopropyl alcohol at room temperature. DNA was recovered with a glass rod, then resuspended in water for 1 to 3 days at 4° C.

Total DNA was isolated from 1 to 1.5 $cm^2$ sections of leaf tissue by a modified method of Dellaporta et al. (1983). Sections were cut from healthy leaves with clean scissors, placed in 1.5 mL conical microcentrifuge tubes, and transferred directly to liquid nitrogen. Leaf sections were often stored at –80° C. prior to DNA extraction. Leaf tissue was homogenized in liquid nitrogen with a microfuge pestle (Kontes Glass Co., Vineland, N.J.) in the microcentrifuge tube. To a tube of the frozen powder was added 0.5 mL of an extraction buffer containing 50 mM TRIS-chloride, pH 8, 100 mM sodium chloride, 10 mM EDTA, pH 8, 1% sodium dodecyl sulfate, and 10 mM beta-mercaptoethanol (added immediately before use). Before the slurry thawed, the tube was placed in a water bath at 65° C. After thawing, the homogenate was shaken vigorously, incubated at 65° C. for a minimum of 10 minutes and no longer than 25 minutes. Following the addition of 180 $\mu$L of 5 M potassium acetate (Sambrook et al., 1989), the extracts were mixed thoroughly, placed on ice for 10 minutes, then centrifuged at 4° C. for 10 minutes in a TOMY MTX-150 High Speed Micro Refrigerated Centrifuge. The supernatant containing DNA was transferred to a new microcentrifuge tube and DNA was precipitated with 0.5 mL isopropyl alcohol at room temperature for 30 minutes. The DNA pellet was obtained by centrifugation as above; the supernatant was decanted and discarded. The pellet was washed in 250 $\mu$L of 70% ethanol (chilled at –20° C.) and centrifuged at 4° C. for 5 minutes. Residual ethanol was removed with a pipettor, and the washed pellet was dried 3 minutes in a DNA 110 Speed Vac, and dissolved in 50 $\mu$L of water. Best PCR amplification was obtained with freshly-prepared extracts.

For PCR amplification, 200 to 400 ng of genomic DNA or 2 kL of total DNA was brought to 10 $\mu$L with water in a 0.2 mL thin-walled tube (MJ Research, Inc., Watertown, Mass.).

To each sample was added 40 μL of a PCR mixture containing 25 picomoles of UBI A2 primer, 25 picomoles of transgene-specific primer (see Table 3), 50 mM potassium chloride, 10 mM TRIS-chloride, pH 9.0, 0.1% Triton X-100, 3 mM magnesium chloride, 1 mM each of dATP, dCTP, dGTP and TTP, and 2.5 Units of Taq DNA polymerase (Promega, Madison, Wis.). Polymerase chain reaction was carried out on a PTC-100 or PTC-200 Programmable Thermal Controller (MJ Research, Watertown, Mass.) with the following protocol: 96° C. for 30 sec; 35 cycles of 95° C. for 1 minute, 62° C. for 1 minute, 72° C. for 1 minute; 72° C. for 15 minutes; 4° C. soak. PCR products (10–13 μL of each PCR reaction mixture) were partitioned on 1% to 1.6% agarose gels and visualized by ethidium bromide staining and ultraviolet light as described in the Example. Positive PCR controls included 10 to 20 ng of pUBKBglIII- plasmid DNA containing the glucanase, endochitinase or exochitinase cDNAs.

At least three transgenic wheat lines showing amplification of the predicted 425 bp Ubi-exochitinase PCR product, or the predicted 375 bp Ubi-glucanase PCR product, or the predicted 340 bp Ubi-endochitinase PCR product have been obtained in our experiments (FIG. 12).

Transgenic lines were propagated as described in Example 19. Progeny were analyzed for bialaphos resistance and/or for the presence of the *F. venenatum* transgenes using PCR. Populations in which all of the individual progeny were bialaphos resistant and/or were positive in the PCR transgene assay in two successive generations were considered to be derived from a line homozygous for the transgene.

Example 21

Analysis of Transgenic Wheat Lines for Transgene mRNA

Homozygous lines and/or their progeny, identified as described in Example 20, were analyzed for the expression of transgene messenger RNA (mRNA) by northern blot analysis. Seed was harvested from heads at 15–20 days post-anthesis and surface sterilized by immersion in 70% ethanol for 5 min., followed by 20% (v:v) hypochlorite solution for 15 min. Seeds were rinsed 4 to 5 times with sterile water. The embryo was removed from each seed with dissecting forceps, and endosperm material was squeezed from the seed coat with the flat side of a metal spatula. The endosperm was frozen in liquid nitrogen as it was harvested, and pooled endosperm material from 15–30 seeds was stored at −80° C. prior to RNA isolation. Total RNA was isolated using a modified method of Altenbach (1998). Essentially, frozen endosperm was ground to a fine powder in a chilled mortar and pestle, in the presence of liquid nitrogen. The frozen homogenate was transferred to a 50-mL conical centrifuge tube containing 5 mL extraction buffer (10 mM sodium chloride, 10 mM TRIS-Cl, pH 9.0, 1 mM EDTA), 2.5 mL phenol (saturated with TRIS buffer at pH 4.3, Fisher #BP1751), and 2.5 mL chloroform. The tube was inverted 40 times, then centrifuged at 6500 rpm, 4° C. for 10 minutes in a Sorvall HS-4 rotor. The aqueous phase was transferred to a fresh tube, extracted once with an equal volume of phenol/chloroform (1:1 v/v), and once with an equal volume of chloroform. The mixture was centrifuged after each extraction as described. To the aqueous extract, 8M LiCl was added to give a final concentration of 2M LiCl and incubated at −20° C. overnight. The precipitate containing RNA was collected by centrifugation at 12,500 rpm, 4° C. for 30 minutes in a Sorvall SS-34 rotor. The RNA pellet was washed with ice cold 2M LiCl, air dried, and resuspended in autoclaved water. The 8M LiCl solution and water used to resuspend the RNA was previously treated with 0.05% (v:v) diethyl pyrocarbonate (Sigma Chemical Co., St. Louis, Mo.). About 100 g of total RNA was further purified by passage through an RNeasy column (Qiagen Inc., Valencia, Calif.), as recommended by the manufacturer. Purified RNA was stored at −80° C.

For northern blots, approximately 4–5 μg of purified RNA was brought to 10 μL with sample buffer containing 50% formamide, 6% formaldehyde (Fisher #BP531), 20 mM MOPS, pH 7.0, 5 mM sodium acetate, 10 mM EDTA, and 0.01% bromophenol blue. RNA samples were heated at 60° C. for 10 to 15 minutes, then immediately placed on ice prior to partitioning on agarose. The agarose (0.3 g) was dissolved in 30 mL of 20 mM MOPS, 5 mM sodium acetate, 10 mM EDTA, pH 7.0, to which was added 37% formaldehyde for a final concentration of 6% and 10 μg/μL ethidium bromide for a final concentration of 166 ng/mL. Electrophoresis was carried out at 50–70 V for up to 2 hours. Partitioned RNA was transferred to Zeta-Probe GT nylon membrane (Bio-Rad, Hercules, Calif.) in either 10×SSC (150 mM sodium chloride, 15 mM sodium citrate, pH 7.0) or 50 mM sodium hydroxide for 3 hours. The nylon membrane containing RNA (northern blot) was rinsed in 2×SSC (30 mM sodium chloride, 3 mM sodium citrate, pH 7.0) and either treated with ultraviolet light using a UV Stratalinker 2400 (Stratagene, La Jolla, Calif.) and baked at 80° C. under vacuum (neutral transfer), or air dried and used directly (alkaline transfer).

Figure 13:

Northern blots were incubated in a Hybaid hybridization oven (National Labnet, Woodbridge, N.J.) for 6 to 7 hours at 42° C. in 5 to 10 mL of a solution containing 50% (v:v) formamide, 7% (w:v) sodium dodecyl sulfate (SDS), 0.25 M sodium phosphate buffer, pH 7.0, 0.25 M sodium chloride, and 1 mM EDTA, pH 8.0, as recommended by Bio-Rad. Probes for northern blots consisted of partial or full-length cDNAs as follows: 0.4 kb BamHI GLU fragment from FvGluS; 1.2 kb BamHI+BglII Endo fragment from FvEndoS; or 1.8 kb BamHI+BglII Exo fragment from FvExoS. Probe fragments were purified following agarose gel partitioning as described in Example 12. About 25–50 ng of probe DNA was radiolabeled to a specific activity of 1–2× $10^6$ cpm/ng with $^{32}$P-α-dCTP (3000 Ci/mmol), using the Multiprime DNA Labelling System (Amersham Pharmacia Biotech, Inc., Piscataway, N.J.) as recommended. Radiolabeled fragments were added directly to the northern blots and hybridized at 42° C. for up to 36–40 hours. Blots were washed in 200 to 300 mL of 2×SSC, 0.1% (w:v) SDS at room temperature for 15 minutes; in 200 to 300 mL of 0.5×SSC, 0.1% (w:v) SDS at room temperature for 15 minutes; and in 200 to 300 mL of 0.1×SSC, 0.1% (w:v) SDS at 62° C. for 15 minutes. Autoradiography was performed at −80° C. on preflashed XAR 5 film (Kodak, Rochester, N.Y.), using an X-ray film cassette and Spectroline L-Plus intensifying screen (Spectronics Corp., Westbury, N.Y.), or at room temperature on a phosphor screen using a Storm 820 phosphoimager (Molecular Dynamics, Sunnyvale, Calif.). Northern blot analysis detected the presence of mRNA transcripts from the endochitinase transgene in line AB8-108 (FIG. 13).

Heterozygous and homozygous lines and/or their progeny, identified as described in Example 20, were also analyzed for the accumulation of transgene mRNAs using reverse transcription-polymerase chain reaction (RT-PCR). RT-PCR is a more sensitive means by which to detect mRNA accumulation in various tissues and organs (Altenbach 1998; Wang et. al. 1998). Total RNA was obtained from glumes of wheat at 2 to 3 weeks post anthesis using the same procedure described for endosperm RNA isolation (above). RT-PCR was carried out on 600 ng of total RNA using either the GeneAmp PCR Core kit (Perkin Elmer, Foster City, Calif.) or a OneStep RT-PCR Kit (Qiagen, Inc., Valencia, Calif.), as recommended by the manufacturers. Transgene-specific transcripts were amplified using primers RTUBI and either RTGLU (for the 5' end of the endochitinase transcript), RTEND (for the 5' end of the endochitinase transcript), or RTEXO (for the 5' end of the exochitinase transcript). See Table 3 for a list of RT-PCR primers. The 3' portions of the transgene transcripts were amplified with RTNOS and either RTGLU2 (glucanase), RTEND2 (endochitinase), or RTEXO2 (exochitinase). The annealing temperatures were 58°–60° C.

Figure 14:
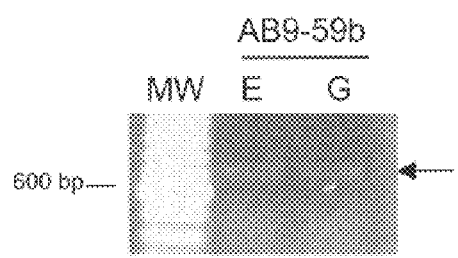

Endosperm and glume total RNA from Line AB9–59b showed very low but detectable levels of a single 700 bp RT-PCR product (FIG. 14), representing the 5' end of the transcript, and including the Ubi exon. The size of this product compared closely with the expected product size of 705 bp, which was derived from the predicted nucleotide sequence of the transgene mRNA. The 3' portion of the glucanase transcript was also amplified at very low, but detectable levels (data not shown), yielding a single 330 bp PCR product (expected size 340 bp).

In endosperm and glume total RNA isolated from two successive generations of Line AB8-108, a single ~700 bp RT-PCR product, representing the 5' end of the endochitinase mRNA, (expected size 685 bp) (FIG. 15A, left and right panels), and a single 320 bp RT-PCR product, representing the 3' end of the endochitinase mRNA, (expected size 310 bp) (FIG. 15B) were strongly amplified. In total RNA from endosperm of Line C9-25a, a single ~800 bp RT-PCR product, representing the 5' end of the exochitinase mRNA (expected size 795 bp) (FIG. 1 5A, right panel), and a single 300 bp RT-PCR product representing the 3' end of the exochitinase mRNA (expected size 310 bp)(FIG. 15B) was detectable. Total RNA from untransformed cultivar Bobwhite (bw) did not produce any RT-PCR products.

Figure 16:
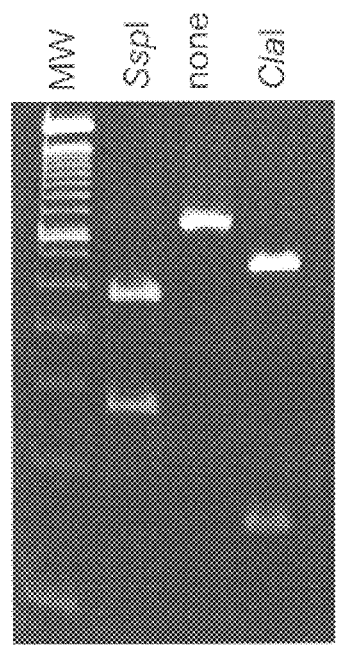

For the purpose of authentication, the endochitinase 5' RT-PCR product was cleaved exhaustively with either ClaI or SspI restriction endonuclease according to the manufacturer's specifications (New England BioLabs, Beverly, Mass.). The resulting cleavage products were partitioned on a 6% TBE acrylamide gel (Novex/Invitrogen, Carlsbad, Calif.), 100V for ~1 hr, in running buffer consisting of 89 mM TRIS-Cl, pH 8.3, 89 mM borate, 1.5 mM EDTA. The resulting endochitinase cleavage products, shown in FIG. 16, closely matched those expected from the predicted nucleotide sequence of the endochitinase mRNA, and confirmed the identity of the RT-PCR product. Likewise, the exochitinase 5' RT-PCR product was cleaved with either BglII, EcoRV, or NcoI restriction enzymes (New England BioLabs, Beverly, Mass.). The resulting cleavage products, partitioned on either a 6% acrylamide gel (FIG. 17A) or a 2% agarose gel (FIG. 17B), as previously described in Example 8, were very close in size to those expected from the predicted nucleotide sequence of the exochitinase mRNA. Due to the presence of a minor amplification product in the starting material (lane labeled "none", FIG. 17A), additional cleavage fragments were observed in the first experiment. The major fragment at ~800 bp in the BglII lane of the second experiment (FIG. 17B) is attributed to incomplete cleavage by BglII.

Figure 18:
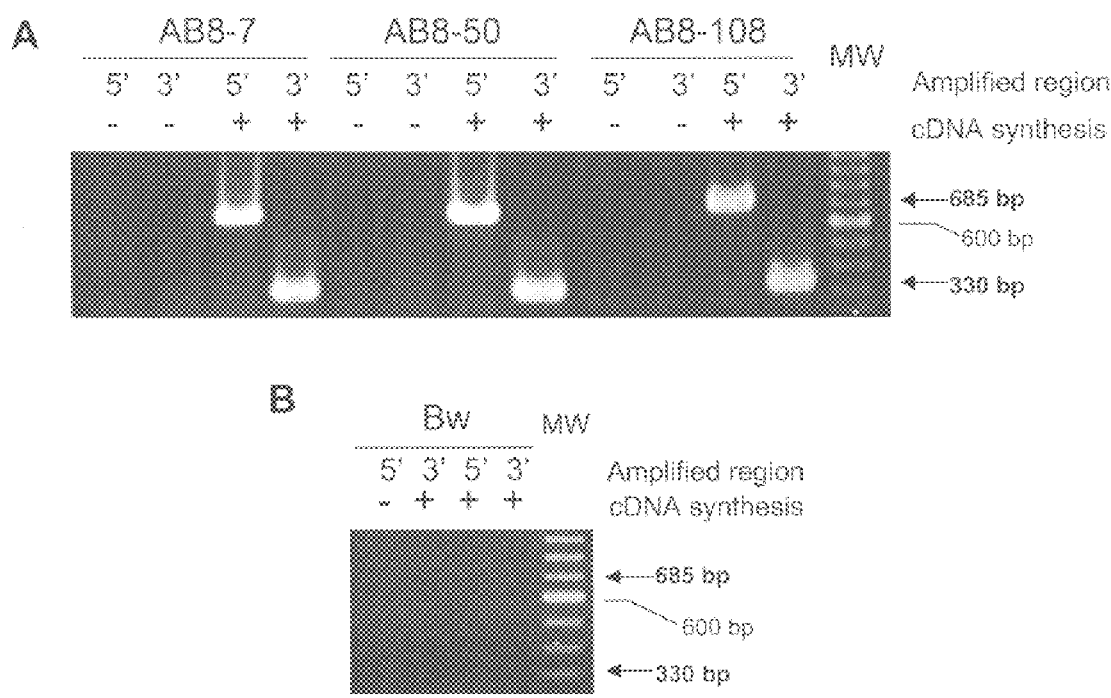
FIG. 18 shows FvEndo 5' and 3' RT-PCR products are cDNA-dependent.
Figure 19:
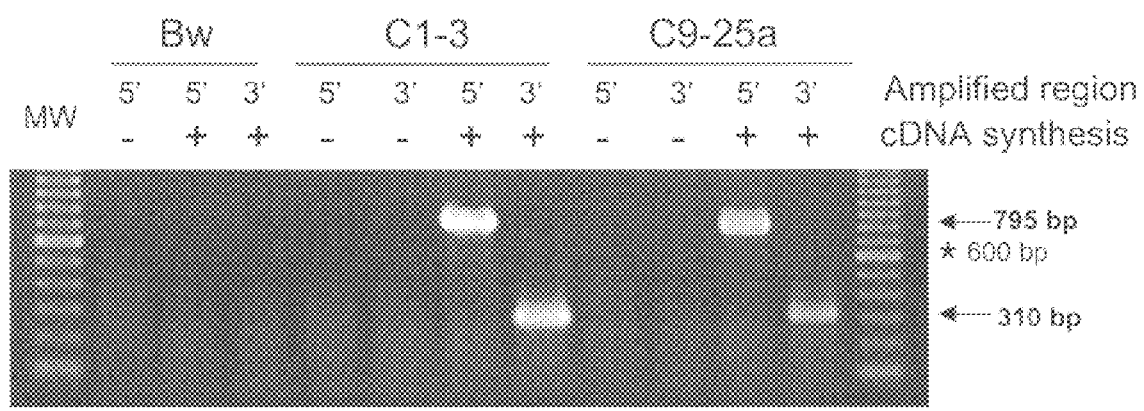
FIG. 19 shows FvExo 5' and 3' RT-PCR products are cDNA-dependent.

The FvEndo and FvExo RT-PCR products were cDNA-dependent, and were therefore generated from RNA rather than from contaminating genomic DNA in the RNA preparations. The RT-PCR products were amplified from both the 5' and 3' regions of the FvEndo transcripts in endosperm from three independent lines (FIG. 18A) only if cDNA synthesis (+) was first carried out. In the absence of cDNA synthesis(−), no 5' or 3' RT-PCR products were obtained. As expected, FvEndo transcripts were not detected in endosperm of untransformed Bobwhite (Bw) either with or without cDNA synthesis (FIG. 18B). Likewise, FvExo RT-PCR products were amplified from both 5' and 3' regions of the transcripts only after cDNA synthesis (FIG. 19). No products were obtained in untransformed Bobwhite samples.

TABLE 3

PCR primers used for RT-PCR experiments

| Primer | Sequence (5' to 3') | Amplification target | SEQ ID NO: |
|---|---|---|---|
| RTEND | CTGGAAGTTTGTCGCACCG | 5' end of FvEndo transcript | 75 |
| RTEND2 | GAGATAGAGGATGCTGTGCC | 3' end of FvEndo transcript | 76 |
| RTEXO | CAGTGATGTGAAGGTGAAGGC | 5' end of FvExo transcript | 77 |
| RTEXO2 | CGTATGGACTGAGACTATCGAC | 3' end of FvExo transcript | 78 |
| RTGLU | GAGCATCCTTGATQGGAACAC | 5' end of FVGIU transcript | 79 |
| RTGLU2 | GTCAACTCCAAGGCTGTCGTC | 3' end of PvGlu transcript | 80 |
| RTNOS | GCCAAATGTTTGAACUATCTUC | 3' end of transcripts | 81 |
| RTUBI | CAACCTCGTGTTGTTCGGAG | 5' end of transcripts | 82 |

Example 22

Determination of Copy Number of the Glucanase and Chitinase Genes in the *F. venenatum* Genome

*F. venenatum* CC1-3, a morphological mutant of strain A3/5 (Wiebe et al. 1991) was used for the DNA blots described in this example. Genomic DNA (5 μg per treatment) was cleaved exhaustively with HindIII, BamHI, or EcoRI restriction endonuclease, partitioned on agarose gels as described in EXAMPLE 8, then transferred to Nytran SuPerCharge (Schleicher and Schuell, Keene, N.H.). Procedures for transfer of DNA to the membrane, for hybridization with radiolabeled and non-radiolabeled probes, and for washing are described on the Schleichler and Schuell website at http://www.s-und-s.de/Pages-NEU-en. . . 0science/Lab %20Manual/southern.htm. The hybridization probes consisted of the following: 1) the 0.4 kb 5' BamHI fragment of FvGlu cDNA (from plasmid described in EXAMPLE 15); 2) 1.2 kb BamHI-BglII FvEndo cDNA fragment from FvEndoS (FIG. 15); (3) the 1.8 kb BamHI/BglII FvExo cDNA fragment (from plasmid described in EXAMPLE 15). The probes were made radioactive with $^{32}$P-alpha-dCTP [specific activity 3000 Ci (111tBq)/mmol] using the Multiprime DNA labelling system (Amersham Pharmacia Biotech, Inc., Piscataway, N.J.).

Figure 20:
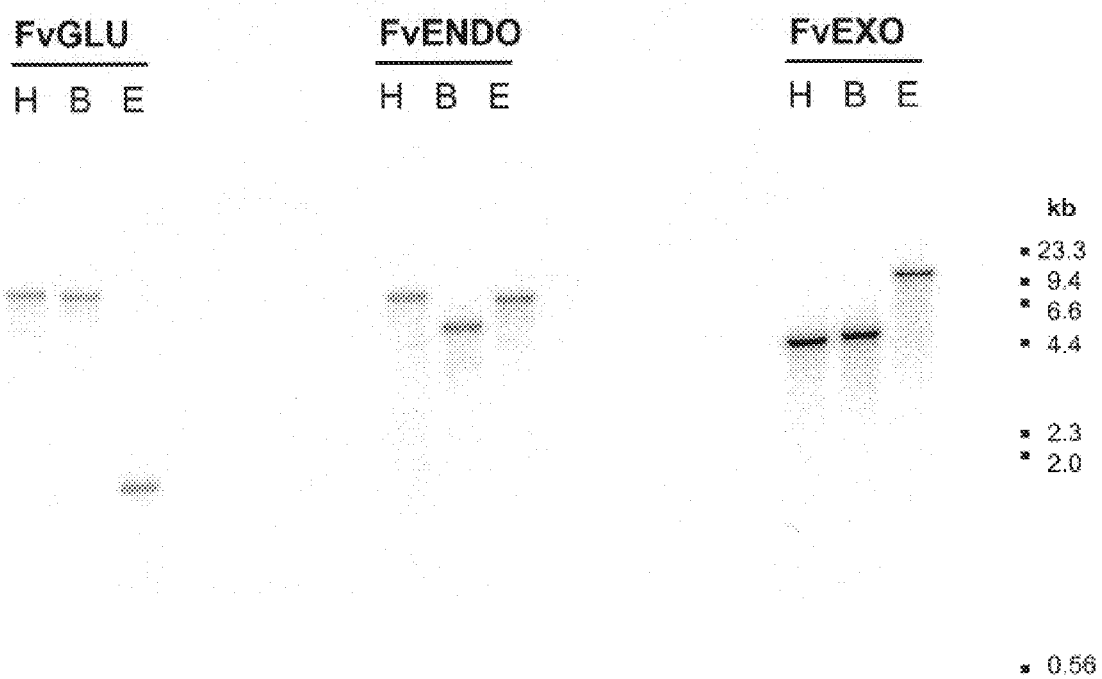
FIG. 20 shows Southern blots of *F. venenatum* genomic DNA hybridized with FvGlu, FvEndo, FvExo cDNAs.

Our Southern blot results indicate that each of the three genes are present in a single copy in the *F. venenatum* genome (FIG. 20). The sizes of the hybridizing bands for FvGlu were estimated to be 12.5 kb (HindIII), 1.6 kb (BamHI), and 11 kb (EcoRI), using phage Lambda DNA cleaved with HindIII as a migration standard (see "kb" in FIG. 20). The FvGlu coding region contains a single BamHI site, so two hybridizing BamHI fragments would have been obtained with a full-length cDNA probe. However, the FvGlu probe that was used for this experiment consisted of cDNA sequences 5' to the BamHI site, so a single hybridizing BamHI fragment was expected and was obtained. The sizes of the hybridizing FvEndo fragments were 9.3 kb (HindIII), 8.9 kb (BamHI), and 6.6 kb (EcoRI). The sizes of the hybridizing FvExo fragments were 4.3 kb (HindIII), 11 kb (BamHI), and 4.7 kb (EcoRI). Neither FvEndo nor FvExo coding regions carry restriction sites for these three endonucleases.

Statement of Deposit

Plasmids identified below were introduced into the host *Escherichia coli* and the transformed *Escherichia coli* were deposited under terms of the Budapest Treaty with Agricultural Research Service Culture Collection (NRRL) National Center for Agricultural Utilization Research, Agricultural Research Service, U.S. Department of Agriculture, 1815 North University Street, Peoria, Ill. 61604 USA on the date listed and given the following accession numbers:

| Deposit | Accession No. | FIG./Seq No | Date of Deposit |
|---|---|---|---|
| GLU2 | NRRL B-30201 | SEQ16 | 8/26/99 |
| Endo167 | NRRL B-30202 | SEQ18 | 8/26/99 |
| Exo9 | NRRL B-30203 | SEQ20 | 8/26/99 |
| FvGluS | NRRL B-30204 | FIG. 6 | 8/26/99 |
| FvGluAS | NRRL B-30205 | FIG. 7 | 8/26/99 |
| FvEndoS | NRRL B-30206 | FIG. 8 | 8/26/99 |
| FvEndoAS | NRRL B-30207 | FIG. 9 | 8/26/99 |
| FvExoS | NRRL B-30208 | FIG. 10 | 8/26/99 |
| FvExoAS | NRRL B-30209 | FIG. 11 | 8/26/99 |

It is understood that the foregoing detailed description is given merely by way of illustration and that modification and variations may be made within, without departing from the spirit and scope of the invention. All publications, patents, and patent applications cited herein are hereby incorporated by reference in their entirety.

REFERENCES

Andersen, A. (1948). The development of Gibberella zeae headblight of wheat. Phytopathology, 38: 595–611

Altenbach, S. B. (1998). Quantification of individual low-molecular-weight glutenin subunit transcripts in developing wheat grains by competitive RT-PCR. Theor Appl Genet 97: 413–421

Altschul S. F., Madden T. L., Schaffer A A, Zhang J, Zhang Z, Miller W, Lipman D J (1997). Gapped BLAST and PSI-BLAST: a new generation of protein database search programs. Nucleic Acids Res. 25: 3389–3402

Bai and Shaner (1994). Scab of wheat: prospects for control. Plant Disease 78: 760–766

Barbosa, I. P. and C. Kemmelmeier (1993). Chemical composition of the hyphal wall from *Fusarium graminearum*. Exp. Mycol. 17: 274–283

Battraw, M. J. and T. C. Hall (1990). Histochemical analysis of CaMV 35S promoter-β-glucuronidase gene expression in transgenic rice plants. Plant Mol. Biol. 15: 527–538

Becker, D., R. Brettschneider, and H. Lorz (1994). Fertile transgenic wheat from microprojectile bombardment of scutellar tissue. Plant J. 5: 299–307

Beffa, R. and F. Meins, Jr. (1996). Pathogenesis-related functions of plant β-1,3-glucanases investigated by antisense transformation—a review. Gene 179: 97–103

Blaiseau, P-L. and J-F. Lafay (1992). Primary structure of a chitinase-encoding gene (chi1) from the filamentous fungus *Aphanocladium album*: similarity to bacterial chitinases. Gene 120: 243–248.

Blechl, A. E. and O. D. Anderson (1996). Expression of a novel high-molecular-weight glutenin subunit gene in transgenic wheat. Nat. Biotech. 14: 875–879

Bliffeld, M., J. Mundy, I. Potrykus and J. Futterer (1998). Genetic engineering of wheat for increased resistance to powdery mildew disease. Theor. Appl. Genet. 98: 1079–1086

Bolar J. P., J. L. Norelli, K-W Wong, C. K. Hayes, G. E. Harman, and H. S. Aldwinckle (2000). Expression of endochitinase from Trichoderma harzianum in transgenic apple increases resistance to apple scab and reduces vigor. Phytopathology 90: 72–77

Boyapati, R., A. L. Moyne, T. E. Cleveland and S. Tuzun (1994). Cloning of putative chitinase genes from Bacillus to control toxin producing fungi. Phytopathology 84: 1081

Broekaert, W. F., J. Van Parijs, A. K. Allen and W. J. Peumans (1988). Comparison of some molecular, enzymatic and antifungal properties of chitinases from thornapple, tobacco and wheat. Physiol. Mol. Plant Path. 33: 319–331

Brunner, F., A. Stintzi, B. Fritig, and M. Legrand (1998). Substrate specificities of tobacco chitinases. Plant J. 14: 225–234

Caruso, C., C. Caporale, G. Chilosi, F. Vacca, L. Bertini, P. Magro, E. Poerio and V. Buonocore (1996). Structural and antifungal properties of a pathogenesis-related protein from wheat kernel. J. Prot. Chem. 15: 35–44.

Cavallarin, L., D. Andreu and B. San Segundo (1998). Cecropin A-derived peptides are potent inhibitors of fungal plant pathogens. Mol. Plant-Microbe Inter. 11: 218–227.

Chen, W. P., X. Gu, G. H. Liang, S. Muthukrishnan, P. D. Chen, D. J. Liu and B. S. Gill (1998). Introduction and constitutive expression of a rice chitinase gene in bread wheat using biolistic bombardment and the bar gene as a selectable marker. Theor. Appl. Genet. 97: 1296–1306

Cherif, M. and N. Benhamou (1990). Cytochemical aspects of chitin breakdown during the parasitic action of a Trichoderma sp. on *Fusarium oxysporum* f. sp. radicis-lycospersici. Phytopathology 80: 1406–1414

Christensen, A. H. and P. H. Quail (1996). Ubiquitin promoter-based vectors for high-level expression of selectable and/or screenable marker genes in monocotyledonous plants. Trans. Res. 5: 213–218

Collinge, D. B., K. M. Kragh, J. D. Mikkelsen, K. K. Nielsen, U. Rasmussen, K. Vad. (1993). Plant chitinases. The Plant Journal 3:31–40

Cornejo, M-J., D. Luth, K. M. Blankenship, O. D. Anderson and A. E. Blechl (1993). Activity of a maize ubiquitin promoter in transgenic rice. Plant Mol. Biol. 23: 567–581

Cruz-Ortega, R., J. C. Cushman and J. D. Ownby (1997). cDNA clones encoding 1,3-β-glucanase and a fimbrin-like cytoskeletal protein are induced by Al toxicity in wheat roots. Plant Physiol. 114: 1453–1460 de Block, M., J. Botterman, M. Vandewiele, J. Dockx, C. Thoen, V. Gosselé, N. Rao Movva, C. Thompson, M. Van Montagu and J. Leemans (1987). Engineering herbicide resistance in plants by expression of a detoxifying enzyme. EMBO J. 6: 2513–2518

Dellaporta, S. L., J. Wood and J. B. Hicks (1983). A plant DNA minipreparation: version II. Plant Mol. Biol. Rep. 1: 19–21 deLucca, A. J., J. M. Bland, T. J. Jacks, C. Grimm, T. E. Cleveland, and T. J. Walsh (1997). Fungicidal activity of cecropin A. Antimicrob. Agents Chemother. 41: 481–483

D'Ovidio, R., O. A. Tanzarella and E. Porceddu (1992). Isolation of an alpha-type gliadin gene from *Triticum durum* Desf. and genetic polymorphism at the Gli-2 loci. J. Genet. Breed. 46: 41–48.

Draborg, H., S. Kauppinen, H. Dalbøge and S. Christgau (1995). Molecular cloning and expression in *S. cerevisiae* of two exochitinases from *Trichoderma harzianum*. Biochem. Mol. Biol. Int. 36: 81–791

Flach, J., P.-E. Pilet, and P. Jollés (1992). What's new in chitinase research? Experientia 48: 701–716

Fontaine, T., R. P. Hartland, M. Diaquin, C. Simenel, and J. P. Latge (1997). Differential patterns of activity displayed by two exo-β-1,3-glucanases associated with the *Aspergillus fumigatus* cell wall. J Bact 179: 3154–3163

Freeling, M. and D. C. Bennett (1985). Maize Adh1. Annu Rev Genet 19:297–323

Fritig, B., T. Heitz and M. Legrand (1998). Antimicrobial proteins in induced plant defense. Curr. Opinion Immun. 10: 16–22

Fukamizo, T., T. Ohkawa, K. Sonoda, H. Toyoda, T. Nishiguchi, S. Ouchi and S. Goto (1992). Chitinous components of the cell wall of *Fusarium oxysporum*. Biosci. Biotech. Biochem. 56: 1632–1636

Fuitterer, J. and T. Hohn (1996). Translation in plants—rules and exceptions. Plant Mol. Biol. 32: 59–189

Graham, L. S. and M. B. Sticklen (1994). Plant chitinases. Can. J. Bot. 72: 1057–1083

Harman, G. E., C. K. Hayes, M. Lorito, R. M. Broadway, A. Di Pietro, C. Peterbauer, and Tronsmo A (1993). Chitinolytic enzymes of *Trichoderma harzianum*: purification of chitobiosidase and endochitinase. Phytopathology 83: 313–318

Hu, X. and A. S. N. Reddy (1997). Cloning and expression of a PR5-like protein from Arabidopsis: inhibition of fungal growth by bacterially expressed protein. Plant Mol. Biol. 34: 949–959

Huynh, T. V., R. A. Young, and R. W. Davis. Constructing and screening cDNA libraries in Lambda-gt10 and Lambda-gt11. In: *DNA Cloning Techniques. A Practical Approach*, edited by D. Glover, IRL Press: Oxford, 1984, p. 1–62.

Jach, G., B. Görnhardt, J. Mundy, J. Logemann, E. Pinsdorf, R. Leah, J. Schell and C. Maas (1995). Enhanced quantitative resistance against fungal disease by combinatorial expression of different barley antifungal proteins in transgenic tobacco. Plant J. 8: 97–109

Jensen, L. G., O. Politz, O. Olsen, K. K. Thomsen and D. Von Wettstein (1998). Inheritance of a codon-optimized transgene expressing heat stable (1,3–1,4)—glucanase in scutellum and aleurone of germinating barley. Hereditas 129: 215–225

Jondedijk, E., H. Tigelaar, J. S. C. van Roekel, S. A. Bres-Vloemans, I. Dekker, P. J. M. van den Elzen, B. J. C. Cornelissen, and L. S. Melchers (1995). Synergistic activity of chitinases and β-1,3-glucanases enhances fungal resistance in transgenic tomato plants. Euphytica 85: 173–180

Jutidamrongphan, W., J. B. Anderson, C. Mackinnon, J. M. Manners, R. S. Simpson and K. J. Scott (1991). Induction of β-1,3-glucanase in barley in response to infection by fungal pathogens. Mol. Plant-Microbe Inter. 4: 234–238

Keen N. T. and M. Yoshikawa M (1983). β1,3-endoglucanase from soybean releases elicitor-active carbohydrates from fungus cell walls. Plant Physiol 71: 460–465

Klebl, F. and W. Tanner (1989). Molecular cloning of a cell wall exo-β-1,3-glucanase from *Saccharomyces cerevisiae*. J. Bact. 171: 6259–6264

Kozak, M. (1987). An analysis of 5'-noncoding sequences from 699 vertebrate messenger RNAs. Nucl. Acids Res. 15: 8125–8148

Krishnaveni, S., S. Muthukrishnan, G. H. Liang, G. Wilde and A. Manickam (1999a). Induction of chitinases and β-1,3-glucanases in resistant and susceptible cultivars of sorghum in response to insect attack, fungal infection and wounding. Plant Sci 144: 9–16

Krishnaveni, S., G. H. Liang, S. Muthukrishnan and A. Manickam (1999b). Purification and partial characterization of chitinases from sorghum seeds. Plant Sci. 144: 1–7

Linthorst, H. J. M. (1991). Pathogenesis-related proteins of plants. Crit. Rev. Plant Sci. 10: 123–150

Linthorst, H. J. M., L. S. Melchers, A. Mayer, J. S. C. van Roekel, B. J. C. Cornelissen and J. F. Bol (1990). Analysis of gene families encoding acidic and basic β-1,3-glucanases of tobacco. Proc. Natl. Acad. Sci. 87: 8756–8760

Liu, L., D. S. Maillet, J. R. H. Frappier, D. B. Walden and B. G. Atkinson (1995). Characterization, chromosomal mapping, and expression of different polyubiquitin genes in tissues from control and heat-shocked maize seedlings. Biochem. Cell Biol. 73: 19–30

Lotan, T., N. Ori and R. Fluhr (1989). Pathogenesis-related proteins are developmentally regulated in tobacco flowers. Plant Cell 1: 881–887

Lorito, M., S. L. Woo, I. G. Fernandez, G. Colucci, G. E. Harman, J. A. Pintor-Toro, E. Filippone, S. Muccifora, C. B. Lawrence, A. Zoina, S. Tuzun and F. Scala (1998). Genes from the mycoparasitic fungi as a source for improving plant resistance to fungal pathogens. Proc. Natl. Acad. Sci. 95: 7860–7865

Luehrsen, K. R. and V. Walbot (1994). The impact of AUG start codon context on maize gene expression in vivo. Plant Cell Rep. 13: 454–458

Malehorn, D. E., K. J. Scott and D. M. Shah (1993). Structure and expression of a barley acidic β-glucanase gene. Plant Mol. Biol. 22: 347–360

Mauch F., B. Mauch-Mani and T. Boller (1988). Antifungal hydrolases in pea tissue. II. Inhibition of fungal growth by combinations of chitinase and β-1,3-glucanase. Plant Physiol. 88: 936–942

McCreath, K. J. and G. W. Gooday (1992). A rapid and sensitive microassay for determination of chitinolytic activity. J Microbiol Meth 14: 229–237

McCue, K. F. and A. D. Hanson (1990). Drought and salt tolerance: towards understanding and application. Trends Biotech. 8: 358–362

McKay, R. and J. B. Loughnane (1945), Observations on Gibberella saubinetti (Mont.) Sacc. on cereals in Ireland in 1943 and 1944. Sci. Proc.R. Dublin Soc. 24: 9–18

Melchers, L. S., M. Apotheker-de Groot, J. A. van der Knaap, A. S. Ponstein, M. B. Sela-Buurlage, J. F. Bol, B. J. C. Cornelissen, P. J. M. van den Elzen, and H. J. M. Linthorst (1994). A new class of tobacco chitinases homologous to bacterial exo-chitinases displays antifungal activity. Plant J. 5: 469–480

Michael, A. H. and Nelson, P. E. (1972). Antagonistic effect of soil bacteria on *Fusarium roseum culmorum*. Phytopathology 62: 1052–1056

Mitchell, R. and Alexander, M. (1961). The mucolytic phenomenon and biological control of Fusarium in soil. Nature 190: 109–110

Molina, A., A. Segura and F. Garcia-Olmedo (1993). Lipid transfer proteins (nsLTPs) from barley and maize leaves are potent inhibitors of bacterial and fungal plant pathogens. FEBS Lett. 316: 119–122

Nehra, N. S., R. N. Chibbar, N. Leung, K. Caswell, C. Mallard, L. Steinhauer, M. Baga and K. K. Kartha (1994). Self-fertile transgenic wheat plants regenerated from isolated scutellar tissues following microprojectile bombardment with two distinct gene constructs. Plant J. 5: 285–297

Parry, D. W., P. Jenkinson and L. McLeod (1995). Fusarium ear blight (scab) in small grain cereals—a review. Plant Pathology 44: 207–238

Payne, G., E. Ward, T. Gaffney, P. A. Goy, M. Moyer, A. Harper. F. Meins, Jr. and J. Ryals (1990). Evidence for a third class of β-1,3-glucanase in tobacco. Plant Mol. Biol. 15: 797–808

Pearce, R. B., R. N. Strange and H. Smith (1976). Glycinebetaine and choline in wheat: distribution and relation to infection by Fusarium graminearum. Phytochemistry 15: 953–954

Pearson, W. R. (1990). Rapid and sensitive sequence comparison with FASTP and FASTA. Methods Enzymology 183:63–98.

Peterbauer, C. K., M. Lorito, C. K. Hayes, G. E. Harman and C. P. Kubicek (1996). Molecular cloning and expression of the nag1 gene (N-acetyl-β-D-glucosaminidase-encoding gene) from Trichoderma harzianum P1. Curr. Genet. 30: 325–331

Pugh, G. W., H. Johann and J. G. Dickson (1933). Factors affecting infection of wheat heads by Gibberella saubinetii. J. Agr. Res. 46: 771–797

Sambrook, J., E. F. Fritsch and T. Maniatis (1989). *Molecular Cloning, A Laboratory Manual*, vol. 1–3 (Cold Spring Harbor Laboratory Press, Cold Spring Harbor, N.Y.).

Sanger, F., S. Nicklen and A. R. Coulsen (1977). DNA sequencing with chain-terminating inhibitors. Proc. Natl. Acad, Sci. 74: 5463–5467

Seetharaman, K., E. Whitehead, N. P. Keller, R. D. Waniska, and L. W. Rooney ((1997). In vitro activity of sorgum seed antifungal proteins against grain mold pathogens. J. Agric. Food Chem. 45: 3666–3671

Sela-Buurlage, M. B., A. S. Ponstein, S. A. Bres-Vloemans, L. S. Melchers, P. J. M. van der Elzen and B. J. C. Cornelissen (1993). Only specific tobacco (Nicotiana tabacum) chitinases and β-1,3-glucanases exhibit antifungal activity. Plant Physiol. 101: 857–863

Simmons, C. R. (1994). The physiology and molecular biology of plant 1,3-β-D-glucanases and 1,3;1,4-β-D-glucanases. Crit. Rev. Plant Sci. 13: 325–387

Sivan, A. and I. Chet (1989a). Cell wall composition of Fusarium oxysporum. Soil Biol. Biochem. 21: 869–871

Sivan A and I. Chet (1989b). Degradation of fungal cell walls by lytic enzymes of Trichoderma harzianum. J. Gen. Microbiol. 135: 675–682

Spratt, B. G., P. J. Hedge, S. te Heesen, A. Edelman and J. K. Broome-Smith (1986). Kanamycin-resistant vectors that are analogues of plasmids pUC8, pUC9, pEMBL8 and pEMBL9. Gene 41: 337–342

Srivastava, A. K., G. Defago, T. Boller (1985). Secretion of chitinase by Aphanocladium album, a hyperparasite of wheat rust. Experientia 41: 1612–1613

Strange, R. N., J. R. Majer and H. Smith (1974). The isolation and identification of choline and betaine as the two major components in anthers and wheat germ that stimulate Fusarium graminearum in vitro. Physiol. Plant Path. 4: 277–290

Strange, R. N. and H. Smith (1971). A fungal growth stimulant in anthers which predisposes wheat to attack by Fusarium graminearum. Physiol. Plant Path. 1: 141–150

Strange, R. N. and H. Smith (1978). Effects of choline, betaine and wheat-germ extract on growth of cereal pathogens. Trans. Br. mycol. Soc. 70: 193–199

Suslow, T., D. Matsubara, J. Jones, R. Lee and P. Dunsmuir (1988). Effect of expression of bacterial chitinase on tobacco susceptibility to leaf brown spot. Phytopathology 78: 1556

Tailor, R. H., D. P. Acland, S. Attenborough, B. P. A. Cammue, I. J. Evans, R. W. Osbom, J. A. Ray, S. B. Rees, and W. F. Broekaert (1997). A novel family of small cysteine-rich antimicrobial peptides from seed of Impatiens balsamina is derived from a single precursor protein. J. Biol. Chem. 272: 24480–24487.

Terakawa, T., N. Tanaya, H. Horiuchi, M. Koike and M. Takagi (1997). A fungal chitinase gene from Rhizopus oligosporus confers antifungal activity to transgenic tobacco. Plant Cell Rep. 16: 439–443

Terras, F. R. G., H. M. E. Schoofs, K. Thevissen, R. W. Osbom, J. Vanderleyden, B. P. A. Cammue and W. F. Broekaert (1993). Synergistic enhancement of the antifungal activity of wheat and barley thionins by radish and oilseed rape 2S albumins and by barley trypsin inhibitor. Plant Physiol. 103: 1311–1319

Thompson, J. D., D. G. Higgins, and T. J. Gibson (1994). CLUSTAL W: improving the sensitivity of progressive multiple sequence alignment through sequence weighting, positions-specific gap penalties and weight matrix choice. Nucl Acids Res 22: 4673–4680.

Tzafrir, I., K. A. Torbert, B. E. L. Lockhart, D. A. Somers and N. E. Olszewski (1998). The sugarcane bacilliform badnavirus promoter is active in both monocots and dicots. Plant Mol Biol 38: 347–356

Tronsmo A. and G. E. Harman (1993). Detection and quantification of N-acetyl-β-D-glucosaminidase, chitobiosidase, and endochitinase in solutions and on gels. Anal Biochem 208: 74–79

Van Loon, L. C. (1997) Induced resistance in plants and the role of pathogenesis-related proteins Eur. J. Plant Path. 103: 753–765

Vasil, V., A. M. Castillo, M. E. Fromm, and I. K. Vasil (1992). Herbicide resistant fertile transgenic wheat plants obtained by microprojectile bombardment of regenerable embryogenic callus. Bio/Technology 10: 667–674

Vasil, V., V. Srivastava, A. M. Castillo, M. E. Fromm, and I. K. Vasil (1993). Rapid production of transgenic wheat plants by direct bombardment of cultured immature embryos. Bio/Technology 11: 1553–1558

Vázquez-Garciduenãs, S., C. A. Leal-Morales and A. Herrera-Estrella (1998). Analysis of the β-1,3-glucanolytic system of the biocontrol agent Trichoderma harzianum. Appl. Environ. Microbiol. 64: 1442–1446

Wang, A M, M. V. Doyle, D. F. Mark (1989). Quantitation of mRNA by the polymerase chain reaction. Proc Natl Acad Sci 86: 9717–9721

Weeks, J. T., O. D. Anderson and A. E. Blechl (1993). Rapid production of multiple independent lines of fertile transgenic wheat. Plant Physiol. 102: 1077–1084

Wiebe, M. G., A. P. J. Trinci, B. Cunliffe, G. D. Robson, S. G. Oliver (1991). Appearance of morphological (colonial) mutants in glucose-limited continuous flow cultures of Fusarium graminearum. Mycol Res 95: 1284–1288

Wu, S., A. L. Kriz, and J. M. Widholm (1992). Molecular analysis of two cDNA clones encoding acidic class I chitinase in maize. Plant Physiol. 105: 1097–1105

Xu, P., J. Wang and G. B. Fincher (1992). Evolution and differential expression of the (1–3)-β-glucan endohydrolase-encoding gene family in barley, *Hordeum vulgare*. Gene 120: 157–165

Yang, C., Y. Zhu, D. M. Magee and R. A. Cox (1996). Molecular cloning and characterization of the *Coccidioides immitis* complement fixation/chitinase antigen. Infect. Immun. 64: 1992–1997

Yun, D-J., M. Paino D'Urzo, L. Abad, S. Takeda, R. Salzman, Z. Chen, H. Lee, P. M. Hasegawa and R. A. Bressan (1996). Novel osmotically induced antiflugal chitinases and bacterial expression of an active recombinant isoform. Plant Physiol. 111: 1219–1225

Zhang, W., D. McElroy and R. Wu (1991). Analysis of rice Act1 5' region activity in transgenic rice plants. Plant Cell 3: 1155–1165

Zimmermann, C. R., S. M. Johnson, G. W. Martens, A. G. White and D. Pappagianis (1996). Cloning and expression of the complement fixation antigen-chitinase of *Coccidioides immitis*. Infect. Immun. 64: 4967–4975

Zhu, Q., E. A. Maher, S. Masoud, R. A. Dixon and C. J. Lamb (1994). Enhanced protection against fungal attack by constitutive co-expression of chitinase and glucanase genes in transgenic tobacco. Bio/Tech. 12: 807–812

---

SEQUENCE LISTING

```
<160> NUMBER OF SEQ ID NOS: 82

<210> SEQ ID NO 1
<211> LENGTH: 1023
<212> TYPE: DNA
<213> ORGANISM: Fusarium venenatum
<220> FEATURE:
<221> NAME/KEY: CDS
<222> LOCATION: (37)..(942)

<400> SEQUENCE: 1
cagttatctt tttttatcta ctatctttaa ttcact atg aag ttc ttc agc act       54
                                        Met Lys Phe Phe Ser Thr
                                         1               5 ctt agc acc ctt gcg gtg gcc ctc atg atg agt ggc gag gct ctg gct      102
Leu Ser Thr Leu Ala Val Ala Leu Met Met Ser Gly Glu Ala Leu Ala
            10                  15                  20 ggt acc tac aag ggt ttc agc att ggc gcc aac agg gct gat ggt gcc      150
Gly Thr Tyr Lys Gly Phe Ser Ile Gly Ala Asn Arg Ala Asp Gly Ala
        25                  30                  35 tgt aag tgg gag gcc gac tgg aag aag gat ttc cag gcc atc aag agc      198
Cys Lys Trp Glu Ala Asp Trp Lys Lys Asp Phe Gln Ala Ile Lys Ser
    40                  45                  50 tgg aac aag ggt ttc aac gct gtt cgt ctg tac tct gcc tct gac tgt      246
Trp Asn Lys Gly Phe Asn Ala Val Arg Leu Tyr Ser Ala Ser Asp Cys
 55                  60                  65                  70 aac aca ctt gtc aag gct gtc ccc gct gcc aag gcc act ggc atg aag      294
Asn Thr Leu Val Lys Ala Val Pro Ala Ala Lys Ala Thr Gly Met Lys
                75                  80                  85 atc ctt gtt ggc gtc tgg gcc acc gat gat gct cac ttc ggc cgc gac      342
Ile Leu Val Gly Val Trp Ala Thr Asp Asp Ala His Phe Gly Arg Asp
            90                  95                 100 aag gcc gcc ctc ctc aag gct atc aag cag cac ggc acc ggc tgg atc      390
Lys Ala Ala Leu Leu Lys Ala Ile Lys Gln His Gly Thr Gly Trp Ile
        105                 110                 115 gcc gcc atc agt gtc gga tcc gag gac ctc tac cgt gag gac atc tcc      438
Ala Ala Ile Ser Val Gly Ser Glu Asp Leu Tyr Arg Glu Asp Ile Ser
    120                 125                 130 ccc cag aag ctc gca cag cag atc tac gac gtc cga ggc atg gtc cac      486
Pro Gln Lys Leu Ala Gln Gln Ile Tyr Asp Val Arg Gly Met Val His
135                 140                 145                 150 caa tac aac aag aac ctc aag gtc gga cat acc gac acc tgg acc gct      534
Gln Tyr Asn Lys Asn Leu Lys Val Gly His Thr Asp Thr Trp Thr Ala
                155                 160                 165 tgg gtc gac ggc cgc aac gac gtc gtc acc aag gcc tgc gat atc gcc      582
```

```
Trp Val Asp Gly Arg Asn Asp Val Val Thr Lys Ala Cys Asp Ile Ala
            170                 175                 180 att aca aac ggt ttc ccc tac tgg cag ggt gtt ccc atc aag gat gct        630
Ile Thr Asn Gly Phe Pro Tyr Trp Gln Gly Val Pro Ile Lys Asp Ala
            185                 190                 195 ctc cgc ctc aag acc ttc cag aac tcc ttc tgg aac gtc cag aag cac        678
Leu Arg Leu Lys Thr Phe Gln Asn Ser Phe Trp Asn Val Gln Lys His
        200                 205                 210 gtc aag gct gtc aac tcc aag gct gct gtc tgg gtt ggc gag acc ggc        726
Val Lys Ala Val Asn Ser Lys Ala Ala Val Trp Val Gly Glu Thr Gly
215                 220                 225                 230 tgg cct aca aag gga ccc aac tac cag aag gct gct gcc acg acc gcc        774
Trp Pro Thr Lys Gly Pro Asn Tyr Gln Lys Ala Ala Ala Thr Thr Ala
            235                 240                 245 agt ctc cag cag ttc tac aac aat gtc ggt tgc tgg ctc tgg cag cag        822
Ser Leu Gln Gln Phe Tyr Asn Asn Val Gly Cys Trp Leu Trp Gln Gln
            250                 255                 260 aag gag gcc agt ggt ttc tgg ttc act gct ttc gat aca cct gcg cac        870
Lys Glu Ala Ser Gly Phe Trp Phe Thr Ala Phe Asp Thr Pro Ala His
            265                 270                 275 agc acc gag gtt gag aag tac ttc ggt att gcc aac cag gac cgc aag        918
Ser Thr Glu Val Glu Lys Tyr Phe Gly Ile Ala Asn Gln Asp Arg Lys
        280                 285                 290 ctc aag ttc agc ctt act tgc taa gcgttgtagc gggttttcga tgtataaatt       972
Leu Lys Phe Ser Leu Thr Cys
295                 300 taatttacca tatactgtta gcgcttgtca acttgatagt atttccattc a               1023

<210> SEQ ID NO 2
<211> LENGTH: 301
<212> TYPE: PRT
<213> ORGANISM: Fusarium venenatum

<400> SEQUENCE: 2

Met Lys Phe Phe Ser Thr Leu Ser Thr Leu Ala Val Ala Leu Met Met
 1               5                  10                  15

Ser Gly Glu Ala Leu Ala Gly Thr Tyr Lys Gly Phe Ser Ile Gly Ala
            20                  25                  30

Asn Arg Ala Asp Gly Ala Cys Lys Trp Glu Ala Asp Trp Lys Lys Asp
        35                  40                  45

Phe Gln Ala Ile Lys Ser Trp Asn Lys Gly Phe Asn Ala Val Arg Leu
    50                  55                  60

Tyr Ser Ala Ser Asp Cys Asn Thr Leu Val Lys Ala Val Pro Ala Ala
65                  70                  75                  80

Lys Ala Thr Gly Met Lys Ile Leu Val Gly Val Trp Ala Thr Asp Asp
                85                  90                  95

Ala His Phe Gly Arg Asp Lys Ala Ala Leu Leu Lys Ala Ile Lys Gln
            100                 105                 110

His Gly Thr Gly Trp Ile Ala Ala Ile Ser Val Gly Ser Glu Asp Leu
        115                 120                 125

Tyr Arg Glu Asp Ile Ser Pro Gln Lys Leu Ala Gln Gln Ile Tyr Asp
    130                 135                 140

Val Arg Gly Met Val His Gln Tyr Asn Lys Asn Leu Lys Val Gly His
145                 150                 155                 160

Thr Asp Thr Trp Thr Ala Trp Val Asp Gly Arg Asn Asp Val Val Thr
                165                 170                 175

Lys Ala Cys Asp Ile Ala Ile Thr Asn Gly Phe Pro Tyr Trp Gln Gly
```

-continued

```
            180                 185                 190

Val Pro Ile Lys Asp Ala Leu Arg Leu Lys Thr Phe Gln Asn Ser Phe
        195                 200                 205

Trp Asn Val Gln Lys His Val Lys Ala Val Asn Ser Lys Ala Ala Val
    210                 215                 220

Trp Val Gly Glu Thr Gly Trp Pro Thr Lys Gly Pro Asn Tyr Gln Lys
225                 230                 235                 240

Ala Ala Ala Thr Thr Ala Ser Leu Gln Gln Phe Tyr Asn Asn Val Gly
                245                 250                 255

Cys Trp Leu Trp Gln Gln Lys Glu Ala Ser Gly Phe Trp Phe Thr Ala
            260                 265                 270

Phe Asp Thr Pro Ala His Ser Thr Glu Val Glu Lys Tyr Phe Gly Ile
        275                 280                 285

Ala Asn Gln Asp Arg Lys Leu Lys Phe Ser Leu Thr Cys
    290                 295                 300

<210> SEQ ID NO 3
<211> LENGTH: 3622
<212> TYPE: DNA
<213> ORGANISM: Fusarium sporotrichioides
<220> FEATURE:
<221> NAME/KEY: CDS
<222> LOCATION: (1801)..(2014)
<221> NAME/KEY: CDS
<222> LOCATION: (2070)..(2761)

<400> SEQUENCE: 3
attgaatcgt aacgatagcc tcatgcttgg cattttgtgc cttgacatta tcgagcgcgg     60
caccccacag gccttggtct ctgaaagaaa cggtggtggc gccgtttttt gcaaggttaa    120
tcccacttcc aggcttcttg gtgacgttga gaagtgcatc gccccagcct ccgcccgtag    180
caacagttga gtctcctgta aggatgaaaa agggcgattt cgcagcctga acaccaccaa    240
agatgctcag ggcagcagaa gcaatggcca agaatctcat gctgagtaaa gatgattcag    300
atatgattct cgaaaaaaat gacttcaatc gcgtcgctac ttgaaagtat catcttcttc    360
tatatattga ccacggaccc caacatctgc cgaacactca taagtcgttt gcctcttcat    420
gattgagaaa gtggaatatt tccaccaata aacatcatgc attgactttg ggggcataaa    480
tgtcaaggtt tgcagggact gtattcatgt tcagaatccg aaccatctga ccttatgtta    540
ctcccccatg ccatgcggag aatcactgat cgtcaggctt agaaaggcga ctaagtggtt    600
gaactgtacc tcggctttca cattcggtct tgaatagccc gagtttctcg ctcgacctcg    660
ccgttagtaa cagggacagg cagtgggttg gactacctac cagactacct actgtgtttc    720
cccttgatct gatggcttta tcgataggca tatctaatct aatctcgatt tgtgctatct    780
aatctcactt tatcgtttct tatctgagta ataaccttac tcctatttta tccagtattg    840
aggtattaaa tgtcttgtgt aaatgaaaga ataaggggat aaaacgtagt atagagacct    900
attcagtgtt tgtatgaatg cttataatcc tgaactgagt tgaggacagt agtgggttgg    960
tttcttttga tcttttggtt gacttactca gctgaatttg cttaactcaa aacaacaacg   1020
ctctacgcag gtgacctatt ttcagcacaa gatcattacc attgggataa tgttccatta   1080
gcctgcagtt ctgatagact aataagctct catatgacca ggtttggcca tgttgaaggt   1140
ctgattgatg aaattgatga gtgttgtagg gtagatcaag gtagactaat ggagaattga   1200
gaaacctggc gaaggtgaaa agcggaggat ccggtgcttc cgaccaataa tcggacagca   1260
tcgcgtggac aatcgatagc caaggaagat ctcttagcct ggttccatta ttctttgatc   1320
```

-continued

```
ttgtggttgg ctaaccatct tgatttaacc aagatagcac agaacagagc agacatcgtt    1380
ttgcatcatg gatccaactc aggccgacta acccgtagtg aggcgtttcg aatttctcca    1440
gatacccaaa gatggattaa gcatgaaaac caatctgctt taattgcccg tagattgaat    1500
ccattctggc gaagccgatg ttccgcgcaa caccgtcctt tctagcgcca ttccaagacc    1560
aggccaagca taaaaatagc accacacacg gcaaaaaagg tctagaacag ctcacgctcc    1620
agggtgaata cgagcccaaa ggggcaaaaa gcaacaagaa aaaggggca taatttccat    1680 catcccataa taaaaccaac tttccacccc aactttcttg cctttttgtc ctcttggctc    1740
tttaactgtc actcgcttat taatcagtta ttttctttca tttactatcg ttaattcact    1800 atg aag ttc ttc agc act ctc agc acc ctt gcg gtg gct ctc atg atg    1848
Met Lys Phe Phe Ser Thr Leu Ser Thr Leu Ala Val Ala Leu Met Met
  1               5                  10                  15 agt ggc gag gcc cta gcc ggt acc tac aag ggt ttc agc att ggc gcc    1896
Ser Gly Glu Ala Leu Ala Gly Thr Tyr Lys Gly Phe Ser Ile Gly Ala
             20                  25                  30 aac agg gct gat ggc gcc tgc aag tgg gag gcc gac tgg aag aag gat    1944
Asn Arg Ala Asp Gly Ala Cys Lys Trp Glu Ala Asp Trp Lys Lys Asp
         35                  40                  45 ttc cag gcc atc aag agc tgg aac aag ggt ttc aac gct gtt cgt ctg    1992
Phe Gln Ala Ile Lys Ser Trp Asn Lys Gly Phe Asn Ala Val Arg Leu
     50                  55                  60 tac tct gct agt gat tgc aac a gtaagcgttc cgcattctga acaacaataa     2044
Tyr Ser Ala Ser Asp Cys Asn
 65                  70 gctctttttac ttacgttctt cttag ca ctt gtc aag gcc gtc ccc gct gct    2095
                               Thr Leu Val Lys Ala Val Pro Ala Ala
                                                75                  80 aag gcc act ggc atg aag atc ctt gtc ggc gtt tgg gcc acc gac gat    2143
Lys Ala Thr Gly Met Lys Ile Leu Val Gly Val Trp Ala Thr Asp Asp
                     85                  90                  95 gct cac ttc ggc cgc gat aag gcc gct ctt ctc aag gct att aag cag    2191
Ala His Phe Gly Arg Asp Lys Ala Ala Leu Leu Lys Ala Ile Lys Gln
                100                 105                 110 cac ggc acg ggc tgg atc gcc gcc atc agc gtc gga tcc gaa gac ctc    2239
His Gly Thr Gly Trp Ile Ala Ala Ile Ser Val Gly Ser Glu Asp Leu
            115                 120                 125 tac cgt gag gat atc tcc ccc cag aag ctc gcc cag cag atc tac gat    2287
Tyr Arg Glu Asp Ile Ser Pro Gln Lys Leu Ala Gln Gln Ile Tyr Asp
130                 135                 140 gtc cga ggc atg gtc cac caa tac aac aag aat ctc aag gtc gga cac    2335
Val Arg Gly Met Val His Gln Tyr Asn Lys Asn Leu Lys Val Gly His
145                 150                 155                 160 acc gac acc tgg acc gct tgg gtc gac ggc cgc aat gac gtc gtc acc    2383
Thr Asp Thr Trp Thr Ala Trp Val Asp Gly Arg Asn Asp Val Val Thr
                165                 170                 175 aag gcc tgc gac att gcc atc aca aac ggt ttc ccc tac tgg cag ggt    2431
Lys Ala Cys Asp Ile Ala Ile Thr Asn Gly Phe Pro Tyr Trp Gln Gly
                180                 185                 190 gtc ccc atc aag gat gct ctc cgt ctc aag act ttc cag aac tcg tac    2479
Val Pro Ile Lys Asp Ala Leu Arg Leu Lys Thr Phe Gln Asn Ser Tyr
                195                 200                 205 tgg aac gtc aag aag cac gtc aat gct gtc aac tcc aag gct gct gtc    2527
Trp Asn Val Lys Lys His Val Asn Ala Val Asn Ser Lys Ala Ala Val
        210                 215                 220 tgg gtt ggt gag acc ggc tgg cct acc aag gga ccc aac tac cag aag    2575
Trp Val Gly Glu Thr Gly Trp Pro Thr Lys Gly Pro Asn Tyr Gln Lys
```

```
                225                 230                 235                 240
gct gct gcc acg acc gcc agt ctg cag cag ttc tac aac aat gtc ggt       2623
Ala Ala Ala Thr Thr Ala Ser Leu Gln Gln Phe Tyr Asn Asn Val Gly
                245                 250                 255 tgc tgg ctc tgg cag cag aag gat gcc agt ggt ttc tgg ttc act gct       2671
Cys Trp Leu Trp Gln Gln Lys Asp Ala Ser Gly Phe Trp Phe Thr Ala
                260                 265                 270 ttc gat act cct gcc cac agc act gaa gtt gag aag tac ttc ggt att       2719
Phe Asp Thr Pro Ala His Ser Thr Glu Val Glu Lys Tyr Phe Gly Ile
                275                 280                 285 gct aac cag gac cgc aag ctc aag ttc ggc ctt act tgc taa               2761
Ala Asn Gln Asp Arg Lys Leu Lys Phe Gly Leu Thr Cys
                290                 295                 300 acgttgtagc ggggttgcca tgtataaatt taattgacca tatactgttg gcgtttatca     2821
acttgatagt acttacattc attgcataaa aaagtctttc ttagatccaa tatataatat     2881
caaagaccga tcacattcaa taatcttctt gtctatctat gcaaggccat tcatttcctt     2941
aagccttggt gcttccagga ggacccaggt aactctcttg cacccaccg aagtcgacga      3001 caacctttc caacaagatg ttcgcatggt taagtcggag cttgaggtta tgcacaccag      3061
tctttaacag ccccagctca tgcctccgta cccatacgtt gtccgacgca gcaaagaacc    3121
acccgtcagc cgacgcccat cccttgtctg cggcgttctt ctcgctctgc ggagtccttc    3181
tctgtaaatt gtacgtctga ctcgggcctt cgtcaatctg cacatcgtag gtcaggacat    3241
cctcgggtga caagtcgaga gttgttccaa agtaaagcac cagctccgtc ttgtcagttt    3301
cgctgtgcgt gaagagcggg tatttcatgt aaggaatctc gctattggtc cttgtcccgg    3361
gagcgagagt cacacttccg gtctcgagtc tgcctgtatc aggaagcatc agatacggct    3421
tctccatgtg acaatcagtt gctggtatcg agatataaca gtcttgctcc acaaagccac    3481
ggaatgaatc ttggacatgt cgcccgtcaa tgagtaggtg gacttgttca agtctcctt    3541 cacgcgactg tacatcaata agaacctcct cttggaagtc ttgaggcact tgtgaccaat    3601
tgatagaaac ttggactcgc a                                              3622
```

<210> SEQ ID NO 4
<211> LENGTH: 301
<212> TYPE: PRT
<213> ORGANISM: Fusarium sporotrichioides

<400> SEQUENCE: 4

```
Met Lys Phe Phe Ser Thr Leu Ser Thr Leu Ala Val Ala Leu Met Met
  1               5

Tyr Arg Glu Asp Ile Ser Pro Gln Lys Leu Ala Gln Gln Ile Tyr Asp
     130                 135                 140

Val Arg Gly Met Val His Gln Tyr Asn Lys Asn Leu Lys Val Gly His
145                 150                 155                 160

Thr Asp Thr Trp Thr Ala Trp Val Asp Gly Arg Asn Asp Val Val Thr
                165                 170                 175

Lys Ala Cys Asp Ile Ala Ile Thr Asn Gly Phe Pro Tyr Trp Gln Gly
            180                 185                 190

Val Pro Ile Lys Asp Ala Leu Arg Leu Lys Thr Phe Gln Asn Ser Tyr
        195                 200                 205

Trp Asn Val Lys Lys His Val Asn Ala Val Asn Ser Lys Ala Ala Val
    210                 215                 220

Trp Val Gly Glu Thr Gly Trp Pro Thr Lys Gly Pro Asn Tyr Gln Lys
225                 230                 235                 240

Ala Ala Ala Thr Thr Ala Ser Leu Gln Gln Phe Tyr Asn Asn Val Gly
                245                 250                 255

Cys Trp Leu Trp Gln Gln Lys Asp Ala Ser Gly Phe Trp Phe Thr Ala
            260                 265                 270

Phe Asp Thr Pro Ala His Ser Thr Glu Val Glu Lys Tyr Phe Gly Ile
        275                 280                 285

Ala Asn Gln Asp Arg Lys Leu Lys Phe Gly Leu Thr Cys
    290                 295                 300

<210> SEQ ID NO 5
<211> LENGTH: 301
<212> TYPE: PRT
<213> ORGANISM: Fusarium venenatum

<400> SEQUENCE: 5

Met Lys Phe Phe Ser Thr Leu Ser Thr Leu Ala Val Ala Leu Met Met
  1               5                  10                  15

Ser Gly Glu Ala Leu Ala Gly Thr Tyr Lys Gly Phe Ser Ile Gly Ala
                20                  25                  30

Asn Arg Ala Asp Gly Ala Cys Lys Trp Glu Ala Asp Trp Lys Lys Asp
            35                  40                  45

Phe Gln Ala Ile Lys Ser Trp Asn Lys Gly Phe Asn Ala Val Arg Leu
        50                  55                  60

Tyr Ser Ala Ser Asp Cys Asn Thr Leu Val Lys Ala Val Pro Ala Ala
 65                  70                  75                  80

Lys Ala Thr Gly Met Lys Ile Leu Val Gly Val Trp Ala Thr Asp Asp
                85                  90                  95

Ala His Phe Gly Arg Asp Lys Ala Ala Leu Leu Lys Ala Ile Lys Gln
            100                 105                 110

His Gly Thr Gly Trp Ile Ala Ala Ile Ser Val Gly Ser Glu Asp Leu
        115                 120                 125

Tyr Arg Glu Asp Ile Ser Pro Gln Lys Leu Ala Gln Gln Ile Tyr Asp
    130                 135                 140

Val Arg Gly Met Val His Gln Tyr Asn Lys Asn Leu Lys Val Gly His
145                 150                 155                 160

Thr Asp Thr Trp Thr Ala Trp Val Asp Gly Arg Asn Asp Val Val Thr
                165                 170                 175

Lys Ala Cys Asp Ile Ala Ile Thr Asn Gly Phe Pro Tyr Trp Lys Gly
            180                 185                 190

Val Pro Ile Lys Asp Ala Leu Arg Leu Lys Thr Phe Gln Asn Ser Phe

```
                195                 200                 205
Trp Asn Val Gln Lys His Val Lys Ala Val Asn Ser Lys Ala Ala Val
        210                 215                 220
Trp Val Gly Glu Thr Gly Trp Pro Thr Lys Gly Pro Asn Tyr Gln Lys
225                 230                 235                 240
Ala Ala Ala Thr Thr Ala Ser Leu Gln Gln Phe Tyr Asn Asn Val Gly
                245                 250                 255
Cys Trp Leu Trp Gln Gln Lys Glu Ala Ser Gly Phe Trp Phe Thr Ala
        260                 265                 270
Phe Asp Thr Pro Ala His Ser Thr Glu Val Glu Lys Tyr Phe Gly Ile
        275                 280                 285
Ala Asn Gln Asp Arg Lys Leu Lys Phe Ser Leu Thr Cys
        290                 295                 300

<210> SEQ ID NO 6
<211> LENGTH: 467
<212> TYPE: DNA
<213> ORGANISM: Fusarium venenatum
<220> FEATURE:
<221> NAME/KEY: CDS
<222> LOCATION: (186)..(467)

<400> SEQUENCE: 6
gattcattcc ccacctaaaa ccctccaagt gccctccatc atcacgaatc tccacagaga      60
cagccaagat acgccttgga aatcgtacca gggcgagcct tttacttata accgccgttt     120
tcgctgcatt agttgcagta ttcctatcaa atacatcttt atctagtccc tttacttcaa     180 tcaaa atg ggt ggt gga ccc gaa ggt ttc cgc acc gtt gcg tat ttc gtc      230
      Met Gly Gly Gly Pro Glu Gly Phe Arg Thr Val Ala Tyr Phe Val
      1               5                   10                  15 aac tgg gct atc tat gca cga aag cat cgt cct cag gat ctt ccc gtg       278
Asn Trp Ala Ile Tyr Ala Arg Lys His Arg Pro Gln Asp Leu Pro Val
            20                  25                  30 gag aac ctg aca cat att ctt tac tcg ttc gct aat att cgt agc gac       326
Glu Asn Leu Thr His Ile Leu Tyr Ser Phe Ala Asn Ile Arg Ser Asp
        35                  40                  45 tct ggc gaa gtc cat ctc acc gac tca tgg gcc gat acc gat att cat       374
Ser Gly Glu Val His Leu Thr Asp Ser Trp Ala Asp Thr Asp Ile His
    50                  55                  60 tgg gat gga gat tcc tgg aat gat gtc ggt acc aac ttg tac ggt tgc       422
Trp Asp Gly Asp Ser Trp Asn Asp Val Gly Thr Asn Leu Tyr Gly Cys
65                  70                  75 atg aag cag ctt aac ctg ttg aaa aga cgt aac cga aac ctc aag           467
Met Lys Gln Leu Asn Leu Leu Lys Arg Arg Asn Arg Asn Leu Lys
 80                  85                  90

<210> SEQ ID NO 7
<211> LENGTH: 94
<212> TYPE: PRT
<213> ORGANISM: Fusarium venenatum

<400> SEQUENCE: 7

Met Gly Gly Gly Pro Glu Gly Phe Arg Thr Val Ala Tyr Phe Val Asn
1               5                   10                  15

Trp Ala Ile Tyr Ala Arg Lys His Arg Pro Gln Asp Leu Pro Val Glu
            20                  25                  30

Asn Leu Thr His Ile Leu Tyr Ser Phe Ala Asn Ile Arg Ser Asp Ser
        35                  40                  45

Gly Glu Val His Leu Thr Asp Ser Trp Ala Asp Thr Asp Ile His Trp
```

```
                50                    55                    60
Asp Gly Asp Ser Trp Asn Asp Val Gly Thr Asn Leu Tyr Gly Cys Met
 65                  70                    75                    80

Lys Gln Leu Asn Leu Leu Lys Arg Arg Asn Arg Asn Leu Lys
                 85                    90

<210> SEQ ID NO 8
<211> LENGTH: 995
<212> TYPE: DNA
<213> ORGANISM: Fusarium sporotrichioides
<220> FEATURE:
<221> NAME/KEY: CDS
<222> LOCATION: (160)..(303)
<221> NAME/KEY: CDS
<222> LOCATION: (392)..(469)
<221> NAME/KEY: misc_difference
<222> LOCATION: (283)
<223> OTHER INFORMATION: Unsure, n is A or C; Xaa at amino acid 42 is
      Ile or Leu

<400> SEQUENCE: 8
gattcccaag ggggcggaac tggaagatca tcgccggtct tattaaacgg gnactggtac      60
tttggacact tttgtctctt ccttaaagat tagcctccct cgctcagctt ctatctacca    120
ttgttagcaa ttatctcact cacctcacct ctaggcgta atg tgg tcc aag gct       174
                                             Met Trp Ser Lys Ala
                                              1               5 ctt ctg gcc gtt gcc gcc ttt gcc ttc aca ccc gcc aat gct ata tgg      222
Leu Leu Ala Val Ala Ala Phe Ala Phe Thr Pro Ala Asn Ala Ile Trp
             10                  15                  20 cca gtg cca aag aag atc tct act gga gac aag gcc ctc ttc atc gat      270
Pro Val Pro Lys Lys Ile Ser Thr Gly Asp Lys Ala Leu Phe Ile Asp
         25                  30                  35 caa acg att gac ntc acc tac aat gga gac ttt gtacgggact ctccccggtt    323
Gln Thr Ile Asp Xaa Thr Tyr Asn Gly Asp Phe
     40                  45 ctgattccga ttctggtgct tgtaaccata ccgcgcagct caatactgaa actttgcttc    383 acaaacag atc ccc tac act tac aat tac caa ccc gat gct ggc tcc aag     433
        Ile Pro Tyr Thr Tyr Asn Tyr Gln Pro Asp Ala Gly Ser Lys
         50                  55                  60 ttc agt agc aag caa atc atc caa gcc ggc gtc tct cgtgccctcc           479
Phe Ser Ser Lys Gln Ile Ile Gln Ala Gly Val Ser
         65                  70 aaggcgtctt ccaggacaac tttgtcccat ggatgctccg cgaacgcgac tccgattttg    539
agcctgacct gcaaaagaag cagtgggtga agtcgctaaa gattatccag accgaggagg    599
atgacgagag caccttcaag cctctcaatg gtgaggttga cgagtcgtac tccctctcac    659
tttctgagaa gggcgaggct tccatcaagg ccaagtcctc tacaggtgtc ctgcacggac    719
ttgagacctt tgtccaactt tcttcaagc acagctctgg cacttcctgg tacacgccgc    779
acgcgcctgt ctcgatccag gacgagcccg agtaccctca tcgaggtatc cttctcgatg    839
ttgcccgtag cttttttgaa gtcaagcaca tcaagcgcac aatcgatgcc atgtcgtgga    899
gcaagttgaa tcgccttcac ctccacatca ctgactcgca gtcctggcct ctcgagatcc    959
cagccctgcc caagctggcc gaaaagggcg cgtacc                              995

<210> SEQ ID NO 9
<211> LENGTH: 74
<212> TYPE: PRT
<213> ORGANISM: Fusarium sporotrichioides
<220> FEATURE:
```

```
<221> NAME/KEY: UNSURE
<222> LOCATION: (42)
<223> OTHER INFORMATION: Xaa is Ile or Leu

<400> SEQUENCE: 9

Met Trp Ser Lys Ala Leu Leu Ala Val Ala Ala Phe Ala Phe Thr Pro
 1               5                  10                  15

Ala Asn Ala Ile Trp Pro Val Pro Lys Lys Ile Ser Thr Gly Asp Lys
             20                  25                  30

Ala Leu Phe Ile Asp Gln Thr Ile Asp Xaa Thr Tyr Asn Gly Asp Phe
         35                  40                  45

Ile Pro Tyr Thr Tyr Asn Tyr Gln Pro Asp Ala Gly Ser Lys Phe Ser
     50                  55                  60

Ser Lys Gln Ile Ile Gln Ala Gly Val Ser
 65                  70

<210> SEQ ID NO 10
<211> LENGTH: 1494
<212> TYPE: DNA
<213> ORGANISM: Fusarium venenatum
<220> FEATURE:
<221> NAME/KEY: CDS
<222> LOCATION: (186)..(1385)

<400> SEQUENCE: 10
```

| | |
|---|---:|
| gattcattcc ccacctaaaa ccctccaagt gccctccatc atcacgaatc tccacagaga | 60 |
| cagccaagat acgccttgga aatcgtacca gggcgagcct tttacttata accgccgttt | 120 |
| tcgctgcatt agttgcagta ttcctatcaa atacatcttt atctagtccc tttacttcaa | 180 |

```
tcaaa atg ggt ggt gga ccc gaa ggt ttc cgc acc gtt gcg tat ttc gtc     230
      Met Gly Gly Gly Pro Glu Gly Phe Arg Thr Val Ala Tyr Phe Val
       1               5                  10                  15 aac tgg gct atc tat gca cga aag cat cgt cct cag gat ctt ccc gtg     278
Asn Trp Ala Ile Tyr Ala Arg Lys His Arg Pro Gln Asp Leu Pro Val
             20                  25                  30 gag aac ctg aca cat att ctt tac tcg ttc gct aat att cgt agc gac     326
Glu Asn Leu Thr His Ile Leu Tyr Ser Phe Ala Asn Ile Arg Ser Asp
         35                  40                  45 tct ggc gaa gtc cat ctc acc gac tca tgg gcc gat acc gat att cat     374
Ser Gly Glu Val His Leu Thr Asp Ser Trp Ala Asp Thr Asp Ile His
     50                  55                  60 tgg gat gga gat tcc tgg aat gat gtc ggt acc aac ttg tac ggt tgc     422
Trp Asp Gly Asp Ser Trp Asn Asp Val Gly Thr Asn Leu Tyr Gly Cys
 65                  70                  75 atg aag cag ctt aac ctg ttg aaa aga cgt aac cga aac ctc aag gtt     470
Met Lys Gln Leu Asn Leu Leu Lys Arg Arg Asn Arg Asn Leu Lys Val
 80                  85                  90                  95 ctt ctc agt att gga ggt tgg acc ttc agt agc aac ttc aag ggc ccc     518
Leu Leu Ser Ile Gly Gly Trp Thr Phe Ser Ser Asn Phe Lys Gly Pro
                100                 105                 110 gct agc aca ccc caa gga cgt gac aca ttc gcc aag agc tgt gtc gat     566
Ala Ser Thr Pro Gln Gly Arg Asp Thr Phe Ala Lys Ser Cys Val Asp
            115                 120                 125 ctg atc aag aac ctc ggt ttt gac ggt ata gat atc gat tgg gag tac     614
Leu Ile Lys Asn Leu Gly Phe Asp Gly Ile Asp Ile Asp Trp Glu Tyr
        130                 135                 140 ccc cag gat gcc aac gag gct aga aac tat gtc gaa ctt ctg ggc gcc     662
Pro Gln Asp Ala Asn Glu Ala Arg Asn Tyr Val Glu Leu Leu Gly Ala
    145                 150                 155 gtg cgt cat gag atg gat gca tat gca cag aca ttg agc caa cct tat     710
```

| | | |
|---|---|---|
| Val Arg His Glu Met Asp Ala Tyr Ala Gln Thr Leu Ser Gln Pro Tyr<br>160                 165                 170                 175 | | |

```
cac ttt gag ttg act gtg gcc tgt cca gcc ggt gcg aca aac ttc cag        758
His Phe Glu Leu Thr Val Ala Cys Pro Ala Gly Ala Thr Asn Phe Gln
            180                 185                 190 aag ctc gat atc cgt gga atg gat caa tac ctc gac ttc tgg aac ctc        806
Lys Leu Asp Ile Arg Gly Met Asp Gln Tyr Leu Asp Phe Trp Asn Leu
                195                 200                 205 atg gct tac gac tat gct ggt tct tgg gac caa act gcg ggt cat cag        854
Met Ala Tyr Asp Tyr Ala Gly Ser Trp Asp Gln Thr Ala Gly His Gln
            210                 215                 220 gcc aac ctg tac cca tct cac gac aac cca gta tca acc cca ttc tct        902
Ala Asn Leu Tyr Pro Ser His Asp Asn Pro Val Ser Thr Pro Phe Ser
225                 230                 235 acc tct gct gcc atc gac ttt tac gtc cgc agc ggt gtg aac cct tca        950
Thr Ser Ala Ala Ile Asp Phe Tyr Val Arg Ser Gly Val Asn Pro Ser
240                 245                 250                 255 aag ata gtt ctc ggc atg cca ctc tac ggc cga gcc ttt gag aac acc        998
Lys Ile Val Leu Gly Met Pro Leu Tyr Gly Arg Ala Phe Glu Asn Thr
                260                 265                 270 gac ggt ccc ggc cgc ccc tac caa ggc gtt gga caa ggt tcc tgg gaa       1046
Asp Gly Pro Gly Arg Pro Tyr Gln Gly Val Gly Gln Gly Ser Trp Glu
            275                 280                 285 cag gga gtc tac gat tac aag gcg ctt ccc cta gag ggc gcg caa gag       1094
Gln Gly Val Tyr Asp Tyr Lys Ala Leu Pro Leu Glu Gly Ala Gln Glu
            290                 295                 300 tac gga gat aga gga tgc tgt gcc agc tac tgc tac aac cct cag tca       1142
Tyr Gly Asp Arg Gly Cys Cys Ala Ser Tyr Cys Tyr Asn Pro Gln Ser
305                 310                 315 cgt acc atg gtc acc tac gac acg ccg cgg gtc gcc tgg gat aag gcc       1190
Arg Thr Met Val Thr Tyr Asp Thr Pro Arg Val Ala Trp Asp Lys Ala
320                 325                 330                 335 gag tat gtg aag agg tgg aag ctg gga ggc gct atg tgg tgg gag agc       1238
Glu Tyr Val Lys Arg Trp Lys Leu Gly Gly Ala Met Trp Trp Glu Ser
                340                 345                 350 agc gcg gat aag cag ggc gag cag agt ttg atc aca acg gtt gtg aac       1286
Ser Ala Asp Lys Gln Gly Glu Gln Ser Leu Ile Thr Thr Val Val Asn
            355                 360                 365 gga ttc gga ggt cag gga gcg ctc atg aga cag gac aac tgt att gag       1334
Gly Phe Gly Gly Gln Gly Ala Leu Met Arg Gln Asp Asn Cys Ile Glu
            370                 375                 380 tat ccc gcg acc aag tac gat aac ttg cga aat ggg ttc ccg gac aat       1382
Tyr Pro Ala Thr Lys Tyr Asp Asn Leu Arg Asn Gly Phe Pro Asp Asn
385                 390                 395 tga ggcgctaaag tggagttggt gggtcagagg aagcagaaac attgatgata           1435
gtttgcaacg actcatagtg ataacatgaa taaatgaata gtaaaatat ccattacga      1494

<210> SEQ ID NO 11
<211> LENGTH: 399
<212> TYPE: PRT
<213> ORGANISM: Fusarium venenatum

<400> SEQUENCE: 11

Met Gly Gly Gly Pro Glu Gly Phe Arg Thr Val Ala Tyr Phe Val Asn
 1               5                  10                  15

Trp Ala Ile Tyr Ala Arg Lys His Arg Pro Gln Asp Leu Pro Val Glu
                20                  25                  30

Asn Leu Thr His Ile Leu Tyr Ser Phe Ala Asn Ile Arg Ser Asp Ser
            35                  40                  45
```

```
Gly Glu Val His Leu Thr Asp Ser Trp Ala Asp Thr Asp Ile His Trp
     50                  55                  60

Asp Gly Asp Ser Trp Asn Asp Val Gly Thr Asn Leu Tyr Gly Cys Met
 65                  70                  75                  80

Lys Gln Leu Asn Leu Leu Lys Arg Arg Asn Arg Asn Leu Lys Val Leu
                 85                  90                  95

Leu Ser Ile Gly Gly Trp Thr Phe Ser Ser Asn Phe Lys Gly Pro Ala
            100                 105                 110

Ser Thr Pro Gln Gly Arg Asp Thr Phe Ala Lys Ser Cys Val Asp Leu
        115                 120                 125

Ile Lys Asn Leu Gly Phe Asp Gly Ile Asp Ile Asp Trp Glu Tyr Pro
130                 135                 140

Gln Asp Ala Asn Glu Ala Arg Asn Tyr Val Glu Leu Leu Gly Ala Val
145                 150                 155                 160

Arg His Glu Met Asp Ala Tyr Ala Gln Thr Leu Ser Gln Pro Tyr His
                165                 170                 175

Phe Glu Leu Thr Val Ala Cys Pro Ala Gly Ala Thr Asn Phe Gln Lys
            180                 185                 190

Leu Asp Ile Arg Gly Met Asp Gln Tyr Leu Asp Phe Trp Asn Leu Met
        195                 200                 205

Ala Tyr Asp Tyr Ala Gly Ser Trp Asp Gln Thr Ala Gly His Gln Ala
210                 215                 220

Asn Leu Tyr Pro Ser His Asp Asn Pro Val Ser Thr Pro Phe Ser Thr
225                 230                 235                 240

Ser Ala Ala Ile Asp Phe Tyr Val Arg Ser Gly Val Asn Pro Ser Lys
                245                 250                 255

Ile Val Leu Gly Met Pro Leu Tyr Gly Arg Ala Phe Glu Asn Thr Asp
            260                 265                 270

Gly Pro Gly Arg Pro Tyr Gln Gly Val Gly Gln Gly Ser Trp Glu Gln
        275                 280                 285

Gly Val Tyr Asp Tyr Lys Ala Leu Pro Leu Glu Gly Ala Gln Glu Tyr
290                 295                 300

Gly Asp Arg Gly Cys Cys Ala Ser Tyr Cys Tyr Asn Pro Gln Ser Arg
305                 310                 315                 320

Thr Met Val Thr Tyr Asp Thr Pro Arg Val Ala Trp Asp Lys Ala Glu
                325                 330                 335

Tyr Val Lys Arg Trp Lys Leu Gly Gly Ala Met Trp Trp Glu Ser Ser
            340                 345                 350

Ala Asp Lys Gln Gly Glu Gln Ser Leu Ile Thr Thr Val Val Asn Gly
        355                 360                 365

Phe Gly Gly Gln Gly Ala Leu Met Arg Gln Asp Asn Cys Ile Glu Tyr
370                 375                 380

Pro Ala Thr Lys Tyr Asp Asn Leu Arg Asn Gly Phe Pro Asp Asn
385                 390                 395

<210> SEQ ID NO 12
<211> LENGTH: 1949
<212> TYPE: DNA
<213> ORGANISM: Fusarium sp.
<220> FEATURE:
<221> NAME/KEY: CDS
<222> LOCATION: (108)..(1853)
<221> NAME/KEY: misc_difference
<222> LOCATION: (231)
<223> OTHER INFORMATION: Unsure, n is A or C; Xaa at amino acid 42 is
      Ile or Leu
```

```
<400> SEQUENCE: 12
actggtactt tggacacttt tgtctcttcc ttaaagatta gcctccctcg ctcagcttct      60
atctaccatt gttagcaatt atctcactca cctcacctct aggcgta atg tgg tcc     116
                                                    Met Trp Ser
                                                      1 aag gct ctt ctg gcc gtt gcc gcc ttt gcc ttc aca ccc gcc aat gct     164
Lys Ala Leu Leu Ala Val Ala Ala Phe Ala Phe Thr Pro Ala Asn Ala
      5                  10                  15 ata tgg cca gtg cca aag aag atc tct act gga gac aag gcc ctc ttc     212
Ile Trp Pro Val Pro Lys Lys Ile Ser Thr Gly Asp Lys Ala Leu Phe
 20                  25                  30                  35 atc gat caa acg att gac ntc acc tac aat gga gac ttt atc ccc tac     260
Ile Asp Gln Thr Ile Asp Xaa Thr Tyr Asn Gly Asp Phe Ile Pro Tyr
                 40                  45                  50 act tac aat tac caa ccc gat gct ggc tcc aag ttc agt agc aag caa     308
Thr Tyr Asn Tyr Gln Pro Asp Ala Gly Ser Lys Phe Ser Ser Lys Gln
             55                  60                  65 atc atc caa gcc ggc gtc tct cgt gcc ctc caa ggc gtc ttc cag gac     356
Ile Ile Gln Ala Gly Val Ser Arg Ala Leu Gln Gly Val Phe Gln Asp
         70                  75                  80 aac ttt gtc cca tgg atg ctc cgc gaa cgc gac tcc gat ttt gag cct     404
Asn Phe Val Pro Trp Met Leu Arg Glu Arg Asp Ser Asp Phe Glu Pro
     85                  90                  95 gac ctg caa aag aag cag tgg gtg aag tcg cta aag att atc cag acc     452
Asp Leu Gln Lys Lys Gln Trp Val Lys Ser Leu Lys Ile Ile Gln Thr
100                 105                 110                 115 gag gag gat gac gag agc acc ttc aag cct ctc aat ggt gag gtt gac     500
Glu Glu Asp Asp Glu Ser Thr Phe Lys Pro Leu Asn Gly Glu Val Asp
                120                 125                 130 gag tcg tac tcc ctc tca ctt tct gag aag ggc gag gct tcc atc aag     548
Glu Ser Tyr Ser Leu Ser Leu Ser Glu Lys Gly Glu Ala Ser Ile Lys
            135                 140                 145 gcc aag tcc tct aca ggt gtc ctg cac gga ctt gag acc ttt gtc caa     596
Ala Lys Ser Ser Thr Gly Val Leu His Gly Leu Glu Thr Phe Val Gln
        150                 155                 160 ctt ttc ttc aag cac agc tct ggc act tcc tgg tac acg ccg cac gcg     644
Leu Phe Phe Lys His Ser Ser Gly Thr Ser Trp Tyr Thr Pro His Ala
    165                 170                 175 cct gtc tcg atc cag gat gag ccc gag tac cct cat cga ggc att ctt     692
Pro Val Ser Ile Gln Asp Glu Pro Glu Tyr Pro His Arg Gly Ile Leu
180                 185                 190                 195 ctc gat gtt gcc cgt agc ttt ttt gaa gtc aag cac atc aag cgc aca     740
Leu Asp Val Ala Arg Ser Phe Phe Glu Val Lys His Ile Lys Arg Thr
                200                 205                 210 atc gac gcc atg tcg tgg agc aag ctg aat cgc ctt cac ctt cac atc     788
Ile Asp Ala Met Ser Trp Ser Lys Leu Asn Arg Leu His Leu His Ile
            215                 220                 225 act gac tcg cag tcc tgg cct ctc gag atc cca gcc cta ccc aaa ctg     836
Thr Asp Ser Gln Ser Trp Pro Leu Glu Ile Pro Ala Leu Pro Lys Leu
        230                 235                 240 gcc gaa aag ggt gca tac cgc aaa ggc ctg acc tac tct cct gag gat     884
Ala Glu Lys Gly Ala Tyr Arg Lys Gly Leu Thr Tyr Ser Pro Glu Asp
    245                 250                 255 ctt gcc ggt att tat gag tat ggt atc cac cgc gga gtc gag gtc atc     932
Leu Ala Gly Ile Tyr Glu Tyr Gly Ile His Arg Gly Val Glu Val Ile
260                 265                 270                 275 atg gag att gac atg ccc ggc cat atc ggt gtc gtt gag ctt gcc tat     980
Met Glu Ile Asp Met Pro Gly His Ile Gly Val Val Glu Leu Ala Tyr
```

```
                     280                 285                 290
aag gat ctc att gtc gcg tac aat gag aag cct tat caa tgg tgg tgt    1028
Lys Asp Leu Ile Val Ala Tyr Asn Glu Lys Pro Tyr Gln Trp Trp Cys
            295                 300                 305 aag gag cca ccc tgt ggt gcg ttc cgc atg aac agc tct gat gtt tat    1076
Lys Glu Pro Pro Cys Gly Ala Phe Arg Met Asn Ser Ser Asp Val Tyr
        310                 315                 320 gac ttt ctc gac act ctt ttt gat gac ctc ttc cct cgc att tcc aag    1124
Asp Phe Leu Asp Thr Leu Phe Asp Asp Leu Phe Pro Arg Ile Ser Lys
    325                 330                 335 tac agt cct tac ttc cac ctt ggt gga gac gag ctc aac cac aac gat    1172
Tyr Ser Pro Tyr Phe His Leu Gly Gly Asp Glu Leu Asn His Asn Asp
340                 345                 350                 355 tcc aga ctt gac cct gat gtg cgc tct aac gag acc gag gtt ctg gcg    1220
Ser Arg Leu Asp Pro Asp Val Arg Ser Asn Glu Thr Glu Val Leu Ala
            360                 365                 370 cct ctt ttg caa aag ttc gtc gat tac act cac ggc aag gtt cga gat    1268
Pro Leu Leu Gln Lys Phe Val Asp Tyr Thr His Gly Lys Val Arg Asp
        375                 380                 385 gcc ggc atg act ccg ttc gtc tgg gag gag atg att acc gaa tgg aac    1316
Ala Gly Met Thr Pro Phe Val Trp Glu Glu Met Ile Thr Glu Trp Asn
    390                 395                 400 atg act ctg ggt aaa gac gtt gtg att cag tcc tgg ctc ggt ggc ggt    1364
Met Thr Leu Gly Lys Asp Val Val Ile Gln Ser Trp Leu Gly Gly Gly
405                 410                 415 gct atc aag acc ctg gct gag gct ggt cac aag gta atc gat agt gat    1412
Ala Ile Lys Thr Leu Ala Glu Ala Gly His Lys Val Ile Asp Ser Asp
420                 425                 430                 435 tac aac ttc tgg tac ctt gac tgt ggg cgt gga cag tgg ctc aac ttt    1460
Tyr Asn Phe Trp Tyr Leu Asp Cys Gly Arg Gly Gln Trp Leu Asn Phe
            440                 445                 450 gac aac ggc gat gcc ttt caa aca tac tac ccc ttc aac gac tgg tgc    1508
Asp Asn Gly Asp Ala Phe Gln Thr Tyr Tyr Pro Phe Asn Asp Trp Cys
        455                 460                 465 ggt cct acc aag agc tgg cgg ctc atc tac tcc cac gat cct cgg gcc    1556
Gly Pro Thr Lys Ser Trp Arg Leu Ile Tyr Ser His Asp Pro Arg Ala
    470                 475                 480 ggt cta tcc gag gaa gca gcc aag cgc gtg ctt ggt ggt gag gcg gcc    1604
Gly Leu Ser Glu Glu Ala Ala Lys Arg Val Leu Gly Gly Glu Ala Ala
485                 490                 495 gta tgg act gag act atc gac agt gtt aac ctc gat acc att gtg tgg    1652
Val Trp Thr Glu Thr Ile Asp Ser Val Asn Leu Asp Thr Ile Val Trp
500                 505                 510                 515 ccc cgc gct gca gtg atg gga gaa gtt ctc tgg tca ggc cga act gac    1700
Pro Arg Ala Ala Val Met Gly Glu Val Leu Trp Ser Gly Arg Thr Asp
            520                 525                 530 gcc tca ggc cag aac aga tcg cag tat gat gct gca ccg cga ctg gct    1748
Ala Ser Gly Gln Asn Arg Ser Gln Tyr Asp Ala Ala Pro Arg Leu Ala
        535                 540                 545 gag atg cgc gag cgt atg gtg gct cga gga gtg agt gct tca cca att    1796
Glu Met Arg Glu Arg Met Val Ala Arg Gly Val Ser Ala Ser Pro Ile
    550                 555                 560 cag atg ccc ttc tgt aca cag ggc aat gcc acc gag tgt gcg caa gtc    1844
Gln Met Pro Phe Cys Thr Gln Gly Asn Ala Thr Glu Cys Ala Gln Val
565                 570                 575 gag gga tga taaatttgac gcgtggtgca tctgtactta ttacgaatta           1893
Glu Gly
580 ctttgtacat agtttgttct cagcattttg aatagagaat tatttcccct ctttca    1949
```

<210> SEQ ID NO 13
<211> LENGTH: 581
<212> TYPE: PRT
<213> ORGANISM: Fusarium sp.
<220> FEATURE:
<221> NAME/KEY: UNSURE
<222> LOCATION: (42)
<223> OTHER INFORMATION: Xaa is Ile or Leu

<400> SEQUENCE: 13

```
Met Trp Ser Lys Ala Leu Leu Ala Val Ala Ala Phe Ala Phe Thr Pro
  1               5                  10                  15

Ala Asn Ala Ile Trp Pro Val Pro Lys Lys Ile Ser Thr Gly Asp Lys
             20                  25                  30

Ala Leu Phe Ile Asp Gln Thr Ile Asp Xaa Thr Tyr Asn Gly Asp Phe
         35                  40                  45

Ile Pro Tyr Thr Tyr Asn Tyr Gln Pro Asp Ala Gly Ser Lys Phe Ser
     50                  55                  60

Ser Lys Gln Ile Ile Gln Ala Gly Val Ser Arg Ala Leu Gln Gly Val
 65                  70                  75                  80

Phe Gln Asp Asn Phe Val Pro Trp Met Leu Arg Glu Arg Asp Ser Asp
                 85                  90                  95

Phe Glu Pro Asp Leu Gln Lys Lys Gln Trp Val Lys Ser Leu Lys Ile
            100                 105                 110

Ile Gln Thr Glu Glu Asp Asp Glu Ser Thr Phe Lys Pro Leu Asn Gly
        115                 120                 125

Glu Val Asp Glu Ser Tyr Ser Leu Ser Leu Ser Glu Lys Gly Glu Ala
130                 135                 140

Ser Ile Lys Ala Lys Ser Ser Thr Gly Val Leu His Gly Leu Glu Thr
145                 150                 155                 160

Phe Val Gln Leu Phe Phe Lys His Ser Ser Gly Thr Ser Trp Tyr Thr
                165                 170                 175

Pro His Ala Pro Val Ser Ile Gln Asp Glu Pro Glu Tyr Pro His Arg
            180                 185                 190

Gly Ile Leu Leu Asp Val Ala Arg Ser Phe Phe Glu Val Lys His Ile
        195                 200                 205

Lys Arg Thr Ile Asp Ala Met Ser Trp Ser Lys Leu Asn Arg Leu His
210                 215                 220

Leu His Ile Thr Asp Ser Gln Ser Trp Pro Leu Glu Ile Pro Ala Leu
225                 230                 235                 240

Pro Lys Leu Ala Glu Lys Gly Ala Tyr Arg Lys Gly Leu Thr Tyr Ser
                245                 250                 255

Pro Glu Asp Leu Ala Gly Ile Tyr Glu Tyr Gly Ile His Arg Gly Val
            260                 265                 270

Glu Val Ile Met Glu Ile Asp Met Pro Gly His Ile Gly Val Val Glu
        275                 280                 285

Leu Ala Tyr Lys Asp Leu Ile Val Ala Tyr Asn Glu Lys Pro Tyr Gln
290                 295                 300

Trp Trp Cys Lys Glu Pro Pro Cys Gly Ala Phe Arg Met Asn Ser Ser
305                 310                 315                 320

Asp Val Tyr Asp Phe Leu Asp Thr Leu Phe Asp Asp Leu Phe Pro Arg
                325                 330                 335

Ile Ser Lys Tyr Ser Pro Tyr Phe His Leu Gly Gly Asp Glu Leu Asn
            340                 345                 350
```

```
His Asn Asp Ser Arg Leu Asp Pro Asp Val Arg Ser Asn Glu Thr Glu
    355                 360                 365

Val Leu Ala Pro Leu Leu Gln Lys Phe Val Asp Tyr Thr His Gly Lys
370                 375                 380

Val Arg Asp Ala Gly Met Thr Pro Phe Val Trp Glu Glu Met Ile Thr
385                 390                 395                 400

Glu Trp Asn Met Thr Leu Gly Lys Asp Val Val Ile Gln Ser Trp Leu
                    405                 410                 415

Gly Gly Gly Ala Ile Lys Thr Leu Ala Glu Ala Gly His Lys Val Ile
            420                 425                 430

Asp Ser Asp Tyr Asn Phe Trp Tyr Leu Asp Cys Gly Arg Gly Gln Trp
    435                 440                 445

Leu Asn Phe Asp Asn Gly Asp Ala Phe Gln Thr Tyr Tyr Pro Phe Asn
    450                 455                 460

Asp Trp Cys Gly Pro Thr Lys Ser Trp Arg Leu Ile Tyr Ser His Asp
465                 470                 475                 480

Pro Arg Ala Gly Leu Ser Glu Glu Ala Ala Lys Arg Val Leu Gly Gly
                485                 490                 495

Glu Ala Ala Val Trp Thr Glu Thr Ile Asp Ser Val Asn Leu Asp Thr
                500                 505                 510

Ile Val Trp Pro Arg Ala Ala Val Met Gly Glu Val Leu Trp Ser Gly
        515                 520                 525

Arg Thr Asp Ala Ser Gly Gln Asn Arg Ser Gln Tyr Asp Ala Ala Pro
    530                 535                 540

Arg Leu Ala Glu Met Arg Glu Arg Met Val Ala Arg Gly Val Ser Ala
545                 550                 555                 560

Ser Pro Ile Gln Met Pro Phe Cys Thr Gln Gly Asn Ala Thr Glu Cys
                565                 570                 575

Ala Gln Val Glu Gly
            580

<210> SEQ ID NO 14
<211> LENGTH: 249
<212> TYPE: PRT
<213> ORGANISM: Fusarium venenatum

<400> SEQUENCE: 14

Met Trp Ser Lys Ala Leu Leu Ala Val Ala Ala Phe Ala Phe Thr Pro
1               5                   10                  15

Ala Asn Ala Ile Trp Pro Val Pro Lys Lys Ile Ser Thr Gly Asp Lys
                20                  25                  30

Ala Phe Phe Ile Asp Gln Thr Ile Asp Ile Thr Tyr Asn Gly Gly Phe
            35                  40                  45

Ile Pro Tyr Thr Tyr Asn Tyr Gln Pro Asp Ala Gly Ser Lys Phe Ser
        50                  55                  60

Ser Lys Gln Ile Val Gln Ala Gly Val Ser Arg Ala Leu Gln Gly Ile
65                  70                  75                  80

Phe Gln Asp Asn Phe Val Pro Trp Met Leu Arg Glu Arg Asp Ser Asp
                85                  90                  95

Phe Glu Pro Asp Leu Gln Lys Lys Gln Trp Val Lys Ser Leu Lys Ile
                100                 105                 110

Val Gln Thr Glu Glu Asp Asp Glu Ser Thr Phe Lys Pro Leu Asn Gly
            115                 120                 125

Glu Val Asp Glu Ser Tyr Ser Leu Ser Leu Ser Glu Lys Gly Glu Ala
        130                 135                 140
```

-continued

```
Ser Ile Lys Ala Lys Ser Ser Thr Gly Val Leu His Gly Leu Glu Thr
145                 150                 155                 160

Phe Val Gln Leu Phe Phe Lys His Ser Ser Gly Thr Ser Trp Tyr Thr
                165                 170                 175

Pro His Ala Pro Val Ser Ile Gln Asp Glu Pro Glu Tyr Pro His Arg
            180                 185                 190

Gly Ile Leu Leu Asp Val Ala Arg Ser Phe Phe Glu Val Lys His Ile
        195                 200                 205

Lys Arg Thr Ile Asp Ala Met Ser Trp Ser Lys Leu Asn Arg Leu His
    210                 215                 220

Leu His Ile Thr Asp Ser Gln Ser Trp Pro Leu Glu Ile Pro Ala Leu
225                 230                 235                 240

Pro Lys Leu Ala Glu Lys Gly Ala Tyr
                245

<210> SEQ ID NO 15
<211> LENGTH: 249
<212> TYPE: PRT
<213> ORGANISM: Fusarium sporotrichiodes
<220> FEATURE:
<221> NAME/KEY: UNSURE
<222> LOCATION: (42)
<223> OTHER INFORMATION: Xaa is Ile or Leu

<400> SEQUENCE: 15

Met Trp Ser Lys Ala Leu Leu Ala Val Ala Ala Phe Ala Phe Thr Pro
  1               5                  10                  15

Ala Asn Ala Ile Trp Pro Val Pro Lys Lys Ile Ser Thr Gly Asp Lys
            20                  25                  30

Ala Leu Phe Ile Asp Gln Thr Ile Asp Xaa Thr Tyr Asn Gly Asp Phe
        35                  40                  45

Ile Pro Tyr Thr Tyr Asn Tyr Gln Pro Asp Ala Gly Ser Lys Phe Ser
    50                  55                  60

Ser Lys Gln Ile Ile Gln Ala Gly Val Ser Arg Ala Leu Gln Gly Val
65                  70                  75                  80

Phe Gln Asp Asn Phe Val Pro Trp Met Leu Arg Glu Arg Asp Ser Asp
                85                  90                  95

Phe Glu Pro Asp Leu Gln Lys Lys Gln Trp Val Lys Ser Leu Lys Ile
            100                 105                 110

Ile Gln Thr Glu Glu Asp Asp Glu Ser Thr Phe Lys Pro Leu Asn Gly
        115                 120                 125

Glu Val Asp Glu Ser Tyr Ser Leu Ser Leu Ser Glu Lys Gly Glu Ala
    130                 135                 140

Ser Ile Lys Ala Lys Ser Ser Thr Gly Val Leu His Gly Leu Glu Thr
145                 150                 155                 160

Phe Val Gln Leu Phe Phe Lys His Ser Ser Gly Thr Ser Trp Tyr Thr
                165                 170                 175

Pro His Ala Pro Val Ser Ile Gln Asp Glu Pro Glu Tyr Pro His Arg
            180                 185                 190

Gly Ile Leu Leu Asp Val Ala Arg Ser Phe Phe Glu Val Lys His Ile
        195                 200                 205

Lys Arg Thr Ile Asp Ala Met Ser Trp Ser Lys Leu Asn Arg Leu His
    210                 215                 220

Leu His Ile Thr Asp Ser Gln Ser Trp Pro Leu Glu Ile Pro Ala Leu
225                 230                 235                 240
```

```
Pro Lys Leu Ala Glu Lys Gly Ala Tyr
            245

<210> SEQ ID NO 16
<211> LENGTH: 932
<212> TYPE: DNA
<213> ORGANISM: Fusarium venenatum
<220> FEATURE:
<221> NAME/KEY: CDS
<222> LOCATION: (18)..(923)

<400> SEQUENCE: 16
ggatccacca accagcg atg aag ttc ttc agc act ctt agc acc ctt gcg           50
                   Met Lys Phe Phe Ser Thr Leu Ser Thr Leu Ala
                    1               5                      10 gtg gcc ctc atg atg agt ggc gag gct ctg gct ggt acc tac aag ggt          98
Val Ala Leu Met Met Ser Gly Glu Ala Leu Ala Gly Thr Tyr Lys Gly
         15                  20                  25 ttc agc att ggc gcc aac agg gct gat ggt gcc tgt aag tgg gag gcc         146
Phe Ser Ile Gly Ala Asn Arg Ala Asp Gly Ala Cys Lys Trp Glu Ala
     30                  35                  40 gac tgg aag aag gat ttc cag gcc atc aag agc tgg aac aag ggt ttc         194
Asp Trp Lys Lys Asp Phe Gln Ala Ile Lys Ser Trp Asn Lys Gly Phe
 45                  50                  55 aac gct gtt cgt ctg tac tct gcc tct gac tgt aac aca ctt gtc aag         242
Asn Ala Val Arg Leu Tyr Ser Ala Ser Asp Cys Asn Thr Leu Val Lys
 60                  65                  70                  75 gct gtc ccc gct gcc aag gcc act ggc atg aag atc ctt gtt ggc gtc         290
Ala Val Pro Ala Ala Lys Ala Thr Gly Met Lys Ile Leu Val Gly Val
                 80                  85                  90 tgg gcc acc gat gat gct cac ttc ggc cgc gac aag gcc gcc ctc ctc         338
Trp Ala Thr Asp Asp Ala His Phe Gly Arg Asp Lys Ala Ala Leu Leu
             95                 100                 105 aag gct atc aag cag cac ggc acc ggc tgg atc gcc gcc atc agt gtc         386
Lys Ala Ile Lys Gln His Gly Thr Gly Trp Ile Ala Ala Ile Ser Val
        110                 115                 120 gga tcc gag gac ctc tac cgt gag gac atc tcc ccc cag aag ctc gca         434
Gly Ser Glu Asp Leu Tyr Arg Glu Asp Ile Ser Pro Gln Lys Leu Ala
    125                 130                 135 cag cag atc tac gac gtc cga ggc atg gtc cac caa tac aac aag aac         482
Gln Gln Ile Tyr Asp Val Arg Gly Met Val His Gln Tyr Asn Lys Asn
140                 145                 150                 155 ctc aag gtc gga cat acc gac acc tgg acc gct tgg gtc gac ggc cgc         530
Leu Lys Val Gly His Thr Asp Thr Trp Thr Ala Trp Val Asp Gly Arg
                160                 165                 170 aac gac gtc gtc acc aag gcc tgc gat atc gcc att aca aac ggt ttc         578
Asn Asp Val Val Thr Lys Ala Cys Asp Ile Ala Ile Thr Asn Gly Phe
            175                 180                 185 ccc tac tgg aag ggt gtt ccc atc aag gat gct ctc cgc ctc aag acc         626
Pro Tyr Trp Lys Gly Val Pro Ile Lys Asp Ala Leu Arg Leu Lys Thr
        190                 195                 200 ttc cag aac tcc ttc tgg aac gtc cag aag cac gtc aag gct gtc aac         674
Phe Gln Asn Ser Phe Trp Asn Val Gln Lys His Val Lys Ala Val Asn
    205                 210                 215 tcc aag gct gct gtc tgg gtt ggc gag acc ggc tgg cct aca aag gga         722
Ser Lys Ala Ala Val Trp Val Gly Glu Thr Gly Trp Pro Thr Lys Gly
220                 225                 230                 235 ccc aac tac cag aag gct gct gcc acg acc gcc agt ctc cag cag ttc         770
Pro Asn Tyr Gln Lys Ala Ala Ala Thr Thr Ala Ser Leu Gln Gln Phe
                240                 245                 250 tac aac aat gtc ggt tgc tgg ctc tgg cag cag aag gag gcc agt ggt         818
```

-continued

```
Tyr Asn Asn Val Gly Cys Trp Leu Trp Gln Gln Lys Glu Ala Ser Gly
            255                 260                 265 ttc tgg ttc act gct ttc gat aca cct gcg cac agc acc gag gtt gag    866
Phe Trp Phe Thr Ala Phe Asp Thr Pro Ala His Ser Thr Glu Val Glu
        270                 275                 280 aag tac ttc ggt att gcc aac cag gac cgc aag ctc aag ttc agc ctt    914
Lys Tyr Phe Gly Ile Ala Asn Gln Asp Arg Lys Leu Lys Phe Ser Leu
    285                 290                 295 act tgc taa gccagatct                                              932
Thr Cys
300
```

<210> SEQ ID NO 17
<211> LENGTH: 301
<212> TYPE: PRT
<213> ORGANISM: Fusarium venenatum

<400> SEQUENCE: 17

```
Met Lys Phe Phe Ser Thr Leu Ser Thr Leu Ala Val Ala Leu Met Met
  1               5                  10                  15

Ser Gly Glu Ala Leu Ala Gly Thr Tyr Lys Gly Phe Ser Ile Gly Ala
                 20                  25                  30

Asn Arg Ala Asp Gly Ala Cys Lys Trp Glu Ala Asp Trp Lys Lys Asp
             35                  40                  45

Phe Gln Ala Ile Lys Ser Trp Asn Lys Gly Phe Asn Ala Val Arg Leu
         50                  55                  60

Tyr Ser Ala Ser Asp Cys Asn Thr Leu Val Lys Ala Val Pro Ala Ala
 65                  70                  75                  80

Lys Ala Thr Gly Met Lys Ile Leu Val Gly Val Trp Ala Thr Asp Asp
                 85                  90                  95

Ala His Phe Gly Arg Asp Lys Ala Ala Leu Leu Lys Ala Ile Lys Gln
            100                 105                 110

His Gly Thr Gly Trp Ile Ala Ala Ile Ser Val Gly Ser Glu Asp Leu
        115                 120                 125

Tyr Arg Glu Asp Ile Ser Pro Gln Lys Leu Ala Gln Gln Ile Tyr Asp
    130                 135                 140

Val Arg Gly Met Val His Gln Tyr Asn Lys Asn Leu Lys Val Gly His
145                 150                 155                 160

Thr Asp Thr Trp Thr Ala Trp Val Asp Gly Arg Asn Asp Val Val Thr
                165                 170                 175

Lys Ala Cys Asp Ile Ala Ile Thr Asn Gly Phe Pro Tyr Trp Lys Gly
            180                 185                 190

Val Pro Ile Lys Asp Ala Leu Arg Leu Lys Thr Phe Gln Asn Ser Phe
        195                 200                 205

Trp Asn Val Gln Lys His Val Lys Ala Val Asn Ser Lys Ala Ala Val
    210                 215                 220

Trp Val Gly Glu Thr Gly Trp Pro Thr Lys Gly Pro Asn Tyr Gln Lys
225                 230                 235                 240

Ala Ala Ala Thr Thr Ala Ser Leu Gln Gln Phe Tyr Asn Asn Val Gly
                245                 250                 255

Cys Trp Leu Trp Gln Gln Lys Glu Ala Ser Gly Phe Trp Phe Thr Ala
            260                 265                 270

Phe Asp Thr Pro Ala His Ser Thr Glu Val Glu Lys Tyr Phe Gly Ile
        275                 280                 285

Ala Asn Gln Asp Arg Lys Leu Lys Phe Ser Leu Thr Cys
    290                 295                 300
```

<210> SEQ ID NO 18
<211> LENGTH: 1227
<212> TYPE: DNA
<213> ORGANISM: Fusarium venenatum
<220> FEATURE:
<221> NAME/KEY: CDS
<222> LOCATION: (18)..(1217)

<400> SEQUENCE: 18

| | | | | | | | | |
|---|---|---|---|---|---|---|---|---|
| ggatccaaca ccacgcg atg ggt ggt gga ccc gaa ggt ttc cgc acc gtt | | | | | | | | 50 |
| Met Gly Gly Gly Pro Glu Gly Phe Arg Thr Val | | | | | | | | |
| 1 5 10 | | | | | | | | |
| gcg tat ttc gtc aac tgg gct atc tat gca cga aag cat cgt cct cag | | | | | | | | 98 |
| Ala Tyr Phe Val Asn Trp Ala Ile Tyr Ala Arg Lys His Arg Pro Gln | | | | | | | | |
| 15 20 25 | | | | | | | | |
| gat ctt ccc gtg gag aac ctg aca cat att ctt tac tcg ttc gct aat | | | | | | | | 146 |
| Asp Leu Pro Val Glu Asn Leu Thr His Ile Leu Tyr Ser Phe Ala Asn | | | | | | | | |
| 30 35 40 | | | | | | | | |
| att cgt agc gac tct ggc gaa gtc cat ctc acc gac tca tgg gcc gat | | | | | | | | 194 |
| Ile Arg Ser Asp Ser Gly Glu Val His Leu Thr Asp Ser Trp Ala Asp | | | | | | | | |
| 45 50 55 | | | | | | | | |
| acc gat att cat tgg gat gga gat tcc tgg aat gat gtc ggt acc aac | | | | | | | | 242 |
| Thr Asp Ile His Trp Asp Gly Asp Ser Trp Asn Asp Val Gly Thr Asn | | | | | | | | |
| 60 65 70 75 | | | | | | | | |
| ttg tac ggt tgc atg aag cag ctt aac ctg ttg aaa aga cgt aac cga | | | | | | | | 290 |
| Leu Tyr Gly Cys Met Lys Gln Leu Asn Leu Leu Lys Arg Arg Asn Arg | | | | | | | | |
| 80 85 90 | | | | | | | | |
| aac ctc aag gtt ctt ctc agt att gga ggt tgg acc ttc agt agc aac | | | | | | | | 338 |
| Asn Leu Lys Val Leu Leu Ser Ile Gly Gly Trp Thr Phe Ser Ser Asn | | | | | | | | |
| 95 100 105 | | | | | | | | |
| ttc aag ggc ccc gct agc aca ccc caa gga cgt gac aca ttc gcc aag | | | | | | | | 386 |
| Phe Lys Gly Pro Ala Ser Thr Pro Gln Gly Arg Asp Thr Phe Ala Lys | | | | | | | | |
| 110 115 120 | | | | | | | | |
| agc tgt gtc gat ctg atc aag aac ctc ggt ttt gac ggt ata gat atc | | | | | | | | 434 |
| Ser Cys Val Asp Leu Ile Lys Asn Leu Gly Phe Asp Gly Ile Asp Ile | | | | | | | | |
| 125 130 135 | | | | | | | | |
| gat tgg gag tac ccc cag gat gcc aac gag gct aga aac tat gtc gaa | | | | | | | | 482 |
| Asp Trp Glu Tyr Pro Gln Asp Ala Asn Glu Ala Arg Asn Tyr Val Glu | | | | | | | | |
| 140 145 150 155 | | | | | | | | |
| ctt ctg ggc gcc gtg cgt cat gag atg gat gca tat gca cag aca ttg | | | | | | | | 530 |
| Leu Leu Gly Ala Val Arg His Glu Met Asp Ala Tyr Ala Gln Thr Leu | | | | | | | | |
| 160 165 170 | | | | | | | | |
| agc caa cct tat cac ttt gag ttg act gtg gcc tgt cca gcc ggt gcg | | | | | | | | 578 |
| Ser Gln Pro Tyr His Phe Glu Leu Thr Val Ala Cys Pro Ala Gly Ala | | | | | | | | |
| 175 180 185 | | | | | | | | |
| aca aac ttc cag aag ctc gat atc cgt gga atg gat caa tac ctc gac | | | | | | | | 626 |
| Thr Asn Phe Gln Lys Leu Asp Ile Arg Gly Met Asp Gln Tyr Leu Asp | | | | | | | | |
| 190 195 200 | | | | | | | | |
| ttc tgg aac ctc atg gct tac gac tat gct ggt tct tgg gac caa act | | | | | | | | 674 |
| Phe Trp Asn Leu Met Ala Tyr Asp Tyr Ala Gly Ser Trp Asp Gln Thr | | | | | | | | |
| 205 210 215 | | | | | | | | |
| gcg ggt cat cag gcc aac ctg tac cca tct cac gac aac cca gta tca | | | | | | | | 722 |
| Ala Gly His Gln Ala Asn Leu Tyr Pro Ser His Asp Asn Pro Val Ser | | | | | | | | |
| 220 225 230 235 | | | | | | | | |
| acc cca ttc tct acc tct gct gcc atc gac ttt tac gtc cgc agc ggt | | | | | | | | 770 |
| Thr Pro Phe Ser Thr Ser Ala Ala Ile Asp Phe Tyr Val Arg Ser Gly | | | | | | | | |
| 240 245 250 | | | | | | | | |
| gtg aac cct tca aag ata gtt ctc ggc atg cca ctc tac ggc cga gcc | | | | | | | | 818 |
| Val Asn Pro Ser Lys Ile Val Leu Gly Met Pro Leu Tyr Gly Arg Ala | | | | | | | | |
| 255 260 265 | | | | | | | | |

-continued

```
ttt gag aac acc gac ggt ccc ggc cgc ccc tac caa ggc gtt gga caa         866
Phe Glu Asn Thr Asp Gly Pro Gly Arg Pro Tyr Gln Gly Val Gly Gln
        270                 275                 280 ggt tcc tgg gaa cag gga gtc tac gat tac aag gcg ctt ccc cta gag         914
Gly Ser Trp Glu Gln Gly Val Tyr Asp Tyr Lys Ala Leu Pro Leu Glu
    285                 290                 295 ggc gcg caa gag tac gga gat aga gga tgc tgt gcc agc tac tgc tac         962
Gly Ala Gln Glu Tyr Gly Asp Arg Gly Cys Cys Ala Ser Tyr Cys Tyr
300                 305                 310                 315 aac cct cag tca cgt acc atg gtc acc tac gac acg ccg cgg gtc gcc        1010
Asn Pro Gln Ser Arg Thr Met Val Thr Tyr Asp Thr Pro Arg Val Ala
                320                 325                 330 tgg gat aag gcc gag tat gtg aag agg tgg aag ctg gga ggc gct atg        1058
Trp Asp Lys Ala Glu Tyr Val Lys Arg Trp Lys Leu Gly Gly Ala Met
            335                 340                 345 tgg tgg gag agc agc gcg gat aag cag ggc gag cag agt ttg atc aca        1106
Trp Trp Glu Ser Ser Ala Asp Lys Gln Gly Glu Gln Ser Leu Ile Thr
        350                 355                 360 acg gtt gtg aac gga ttc gga ggt cag gga gcg ctc atg aga cag gac        1154
Thr Val Val Asn Gly Phe Gly Gly Gln Gly Ala Leu Met Arg Gln Asp
    365                 370                 375 aac tgt att gag tat ccc gcg acc aag tac gat aac ttg cga aat ggg        1202
Asn Cys Ile Glu Tyr Pro Ala Thr Lys Tyr Asp Asn Leu Arg Asn Gly
380                 385                 390                 395 ttc ccg gac aat tga ggcgagatct                                         1227
Phe Pro Asp Asn
```

<210> SEQ ID NO 19
<211> LENGTH: 399
<212> TYPE: PRT
<213> ORGANISM: Fusarium venenatum

<400> SEQUENCE: 19

```
Met Gly Gly Gly Pro Glu Gly Phe Arg Thr Val Ala Tyr Phe Val Asn
  1               5                  10                  15

Trp Ala Ile Tyr Ala Arg Lys His Arg Pro Gln Asp Leu Pro Val Glu
             20                  25                  30

Asn Leu Thr His Ile Leu Tyr Ser Phe Ala Asn Ile Arg Ser Asp Ser
         35                  40                  45

Gly Glu Val His Leu Thr Asp Ser Trp Ala Asp Thr Asp Ile His Trp
     50                  55                  60

Asp Gly Asp Ser Trp Asn Asp Val Gly Thr Asn Leu Tyr Gly Cys Met
 65                  70                  75                  80

Lys Gln Leu Asn Leu Leu Lys Arg Arg Asn Arg Asn Leu Lys Val Leu
                 85                  90                  95

Leu Ser Ile Gly Gly Trp Thr Phe Ser Ser Asn Phe Lys Gly Pro Ala
            100                 105                 110

Ser Thr Pro Gln Gly Arg Asp Thr Phe Ala Lys Ser Cys Val Asp Leu
        115                 120                 125

Ile Lys Asn Leu Gly Phe Asp Gly Ile Asp Ile Asp Trp Glu Tyr Pro
    130                 135                 140

Gln Asp Ala Asn Glu Ala Arg Asn Tyr Val Glu Leu Leu Gly Ala Val
145                 150                 155                 160

Arg His Glu Met Asp Ala Tyr Ala Gln Thr Leu Ser Gln Pro Tyr His
                165                 170                 175

Phe Glu Leu Thr Val Ala Cys Pro Ala Gly Ala Thr Asn Phe Gln Lys
            180                 185                 190
```

-continued

```
Leu Asp Ile Arg Gly Met Asp Gln Tyr Leu Asp Phe Trp Asn Leu Met
            195                 200                 205
Ala Tyr Asp Tyr Ala Gly Ser Trp Asp Gln Thr Ala Gly His Gln Ala
        210                 215                 220
Asn Leu Tyr Pro Ser His Asp Asn Pro Val Ser Thr Pro Phe Ser Thr
225                 230                 235                 240
Ser Ala Ala Ile Asp Phe Tyr Val Arg Ser Gly Val Asn Pro Ser Lys
                245                 250                 255
Ile Val Leu Gly Met Pro Leu Tyr Gly Arg Ala Phe Glu Asn Thr Asp
            260                 265                 270
Gly Pro Gly Arg Pro Tyr Gln Gly Val Gly Gln Gly Ser Trp Glu Gln
        275                 280                 285
Gly Val Tyr Asp Tyr Lys Ala Leu Pro Leu Glu Gly Ala Gln Glu Tyr
    290                 295                 300
Gly Asp Arg Gly Cys Cys Ala Ser Tyr Cys Tyr Asn Pro Gln Ser Arg
305                 310                 315                 320
Thr Met Val Thr Tyr Asp Thr Pro Arg Val Ala Trp Asp Lys Ala Glu
                325                 330                 335
Tyr Val Lys Arg Trp Lys Leu Gly Gly Ala Met Trp Trp Glu Ser Ser
            340                 345                 350
Ala Asp Lys Gln Gly Glu Gln Ser Leu Ile Thr Thr Val Val Asn Gly
        355                 360                 365
Phe Gly Gly Gln Gly Ala Leu Met Arg Gln Asp Asn Cys Ile Glu Tyr
    370                 375                 380
Pro Ala Thr Lys Tyr Asp Asn Leu Arg Asn Gly Phe Pro Asp Asn
385                 390                 395

<210> SEQ ID NO 20
<211> LENGTH: 1781
<212> TYPE: DNA
<213> ORGANISM: Fusarium venenatum
<220> FEATURE:
<221> NAME/KEY: CDS
<222> LOCATION: (18)..(1763)

<400> SEQUENCE: 20
ggatccacca accagcg atg tgg tcc aag gct ctt ctg gcc gtt gcc gcc         50
                Met Trp Ser Lys Ala Leu Leu Ala Val Ala Ala
                 1               5                  10 ttc gcc ttt acc ccc gcc aat gcc ata tgg cca gtg cca aag aag atc       98
Phe Ala Phe Thr Pro Ala Asn Ala Ile Trp Pro Val Pro Lys Lys Ile
            15                  20                  25 tct act gga gac aag gcc ttc ttc atc gat caa aca att gat atc acc      146
Ser Thr Gly Asp Lys Ala Phe Phe Ile Asp Gln Thr Ile Asp Ile Thr
        30                  35                  40 tat aat gga ggc ttt atc cct tac act tac aac tac cag ccc gat gct      194
Tyr Asn Gly Gly Phe Ile Pro Tyr Thr Tyr Asn Tyr Gln Pro Asp Ala
    45                  50                  55 ggc tcc aag ttc agc agt aag caa atc gtc caa gcc ggc gtc tct cgt      242
Gly Ser Lys Phe Ser Ser Lys Gln Ile Val Gln Ala Gly Val Ser Arg
60                  65                  70                  75 gcc ctc cag ggc atc ttc cag gac aac ttt gtc cca tgg atg ctt cgc      290
Ala Leu Gln Gly Ile Phe Gln Asp Asn Phe Val Pro Trp Met Leu Arg
                80                  85                  90 gaa cgc gat tcc gat ttc gag cct gac ctg caa aag aag cag tgg gtg      338
Glu Arg Asp Ser Asp Phe Glu Pro Asp Leu Gln Lys Lys Gln Trp Val
            95                 100                 105
```

```
aag tcg cta aag att gtc cag acc gag gag gat gac gag agt acc ttc        386
Lys Ser Leu Lys Ile Val Gln Thr Glu Glu Asp Asp Glu Ser Thr Phe
        110                 115                 120 aag cct ctc aat ggt gag gtt gac gag tcg tac tct ctc tca ctt tct        434
Lys Pro Leu Asn Gly Glu Val Asp Glu Ser Tyr Ser Leu Ser Leu Ser
125                 130                 135 gaa aag ggc gag gct tcc atc aag gcc aag tct tct aca ggc gtc ctg        482
Glu Lys Gly Glu Ala Ser Ile Lys Ala Lys Ser Ser Thr Gly Val Leu
140                 145                 150                 155 cat gga ctt gag acc ttt gtc caa ctt ttc ttc aag cac agc tct ggc        530
His Gly Leu Glu Thr Phe Val Gln Leu Phe Phe Lys His Ser Ser Gly
                160                 165                 170 act tcc tgg tac acg ccg cac gcg cct gtc tcg atc cag gat gag ccc        578
Thr Ser Trp Tyr Thr Pro His Ala Pro Val Ser Ile Gln Asp Glu Pro
            175                 180                 185 gag tac cct cat cga ggc att ctt ctc gat gtt gcc cgt agc ttt ttt        626
Glu Tyr Pro His Arg Gly Ile Leu Leu Asp Val Ala Arg Ser Phe Phe
        190                 195                 200 gaa gtc aag cac atc aag cgc aca atc gac gcc atg tcg tgg agc aag        674
Glu Val Lys His Ile Lys Arg Thr Ile Asp Ala Met Ser Trp Ser Lys
205                 210                 215 ctg aat cgc ctt cac ctt cac atc act gac tcg cag tcc tgg cct ctc        722
Leu Asn Arg Leu His Leu His Ile Thr Asp Ser Gln Ser Trp Pro Leu
220                 225                 230                 235 gag atc cca gcc cta ccc aaa ctg gcc gaa aag ggt gca tac cgc aaa        770
Glu Ile Pro Ala Leu Pro Lys Leu Ala Glu Lys Gly Ala Tyr Arg Lys
                240                 245                 250 ggc ctg acc tac tct cct gag gat ctt gcc ggt att tat gag tat ggt        818
Gly Leu Thr Tyr Ser Pro Glu Asp Leu Ala Gly Ile Tyr Glu Tyr Gly
            255                 260                 265 atc cac cgc gga gtc gag gtc atc atg gag att gac atg ccc ggc cat        866
Ile His Arg Gly Val Glu Val Ile Met Glu Ile Asp Met Pro Gly His
        270                 275                 280 atc ggt gtc gtt gag ctt gcc tat aag gat ctc att gtc gcg tac aat        914
Ile Gly Val Val Glu Leu Ala Tyr Lys Asp Leu Ile Val Ala Tyr Asn
285                 290                 295 gag aag cct tat caa tgg tgg tgt aag gag cca ccc tgt ggt gcg ttc        962
Glu Lys Pro Tyr Gln Trp Trp Cys Lys Glu Pro Pro Cys Gly Ala Phe
300                 305                 310                 315 cgc atg aac agc tct gat gtt tat gac ttt ctc gac act ctt ttt gat       1010
Arg Met Asn Ser Ser Asp Val Tyr Asp Phe Leu Asp Thr Leu Phe Asp
                320                 325                 330 gac ctc ttc cct cgc att tcc aag tac agt cct tac ttc cac ctt ggt       1058
Asp Leu Phe Pro Arg Ile Ser Lys Tyr Ser Pro Tyr Phe His Leu Gly
            335                 340                 345 gga gac gag ctc aac cac aac gat tcc aga ctt gac cct gat gtg cgc       1106
Gly Asp Glu Leu Asn His Asn Asp Ser Arg Leu Asp Pro Asp Val Arg
        350                 355                 360 tct aac gag acc gag gtt ctg gcg cct ctt ttg caa aag ttc gtc gat       1154
Ser Asn Glu Thr Glu Val Leu Ala Pro Leu Leu Gln Lys Phe Val Asp
365                 370                 375 tac act cac ggc aag gtt cga gat gcc ggc atg act ccg ttc gtc tgg       1202
Tyr Thr His Gly Lys Val Arg Asp Ala Gly Met Thr Pro Phe Val Trp
380                 385                 390                 395 gag gag atg att acc gaa tgg aac atg act ctg ggt aaa gac gtt gtg       1250
Glu Glu Met Ile Thr Glu Trp Asn Met Thr Leu Gly Lys Asp Val Val
                400                 405                 410 att cag tcc tgg ctc ggt ggc ggt gct atc aag acc ctg gct gag gct       1298
Ile Gln Ser Trp Leu Gly Gly Gly Ala Ile Lys Thr Leu Ala Glu Ala
            415                 420                 425
```

```
ggt cac aag gta atc gat agt gat tac aac ttc tgg tac ctt gac tgt    1346
Gly His Lys Val Ile Asp Ser Asp Tyr Asn Phe Trp Tyr Leu Asp Cys
        430                 435                 440 ggg cgt gga cag tgg ctc aac ttt gac aac ggc gat gcc ttt caa aca    1394
Gly Arg Gly Gln Trp Leu Asn Phe Asp Asn Gly Asp Ala Phe Gln Thr
    445                 450                 455 tac tac ccc ttc aac gac tgg tgc ggt cct acc aag agc tgg cgg ctc    1442
Tyr Tyr Pro Phe Asn Asp Trp Cys Gly Pro Thr Lys Ser Trp Arg Leu
460                 465                 470                 475 atc tac tcc cac gat cct cgg gcc ggt cta tcc gag gaa gca gcc aag    1490
Ile Tyr Ser His Asp Pro Arg Ala Gly Leu Ser Glu Glu Ala Ala Lys
                480                 485                 490 cgc gtg ctt ggt ggt gag gcg gcc gta tgg act gag act atc gac agt    1538
Arg Val Leu Gly Gly Glu Ala Ala Val Trp Thr Glu Thr Ile Asp Ser
            495                 500                 505 gtt aac ctc gat acc att gtg tgg ccc cgc gct gca gtg atg gga gaa    1586
Val Asn Leu Asp Thr Ile Val Trp Pro Arg Ala Ala Val Met Gly Glu
        510                 515                 520 gtt ctc tgg tca ggc cga act gac gcc tca ggc cag aac aga tcg cag    1634
Val Leu Trp Ser Gly Arg Thr Asp Ala Ser Gly Gln Asn Arg Ser Gln
    525                 530                 535 tat gat gct gca ccg cga ctg gct gag atg cgc gag cgt atg gtg gct    1682
Tyr Asp Ala Ala Pro Arg Leu Ala Glu Met Arg Glu Arg Met Val Ala
540                 545                 550                 555 cga gga gtg agt gct tca cca att cag atg ccc ttc tgt aca cag ggc    1730
Arg Gly Val Ser Ala Ser Pro Ile Gln Met Pro Phe Cys Thr Gln Gly
                560                 565                 570 aat gcc acc gag tgt gcg caa gtc gag gga tga taaatttgac gcagatct    1781
Asn Ala Thr Glu Cys Ala Gln Val Glu Gly
            575                 580

<210> SEQ ID NO 21
<211> LENGTH: 581
<212> TYPE: PRT
<213> ORGANISM: Fusarium venenatum

<400> SEQUENCE: 21

Met Trp Ser Lys Ala Leu Leu Ala Val Ala Ala Phe Ala Phe Thr Pro
1               5                   10                  15

Ala Asn Ala Ile Trp Pro Val Pro Lys Lys Ile Ser Thr Gly Asp Lys
            20                  25                  30

Ala Phe Phe Ile Asp Gln Thr Ile Asp Ile Thr Tyr Asn Gly Gly Phe
        35                  40                  45

Ile Pro Tyr Thr Tyr Asn Tyr Gln Pro Asp Ala Gly Ser Lys Phe Ser
    50                  55                  60

Ser Lys Gln Ile Val Gln Ala Gly Val Ser Arg Ala Leu Gln Gly Ile
65                  70                  75                  80

Phe Gln Asp Asn Phe Val Pro Trp Met Leu Arg Glu Arg Asp Ser Asp
                85                  90                  95

Phe Glu Pro Asp Leu Gln Lys Lys Gln Trp Val Lys Ser Leu Lys Ile
            100                 105                 110

Val Gln Thr Glu Glu Asp Asp Glu Ser Thr Phe Lys Pro Leu Asn Gly
        115                 120                 125

Glu Val Asp Glu Ser Tyr Ser Leu Ser Leu Ser Glu Lys Gly Glu Ala
    130                 135                 140

Ser Ile Lys Ala Lys Ser Ser Thr Gly Val Leu His Gly Leu Glu Thr
145                 150                 155                 160
```

-continued

```
Phe Val Gln Leu Phe Lys His Ser Ser Gly Thr Ser Trp Tyr Thr
            165                 170                 175

Pro His Ala Pro Val Ser Ile Gln Asp Glu Pro Glu Tyr Pro His Arg
            180                 185                 190

Gly Ile Leu Leu Asp Val Ala Arg Ser Phe Phe Glu Val Lys His Ile
            195                 200                 205

Lys Arg Thr Ile Asp Ala Met Ser Trp Ser Lys Leu Asn Arg Leu His
210                 215                 220

Leu His Ile Thr Asp Ser Gln Ser Trp Pro Leu Glu Ile Pro Ala Leu
225                 230                 235                 240

Pro Lys Leu Ala Glu Lys Gly Ala Tyr Arg Lys Gly Leu Thr Tyr Ser
            245                 250                 255

Pro Glu Asp Leu Ala Gly Ile Tyr Glu Tyr Gly Ile His Arg Gly Val
            260                 265                 270

Glu Val Ile Met Glu Ile Asp Met Pro Gly His Ile Gly Val Val Glu
            275                 280                 285

Leu Ala Tyr Lys Asp Leu Ile Val Ala Tyr Asn Glu Lys Pro Tyr Gln
290                 295                 300

Trp Trp Cys Lys Glu Pro Pro Cys Gly Ala Phe Arg Met Asn Ser Ser
305                 310                 315                 320

Asp Val Tyr Asp Phe Leu Asp Thr Leu Phe Asp Leu Phe Pro Arg
            325                 330                 335

Ile Ser Lys Tyr Ser Pro Tyr Phe His Leu Gly Gly Asp Glu Leu Asn
            340                 345                 350

His Asn Asp Ser Arg Leu Asp Pro Asp Val Arg Ser Asn Glu Thr Glu
            355                 360                 365

Val Leu Ala Pro Leu Leu Gln Lys Phe Val Asp Tyr Thr His Gly Lys
            370                 375                 380

Val Arg Asp Ala Gly Met Thr Pro Phe Val Trp Glu Glu Met Ile Thr
385                 390                 395                 400

Glu Trp Asn Met Thr Leu Gly Lys Asp Val Val Ile Gln Ser Trp Leu
            405                 410                 415

Gly Gly Gly Ala Ile Lys Thr Leu Ala Glu Ala Gly His Lys Val Ile
            420                 425                 430

Asp Ser Asp Tyr Asn Phe Trp Tyr Leu Asp Cys Gly Arg Gly Gln Trp
            435                 440                 445

Leu Asn Phe Asp Asn Gly Asp Ala Phe Gln Thr Tyr Tyr Pro Phe Asn
450                 455                 460

Asp Trp Cys Gly Pro Thr Lys Ser Trp Arg Leu Ile Tyr Ser His Asp
465                 470                 475                 480

Pro Arg Ala Gly Leu Ser Glu Glu Ala Ala Lys Arg Val Leu Gly Gly
            485                 490                 495

Glu Ala Ala Val Trp Thr Glu Thr Ile Asp Ser Val Asn Leu Asp Thr
            500                 505                 510

Ile Val Trp Pro Arg Ala Ala Val Met Gly Glu Val Leu Trp Ser Gly
            515                 520                 525

Arg Thr Asp Ala Ser Gly Gln Asn Arg Ser Gln Tyr Asp Ala Ala Pro
530                 535                 540

Arg Leu Ala Glu Met Arg Glu Arg Met Val Ala Arg Gly Val Ser Ala
545                 550                 555                 560

Ser Pro Ile Gln Met Pro Phe Cys Thr Gln Gly Asn Ala Thr Glu Cys
            565                 570                 575

Ala Gln Val Glu Gly
```

-continued

580

<210> SEQ ID NO 22
<211> LENGTH: 33
<212> TYPE: DNA
<213> ORGANISM: Zea mays

<400> SEQUENCE: 22
cacacacaac agatctcccc caaatccacc cgt                33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: MODIFIED
      UBI-1

<400> SEQUENCE: 23
cacacacaac agatttcccc caaatccacc cgt                33

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:MODIFIED
      UBI-1

<400> SEQUENCE: 24
cagatttccc ccaaatccca cacacaacc                29

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:LEADER
      SEQUENCE

<400> SEQUENCE: 25
ggatccacca accagcg                17

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence:M13F primer

<400> SEQUENCE: 26
gtaaaacgac ggccag                16

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:M13R primer

<400> SEQUENCE: 27
agcgaataac aatttcacac agga                24

<210> SEQ ID NO 28
<211> LENGTH: 22
<212> TYPE: DNA

```
<213> ORGANISM: Artificial Sequence
<220> FEATURE:
<223> OTHER INFORMATION: Description of Artificial Sequence:Primer

<400> SEQUENCE: 28
tcctggagcc cgtcagtatc gg                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 29
tggctgaata tcgacggttt cc                                              22

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 30
atttaggtga cactatag                                                   18

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 31
caggacagga aacagctatg acc                                             23

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 32
ctatcaagca gcacgg                                                     16

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence:Primer

<400> SEQUENCE: 33
ctggaaggtc ttgaggc                                                    17

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 34
gatatcgatt gggagtacc                                                  19
```

```
<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 35
catggtacgt gactgagg                                                    18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 36
caaccctcag tcacgtac                                                    18

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 37
cctcgttggc atcctg                                                      16

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence:Primer

<400> SEQUENCE: 38
agatccttat aggcaagctc aacgacaccg                                       30

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 39
cataaatacc ggcaagatcc                                                  20

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 40
atcgatatct ataccgtcaa aaccg                                            25

<210> SEQ ID NO 41
<211> LENGTH: 25
<212> TYPE: DNA
<213> ORGANISM: Artificial Sequence
<220> FEATURE:
```

```
<223> OTHER INFORMATION: Description of Artificial Sequence:Primer

<400> SEQUENCE: 41
atcgatatct ataccgtcaa aaccg                                    25

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 42
atctgctggg cgagcttc                                            18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 43
cagaaaccac tggcatcc                                            18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 44
aagttcggcc ttacttgc                                            18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 45
ctttgggctc gtattcac                                            18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 46
cttcagcact ctcagcac                                            18

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence:Primer

<400> SEQUENCE: 47
ggactgaggg agtgttggtt c                                        21
```

```
<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 48
tctaccctac aacactcatc                                              20

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 49
gtcgatcatg gtggaaag                                                18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 50
tgtccctgtt actaacgg                                                18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 51
tagtcgcctt tctaagcc                                                18

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 52
aagaatgcct cgatgagggt actcg                                        25

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 53
atctcactca cctcacctc                                               19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence:Primer
```

<400> SEQUENCE: 54
ccggtattta tgagtatgg                    19

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 55
gatagtctca gtccatacgg                    20

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence:Primer

<400> SEQUENCE: 56
gtaccttgac tgtgggc                       17

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 57
ggaaatgcga gggaag                        16

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 58
agatctcgcc tcaattgtcc gggaacc            27

<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 59
ggatccaaca ccacgcgatg ggtggtggac ccgaagg    37

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 60
agatctgcgt caaatttatc atccctcg            28

<210> SEQ ID NO 61
<211> LENGTH: 45

```
<212> TYPE: DNA
<213> ORGANISM: Artificial Sequence
<220> FEATURE:
<223> OTHER INFORMATION: Description of Artificial Sequence:Primer

<400> SEQUENCE: 61
ggatccacca accagcgatg tggtccaagg ctcttctggc cgttg              45

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 62
gcttcatgca accgtacaag ttgg                                     24

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence:Primer

<400> SEQUENCE: 63
cgacttcacc cactgcttct tttgc                                    25

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence:Primer

<400> SEQUENCE: 64
cccagacgcc aacaaggatc ttc                                      23

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 65
agatctggct tagcaagtaa ggctgaac                                 28

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence:Primer

<400> SEQUENCE: 66
ggatccacca accagcgatg aagttcttca gcactcttag c                  41

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 67
```

```
gtactgggtt ggtgagac                                              18

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence:Primer

<400> SEQUENCE: 68
ccattccaag accaggc                                               17

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 69
cccatctcat aaataacgtc                                            20

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence:Primer

<400> SEQUENCE: 70
cctgccttca tacgctat                                              18

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence:Primer

<400> SEQUENCE: 71
cctgccttca tacgctattt atttgc                                     26

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence:Primer

<400> SEQUENCE: 72
gacaccaacc agcgaacca                                             19

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence:Primer

<400> SEQUENCE: 73
cacacacaac cagatttccc ccaaatccac c                               31

<210> SEQ ID NO 74
<211> LENGTH: 31
<212> TYPE: DNA
<213> ORGANISM: Artificial Sequence
```

```
<220> FEATURE:
<223> OTHER INFORMATION: Description of Artificial Sequence:Primer

<400> SEQUENCE: 74
ggtggatttg ggggaaatct ggttgtgtgt g                              31

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: RT-PCR
      Primer

<400> SEQUENCE: 75
ctggaagttt gtcgcaccg                                            19

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: RT-PCR
      Primer

<400> SEQUENCE: 76
gagatagagg atgctgtgcc                                           20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: RT-PCR
      Primer

<400> SEQUENCE: 77
cagtgatgtg aaggtgaagg c                                         21

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: RT-PCR
      Primer

<400> SEQUENCE: 78
cgtatggact gagactatcg ac                                        22

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: RT-PCR
      Primer

<400> SEQUENCE: 79
gagcatcctt gatgggaaca c                                         21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: RT-PCR
```

```
                               -continued

Primer

<400> SEQUENCE: 80
gtcaactcca aggctgtcgt c                                              21

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: RT-PCR
      Primer

<400> SEQUENCE: 81
gccaaatgtt tgaacgatct gc                                             22

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: RT-PCR
      Primer

<400> SEQUENCE: 82
caacctcgtg ttgttcggag                                                20
```

What is claimed is:

1. An isolated nucleic acid molecule encoding a polypeptide having glucanase activity, selected from the group consisting of:
   (a) a nucleic acid sequence having at least 70% nucleotide sequence identity with SEQ ID NO:1 from nucleotide 37 through nucleotide 942, SEQ ID NO:3 from nucleotide 1801 through nucleotide 2761 or SEQ ID NO:16 from nucleotide 18 to nucleotide 923;
   (b) a nucleic acid sequence encoding a polypeptide having glucanase activity, said polypeptide having an amino acid sequence which has at least 80% identity with amino acids 1 to 301 of SEQ ID NO:2, 4, 5 or 17; and
   (c) a nucleic acid sequence which hybridizes under medium stringency or high stringency conditions with (i) SEQ ID NO:1 from nucleotide 37 through nucleotide 942, SEQ ID NO:3 from nucleotide 1801 through nucleotide 2761 or SEQ ID NO:16 from nucleotide 18 to nucleotide 923; or (ii) a complementary strand of (i).

2. The nucleic acid molecule of claim 1 as shown in SEQ ID NO:1, 3 or 16.

3. The nucleic acid molecule of claim 1 which is contained in plasmid Glu2 (NRRL B-30201), plasmid FvGluS (NRRL B-30204) or plasmid FvGluAS (NRRL B-30205).

4. A nucleic acid construct comprising a nucleic acid molecule of claim 1 operably linked to one or more control sequences which direct the production of a polypeptide having glucanase activity in an expression host.

5. A cell transformed with the isolated nucleic acid molecule of claim 1.

6. A plant transformed with the isolated nucleic acid molecule of claim 1.

7. A seed of the plant according to claim 6.

8. The plant of claim 6 wherein the plant is a monocot.

9. The plant of claim 8 wherein said monocotyledonous plant is wheat.

10. Sexually or asexually derived progeny of the plant of claim 6

11. A method for producing a polypeptide having glucanase activity, which comprises cultivating a recombinant host cell comprising a transformed cell having a nucleic acid molecule of claim 1 which encodes a polypeptide having glucanase activity under conditions suitable for production of the polypeptide; and recovering the polypeptide.

* * * * *